United States Patent
Dantanarayana et al.

(10) Patent No.: US 11,896,761 B2
(45) Date of Patent: *Feb. 13, 2024

(54) TEXTILE VENT ASSEMBLY

(71) Applicant: ResMed Pty Ltd, Bella Vista (AU)

(72) Inventors: Muditha Pradeep Dantanarayana, Sydney (AU); Memduh Guney, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 36 days.

This patent is subject to a terminal disclaimer.

(21) Appl. No.: 17/854,105

(22) Filed: Jun. 30, 2022

(65) Prior Publication Data

US 2022/0331531 A1    Oct. 20, 2022

Related U.S. Application Data

(63) Continuation of application No. 17/432,669, filed as application No. PCT/IB2020/051474 on Feb. 21, 2020, now Pat. No. 11,433,197.

(Continued)

(51) Int. Cl.
*A61M 16/00* (2006.01)
*A61M 16/06* (2006.01)

(52) U.S. Cl.
CPC .... *A61M 16/0054* (2013.01); *A61M 16/0003* (2014.02); *A61M 16/0616* (2014.02); *A61M 2202/0225* (2013.01); *A61M 2205/42* (2013.01)

(58) Field of Classification Search
CPC .......... A61M 16/0054; A61M 16/0003; A61M 16/0616; A61M 2202/0225;
(Continued)

(56) References Cited

U.S. PATENT DOCUMENTS 4,782,832 A    11/1988    Trimble et al.
4,944,310 A    7/1990    Sullivan
(Continued)

FOREIGN PATENT DOCUMENTS

WO    WO 98/004310 A1    2/1998
WO    WO 98/034665 A1    8/1998
(Continued)

OTHER PUBLICATIONS

Extended European Search Report dated Oct. 27, 2022 in European Application No. 20758863.3, 5 pages.
(Continued)

*Primary Examiner* — Victoria Murphy
(74) *Attorney, Agent, or Firm* — Nixon & Vanderhye P.C.

(57) ABSTRACT

A CPAP system for respiratory therapy includes an RPT device configured to supply a flow of gas at a therapeutic pressure, a patient interface, an air delivery conduit configured to pass the flow of gas from the RPT device to the patient interface, and a vent assembly configured to provide a vent flow of gas to discharge gas exhaled by the patient from a pressurized volume to ambient. The vent assembly includes a base including at least one first orifice to allow gas to be discharged along a primary vent flow path and at least one second orifice to allow gas to be discharged along a secondary vent flow path, a diffusing member provided to the base, and a membrane provided to the base. The membrane is configured to apportion the vent flow of gas along the primary vent flow path and the secondary vent flow path throughout respiratory therapy.

36 Claims, 53 Drawing Sheets

Related U.S. Application Data

(60) Provisional application No. 62/880,338, filed on Jul. 30, 2019, provisional application No. 62/808,901, filed on Feb. 22, 2019.

(58) Field of Classification Search
CPC .............. A61M 2205/42; A61M 16/20; A61M 16/204; A61M 16/205; A61M 16/203; A61M 16/208; A61M 16/0087; A61M 16/0066; A61M 16/0069; A61M 16/06; A61M 16/0622; A61M 16/0666
See application file for complete search history.

(56) References Cited

U.S. PATENT DOCUMENTS

| | | | |
|---|---|---|---|
| 5,370,656 A * | 12/1994 | Shevel | A61M 16/0436 206/440 |
| 6,532,959 B1 | 3/2003 | Berthon-Jones | |
| 6,581,594 B1 | 6/2003 | Drew et al. | |
| 6,662,803 B2 | 12/2003 | Gradon et al. | |
| 7,866,944 B2 | 1/2011 | Kenyon et al. | |
| 8,397,727 B2 | 3/2013 | Ng et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2004/0255948 A1* | 12/2004 | Smith | A61M 16/0057 128/206.15 |
| 2008/0078395 A1 | 4/2008 | Ho et al. | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2014/0246024 A1 | 9/2014 | Cragg et al. | |
| 2016/0008566 A1* | 1/2016 | Partington | A61M 16/1045 128/205.12 |
| 2016/0367782 A1 | 12/2016 | Henry et al. | |
| 2022/0168521 A1 | 6/2022 | Dantanarayana et al. | |

FOREIGN PATENT DOCUMENTS

| | | | | |
|---|---|---|---|---|
| WO | WO 2000/078381 A1 | 12/2000 | | |
| WO | WO 02/051486 A1 | 7/2002 | | |
| WO | WO 02/096342 A3 | 12/2002 | | |
| WO | WO-02096342 A2 * | 12/2002 | ............ | A61M 16/08 |
| WO | WO 2004/073778 A1 | 9/2004 | | |
| WO | WO 2005/063328 A1 | 7/2005 | | |
| WO | WO 2006/074513 A1 | 7/2006 | | |
| WO | WO 2006/130903 A1 | 12/2006 | | |
| WO | WO 2009/052560 A1 | 4/2009 | | |
| WO | WO 2010/135785 A1 | 12/2010 | | |
| WO | WO 2012/171072 A1 | 12/2012 | | |
| WO | WO 2013/020167 A1 | 2/2013 | | |
| WO | WO 2014/129913 A1 | 8/2014 | | |
| WO | WO 2016/041019 A1 | 3/2016 | | |
| WO | WO 2017/049358 A1 | 3/2017 | | |
| WO | WO 2018/053589 A1 | 3/2018 | | |
| WO | WO 2018/085889 A1 | 5/2018 | | |
| WO | WO 2018/126295 A1 | 7/2018 | | |

OTHER PUBLICATIONS

"*Respiratory Physiology*", by John B. West, Lippincott Williams & Wilkins, 9$^{th}$ edition published 2012 (8 pages).

International Search Report dated May 14, 2020 in International Application No. PCT/IB2020/051474, 12 pages.

Written Opinion of the International Search Authority dated May 14, 2020 in International Application No. PCT/IB2020/051474, 7 pages.

Notification Concerning Transmittal of International Preliminary Report on Patentability dated Sep. 2, 2021, together with IPRP, 9 pages.

Dantanarayana et al., U.S. Appl. No. 17/432,669, filed Aug. 20, 2021, for "Textile Vent Assembly," (parent application).

* cited by examiner

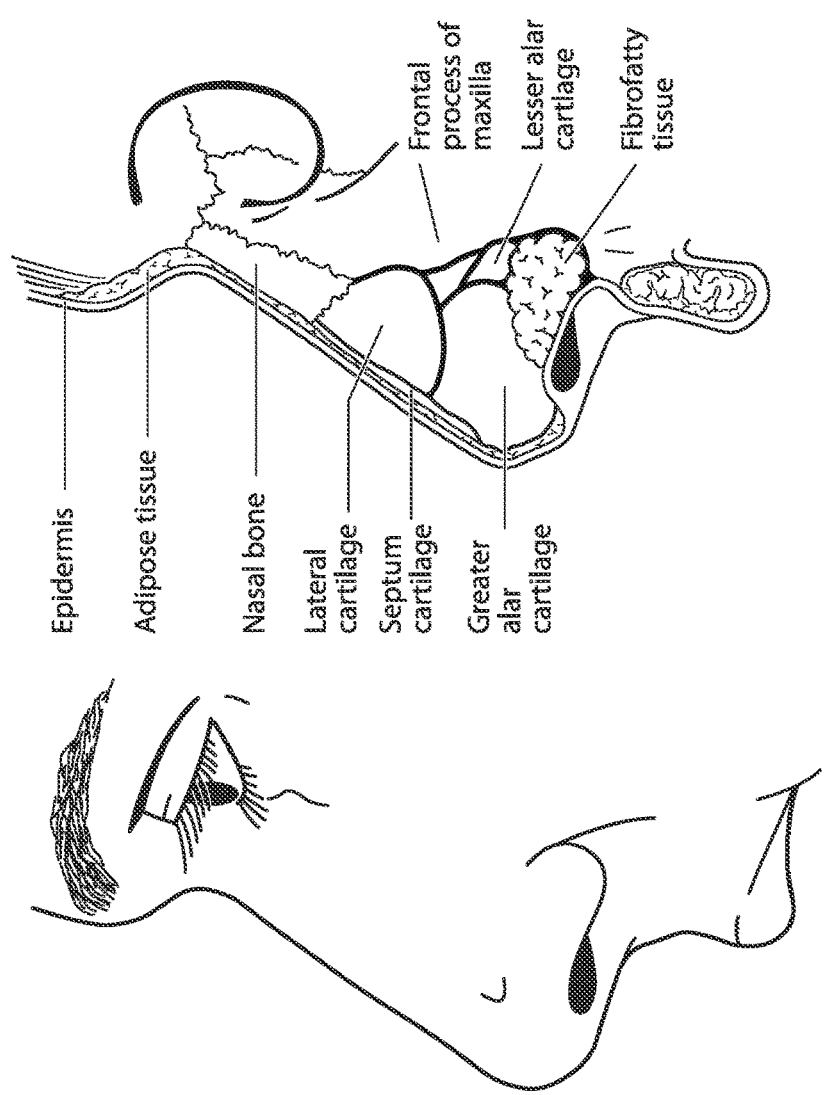
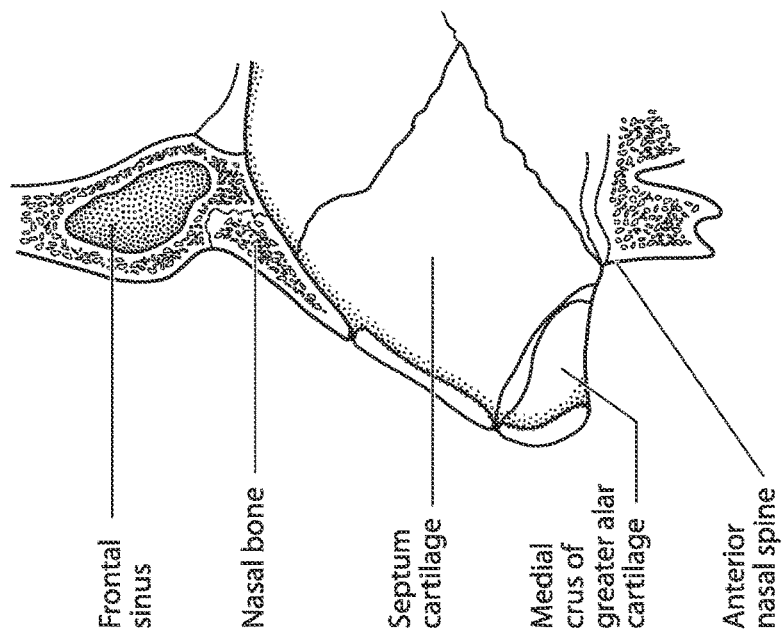
FIG. 2G
FIG. 2H
FIG. 2I

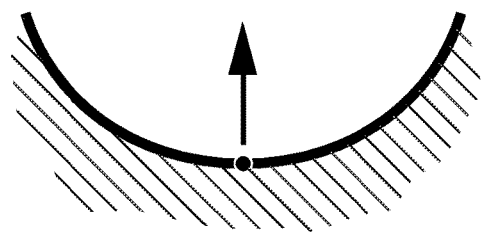
FIG. 3B — Relatively Large Positive Curvature
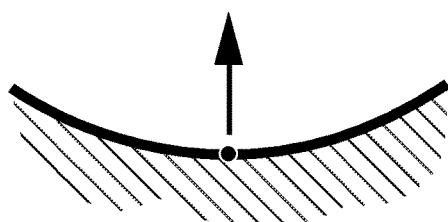
FIG. 3C — Relatively Small Positive Curvature
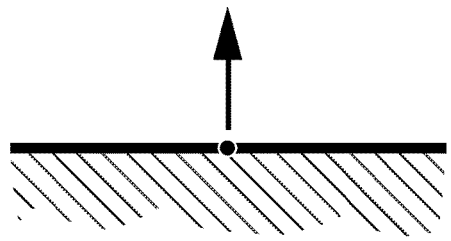
FIG. 3D — Zero Curvature
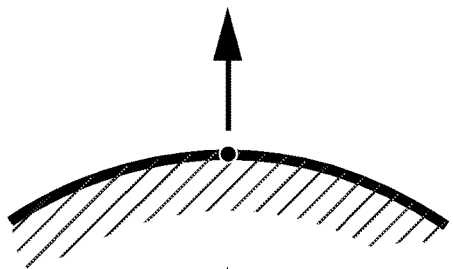
FIG. 3E — Relatively Small Negative Curvature
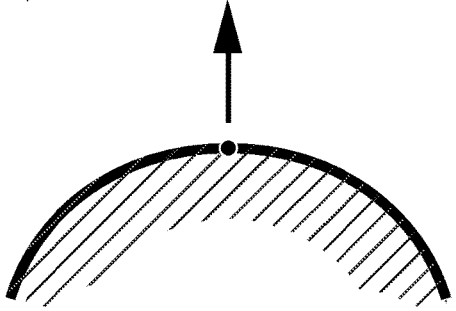
FIG. 3F — Relatively Large Negative Curvature
Copyright 2015 ResMed Limited

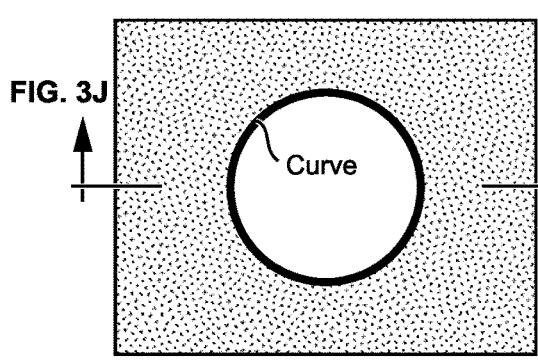
FIG. 3I
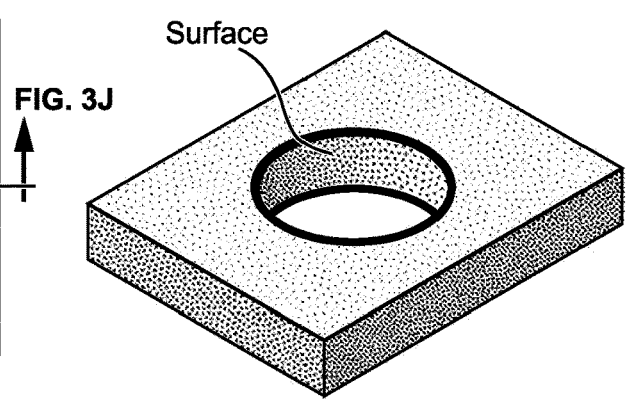
FIG. 3K
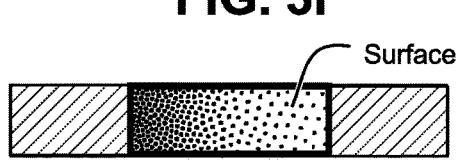
FIG. 3J
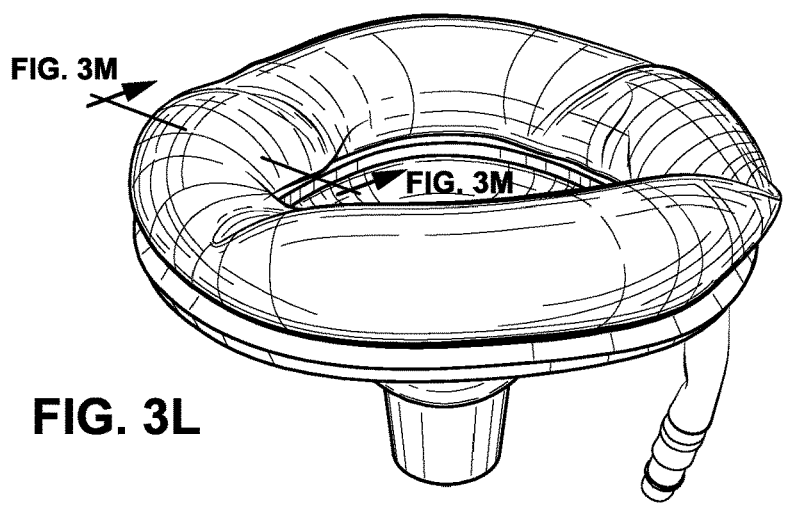
FIG. 3L
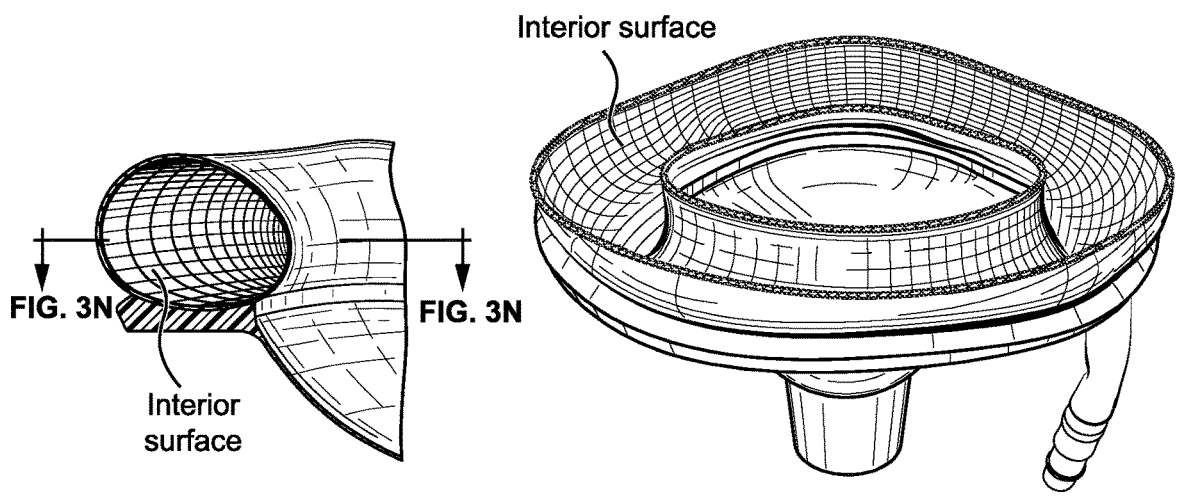
FIG. 3M     FIG. 3N
Copyright 2015 ResMed Limited

Left-hand rule          Right-hand rule
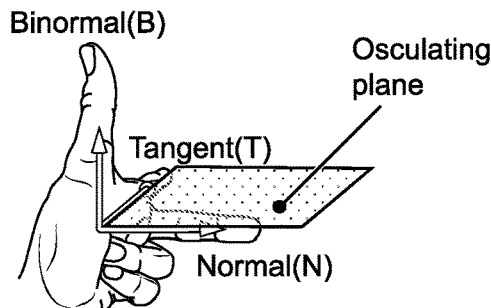
FIG. 3O
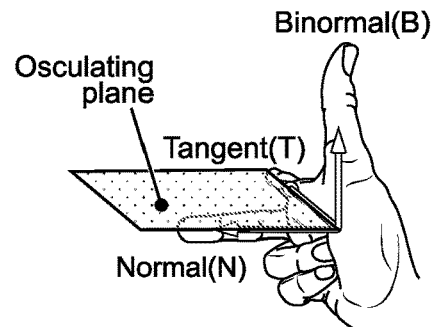
FIG. 3P
Left ear helix          Right ear helix
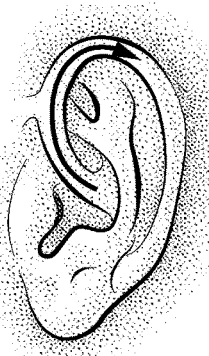
FIG. 3Q
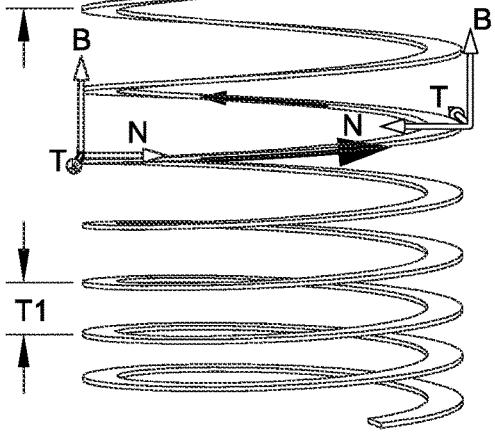
Right-hand helix
Right-hand positive
FIG. 3S
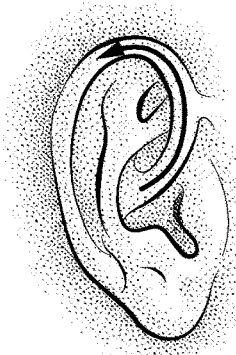
FIG. 3R
FIG. 3T
Copyright 2015 ResMed Limited

TEXTILE VENT ASSEMBLY

1 CROSS-REFERENCE TO RELATED APPLICATIONS

This application is a continuation of U.S. application Ser. No. 17/432,669, filed Aug. 20, 2021, which is the U.S. national phase of International Application No. PCT/IB2020/051474, filed Feb. 21, 2020 which designated the U.S. and claims priority to U.S. Provisional Application No. 62/808,901, filed Feb. 22, 2019, and U.S. Provisional Application No. 62/880,338, filed Jul. 30, 2019, the entire contents of each of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology relates to a patient interface comprising: a plenum chamber pressurizable to a therapeutic pressure of at least 6 cmH$_2$O above ambient air pressure, the plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, the seal-forming structure having a hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, the vent structure being sized and shaped to maintain the therapeutic pressure in the plenum chamber in use, wherein the patient interface is configured to leave the patient's mouth uncovered, or if the seal-forming structure is configured to seal around the patient's nose and mouth, the patient interface is configured to allow the patient to breath from ambient in the absence of a flow of pressurised air through the plenum chamber inlet port.

Another aspect of the present technology relates to a CPAP system for providing gas at positive pressure for respiratory therapy to a patient. The CPAP system includes an RPT device configured to supply a flow of gas at a therapeutic pressure, a patient interface forming a plenum chamber pressurizable to the therapeutic pressure, the patient interface including a seal-forming structure constructed and arranged to form a seal with a region of a patient's face surrounding an entrance to a patient's airways, an air delivery conduit configured to pass the flow of gas at the therapeutic pressure from the RPT device to the patient interface, and a vent assembly configured to provide a vent flow of gas to discharge gas exhaled by the patient from a pressurized volume to ambient. The vent assembly includes a base including at least one first orifice extending through the base to allow gas to be discharged from the pressurized volume to ambient along a primary vent flow path and at least one second orifice to allow gas to be discharged from the pressurized volume to ambient along a secondary vent flow path, a diffusing member provided to the base, and a membrane provided to the base. The diffusing member is configured and arranged such that the at least one first orifice is covered by the diffusing member so that vent flow passes through the diffusing member along the primary vent flow path and the at least one second orifice is not covered by the diffusing member so that vent flow bypasses the diffusing member along the secondary vent flow path. The membrane is structured and arranged to apportion the vent flow of gas along the primary vent flow path and the secondary vent flow path throughout respiratory therapy.

Another aspect of the present technology relates to a CPAP system for providing gas at positive pressure for respiratory therapy to a patient. The CPAP system includes an RPT device configured to supply a flow of gas at a therapeutic pressure, a patient interface forming a plenum chamber pressurizable to the therapeutic pressure, the patient interface including a seal-forming structure constructed and arranged to form a seal with a region of a patient's face surrounding an entrance to a patient's airways, an air delivery conduit configured to pass the flow of gas at the therapeutic pressure from the RPT device to the patient interface, and a vent assembly configured to provide a vent flow of gas to discharge gas exhaled by the patient from a pressurized volume to ambient. The vent assembly includes a base including at least one first orifice extending through the base to allow gas to be discharged from the pressurized volume to ambient along a primary vent flow path and at least one second orifice to allow gas to be discharged from the pressurized volume to ambient along a secondary vent flow path, a diffusing member provided to the base, and a vent component provided to the at least one second orifice of the base, the vent component including a plurality of vent orifices. The diffusing member is configured and arranged such that the at least one first orifice is covered by the diffusing member along the primary vent flow path and the at least one second orifice is not covered by the diffusing member along the secondary vent flow path. The vent component comprises an expanding polymer material structured and arranged to regulate the vent flow of gas along the secondary vent flow path throughout respiratory therapy.

Another aspect of the present technology relates to a CPAP system for providing gas at positive pressure for respiratory therapy to a patient. The CPAP system includes an RPT device configured to supply a flow of gas at a therapeutic pressure, a patient interface forming a plenum chamber pressurizable to the therapeutic pressure, the patient interface including a seal-forming structure constructed and arranged to form a seal with a region of a patient's face surrounding an entrance to a patient's airways, an air delivery conduit configured to pass the flow of gas at the therapeutic pressure from the RPT device to the patient interface, and a vent assembly configured to provide a vent flow of gas to discharge gas exhaled by the patient from a pressurized volume to ambient. The vent assembly includes a vent member comprising a textile material and a plurality of vent holes to allow gas to be discharged from the pressurized volume to ambient, a diffusing member comprising a textile material and configured and arranged such that the plurality of vent holes are covered by the diffusing member, and a support structure to support the diffusing member in spaced relation from the vent member. The support structure includes an opening to allow gas to be discharged along a primary vent flow path and lateral openings to allow gas to be discharged along a secondary vent flow path, and the diffusing member is supported by the support structure such that the opening is covered by the diffusing member so that vent flow passes through the diffusing member along the primary vent flow path and the lateral openings are not covered by the diffusing member so that vent flow bypasses the diffusing member along the secondary vent flow path.

Another aspect of the present technology relates to a vent assembly including a base, diffusing member, a membrane, and/or a vent component.

Another aspect of the present technology relates to a vent assembly including a base including at least one first orifice extending through the base to allow gas to be discharged from a pressurized volume to ambient along a primary vent flow path and at least one second orifice to allow gas to be discharged from the pressurized volume to ambient along a secondary vent flow path, a diffusing member provided to the base, and a membrane provided to the base. The diffusing member is configured and arranged such that the at least one first orifice is covered by the diffusing member so that vent flow passes through the diffusing member along the primary vent flow path and the at least one second orifice is not covered by the diffusing member so that vent flow bypasses the diffusing member along the secondary vent flow path. The membrane is structured and arranged to apportion the vent flow of gas along the primary vent flow path and the secondary vent flow path throughout respiratory therapy.

Another aspect of the present technology relates to a vent assembly including a base including at least one first orifice extending through the base to allow gas to be discharged from a pressurized volume to ambient along a primary vent flow path and at least one second orifice to allow gas to be discharged from the pressurized volume to ambient along a secondary vent flow path, a diffusing member provided to the base, and a vent component provided to the at least one second orifice of the base, the vent component including a plurality of vent orifices. The diffusing member is configured and arranged such that the at least one first orifice is covered by the diffusing member along the primary vent flow path and the at least one second orifice is not covered by the diffusing member along the secondary vent flow path. The vent component comprises an expanding polymer material structured and arranged to regulate the vent flow of gas along the secondary vent flow path throughout respiratory therapy.

Another aspect of the present technology relates to a vent assembly including a textile vent member, a textile diffusing member and/or a support structure.

Another aspect of the present technology relates to a vent assembly including a vent member comprising a textile material and including a plurality of vent holes to allow gas to be discharged from a pressurized volume to ambient, a diffusing member comprising a textile material and configured and arranged such that the plurality of vent holes are covered by the diffusing member, and a support structure to support the diffusing member in spaced relation from the vent member. The support structure includes an opening to allow gas to be discharged along a primary vent flow path and lateral openings to allow gas to be discharged along a secondary vent flow path, and the diffusing member is supported by the support structure such that the opening is covered by the diffusing member so that vent flow passes through the diffusing member along the primary vent flow path and the lateral openings are not covered by the diffusing member so that vent flow bypasses the diffusing member along the secondary vent flow path.

Another aspect of the present technology relates to a vent assembly configured to provide a vent flow of gas to discharge gas from a pressurized volume to ambient. The vent assembly includes at least one first orifice to allow gas to be discharged from the pressurized volume to ambient along a primary vent flow path, at least one second orifice to allow gas to be discharged from the pressurized volume to ambient along a secondary vent flow path, a diffusing member configured and arranged such that the at least one first orifice is covered by the diffusing member so that vent flow passes through the diffusing member along the primary vent flow path and the at least one second orifice is not covered by the diffusing member so that vent flow bypasses the diffusing member along the secondary vent flow path, and a membrane structured and arranged to apportion the vent flow of gas along the primary vent flow path and the secondary vent flow path. In an example, the vent assembly is provided to a patient interface. In an example, the vent assembly is provided to an air delivery conduit.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
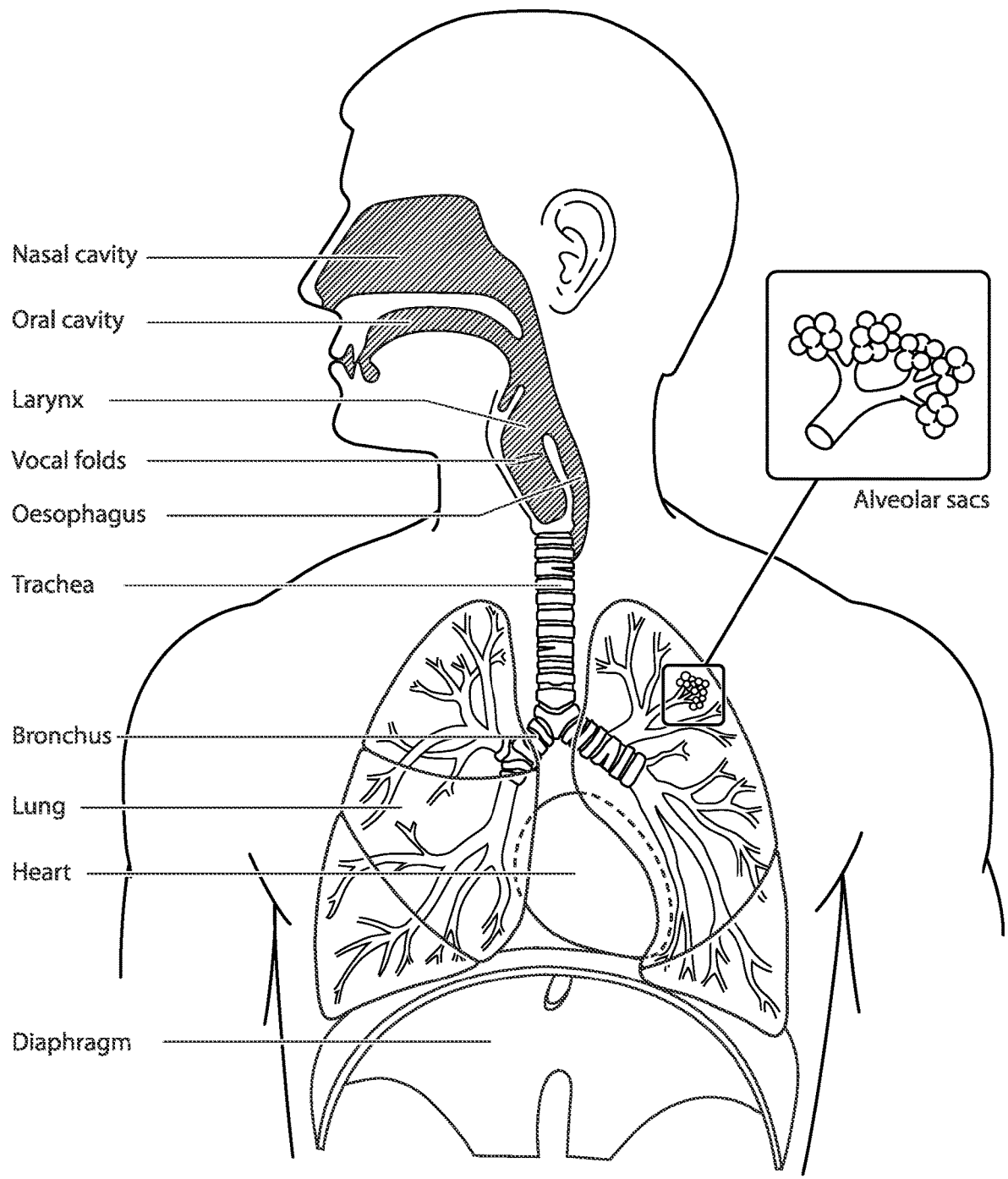
FIG. 2A shows an overview of a human respiratory system including the nasal and oral cavities, the larynx, vocal folds, oesophagus, trachea, bronchus, lung, alveolar sacs, heart and diaphragm.
Figure 2B:
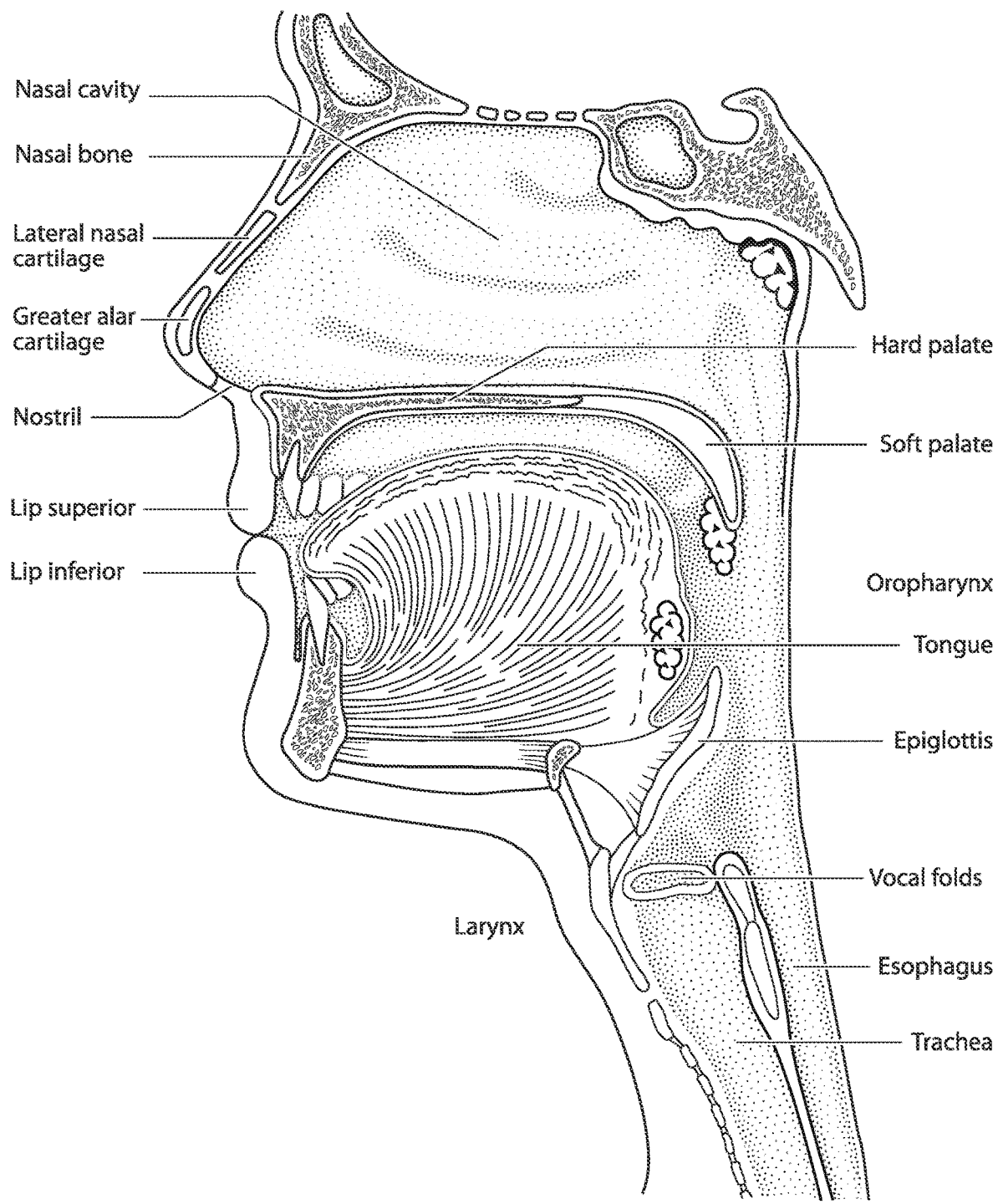
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
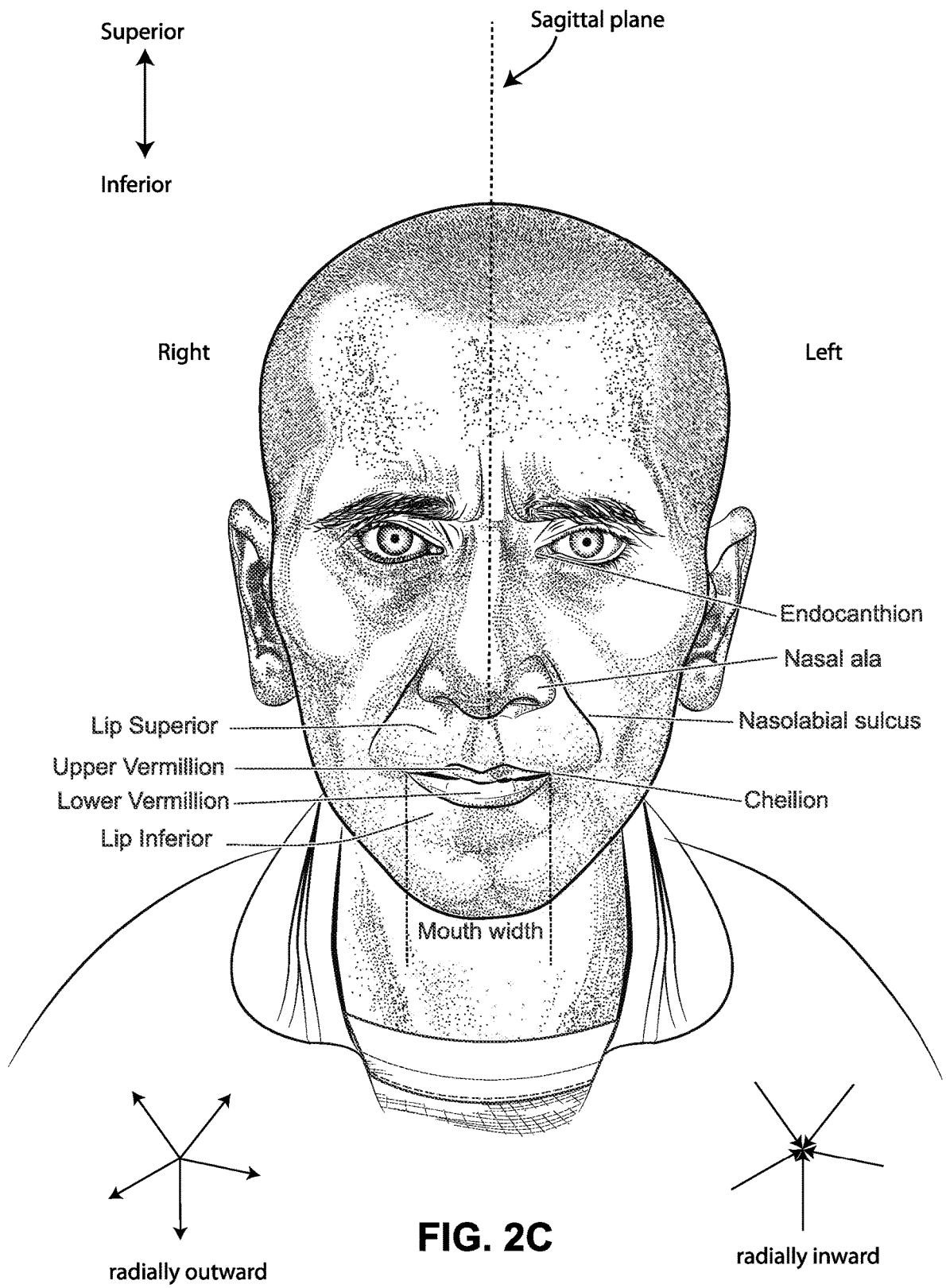
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
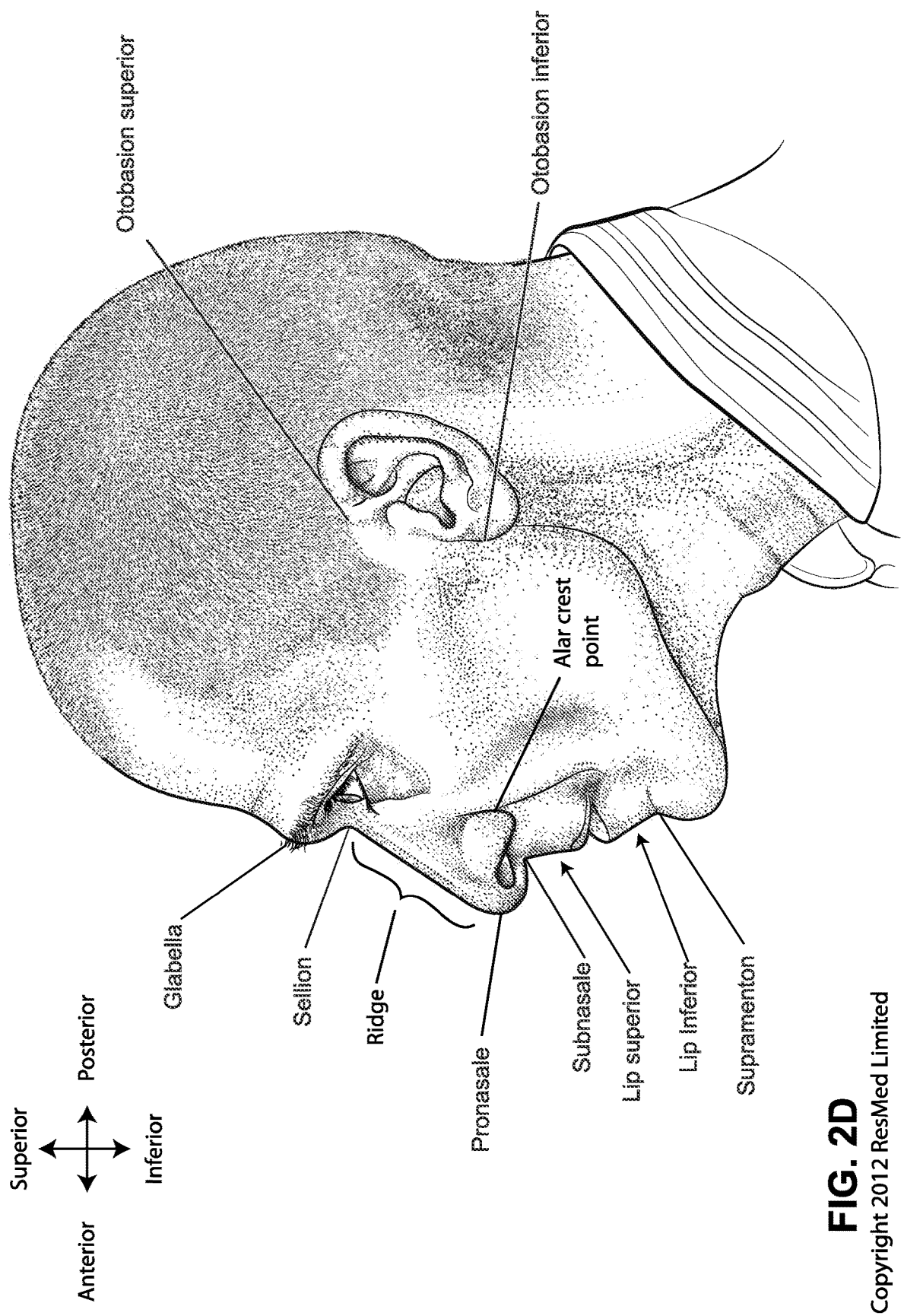
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
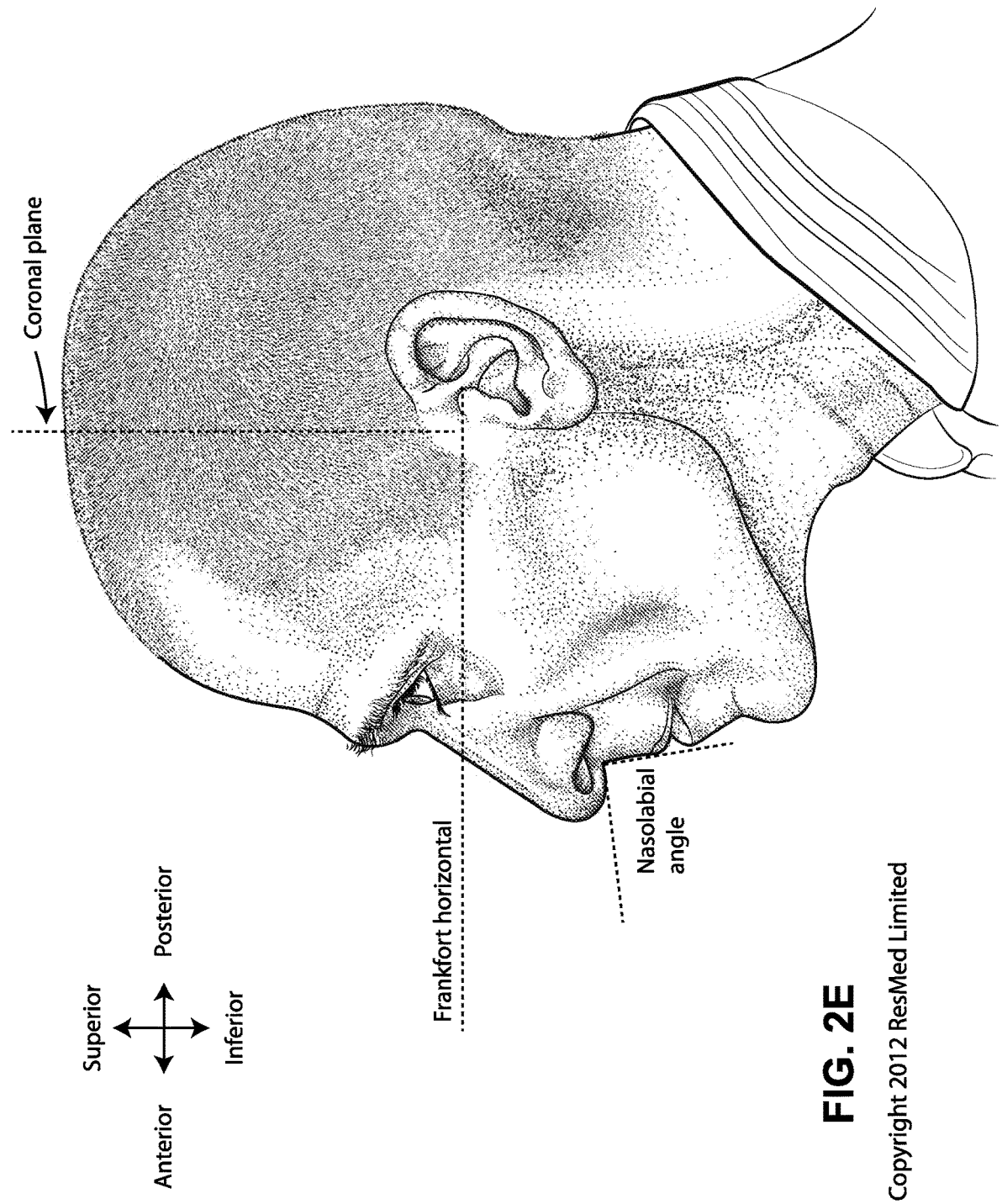

FIG. 2E is a further side view of a head. The approximate locations of the Frankfort horizontal and nasolabial angle are indicated. The coronal plane is also indicated.

Figure 2F:
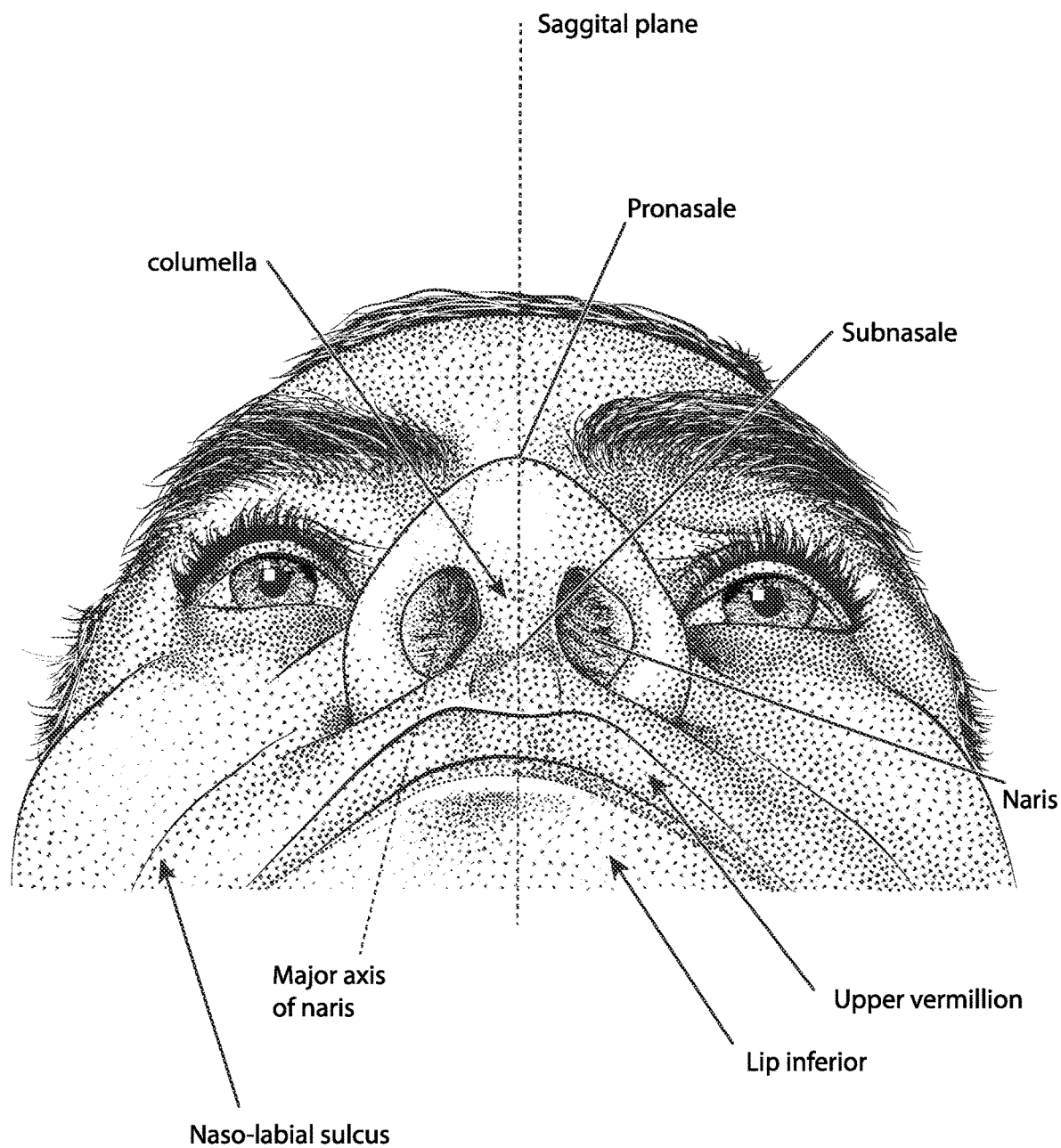

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
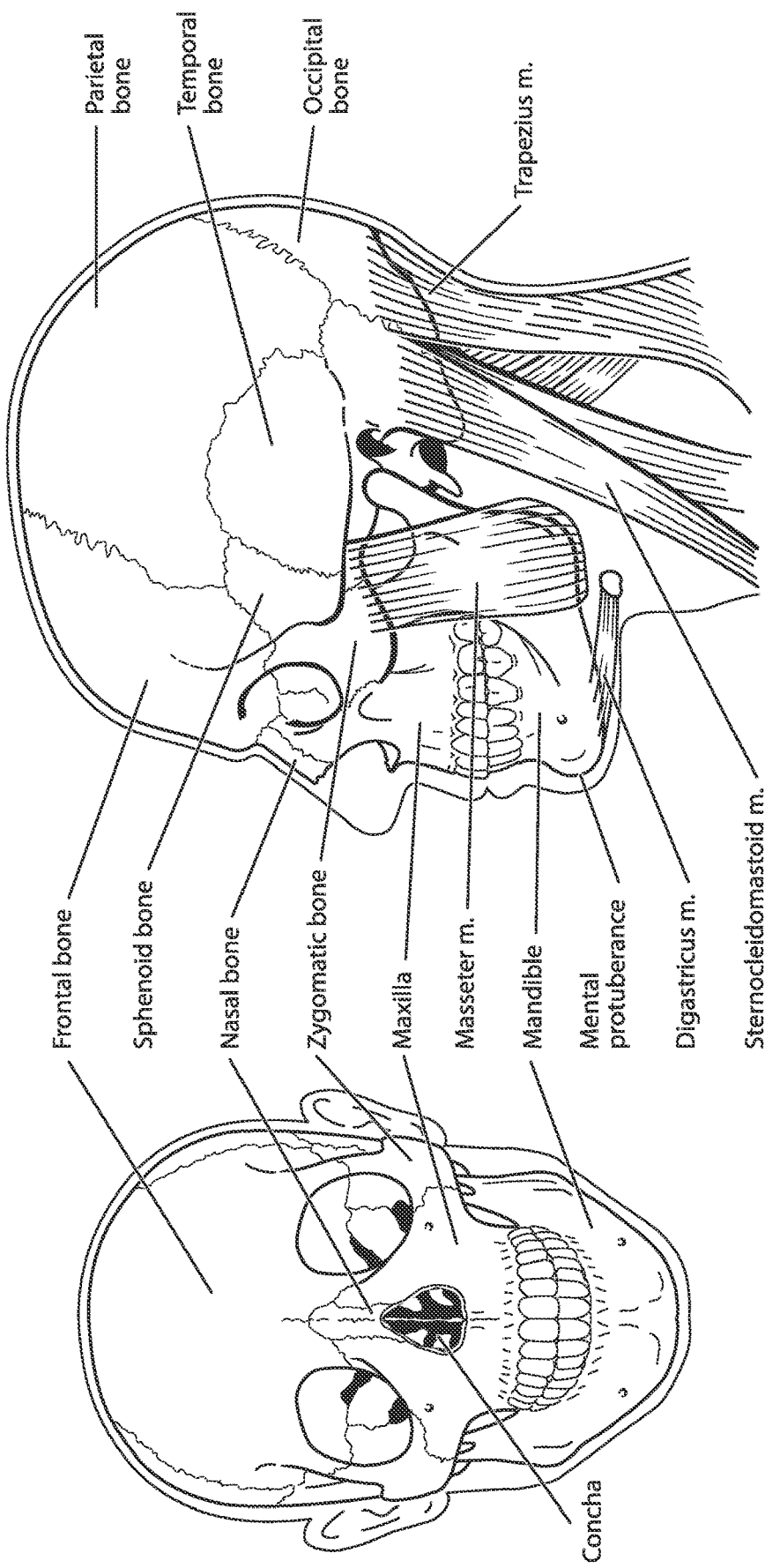

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
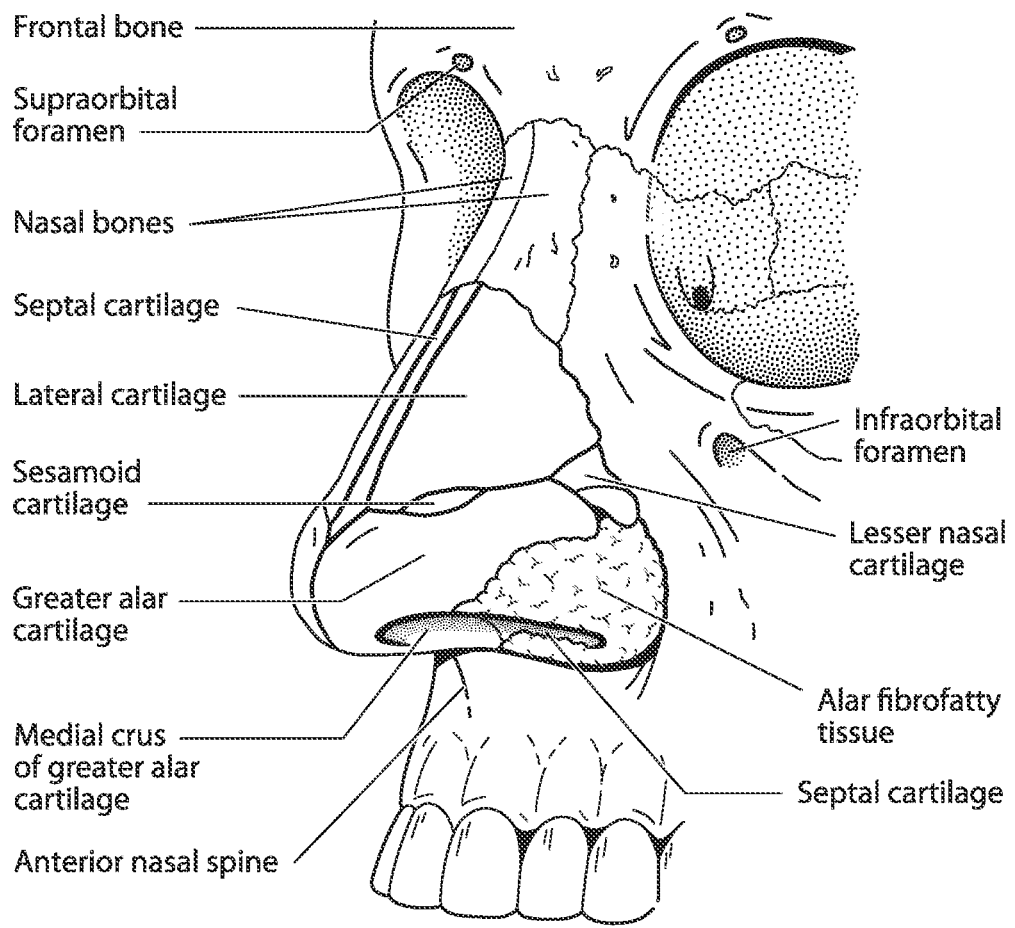

FIG. 2L shows an anterolateral view of a nose.

4.3 Patient Interface

Figure 3A:
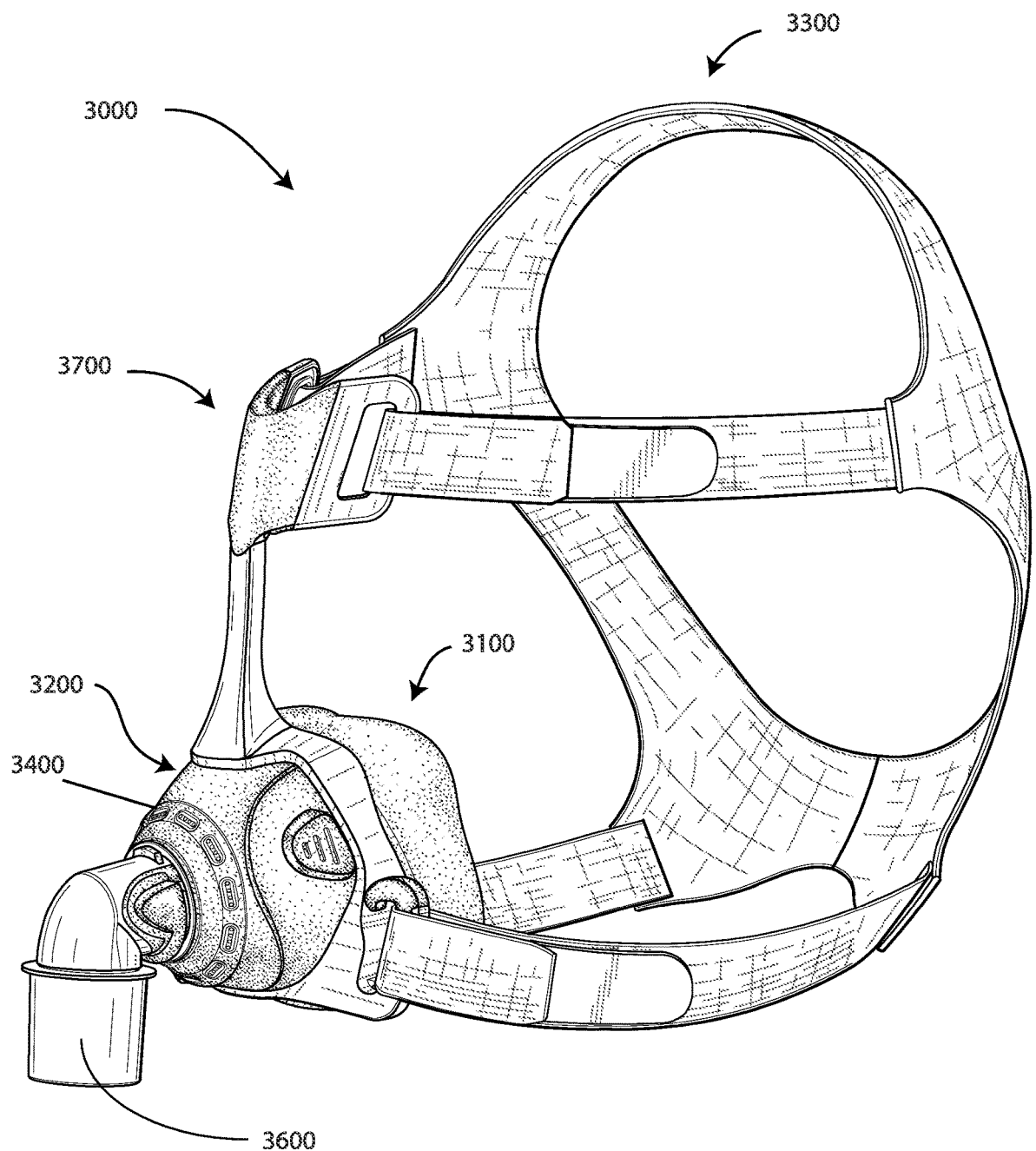

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
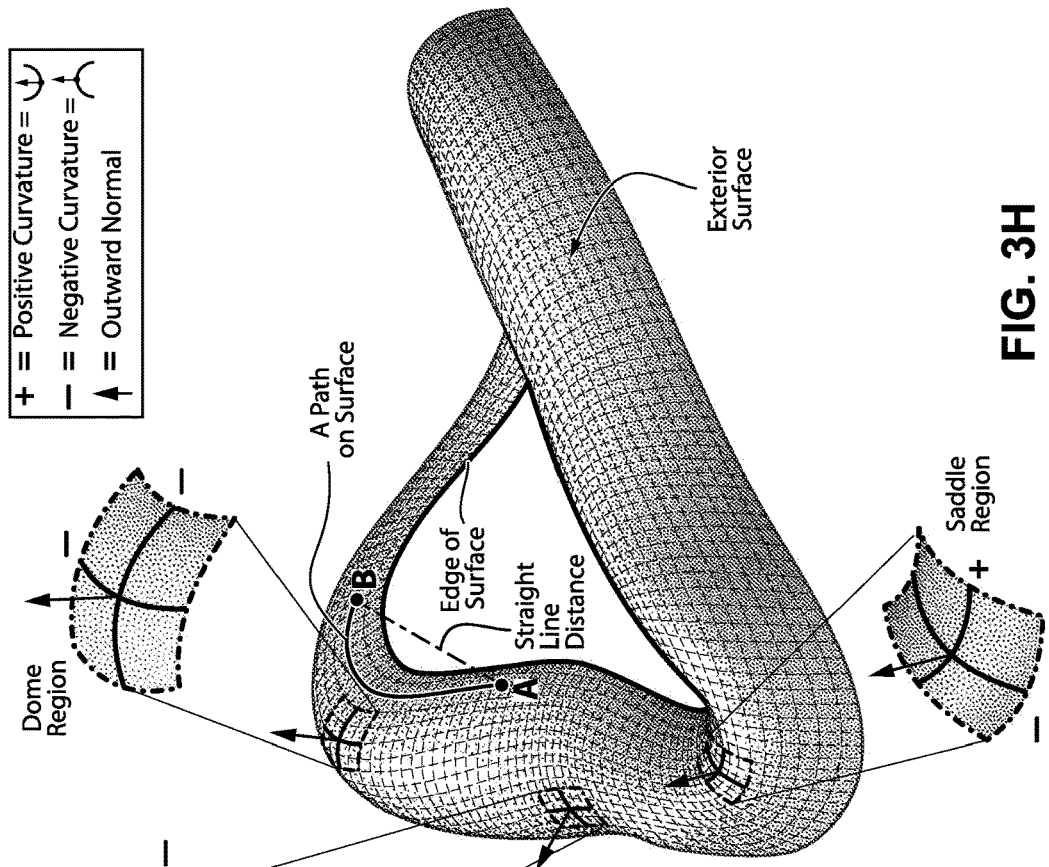
Figure 3G:
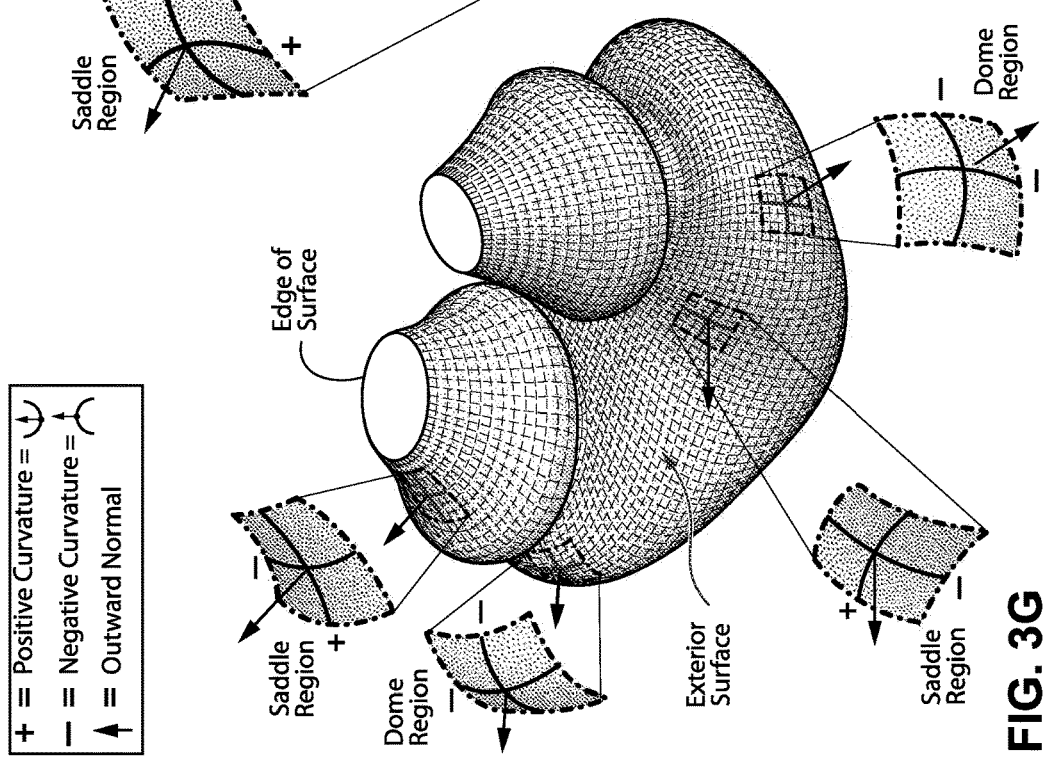

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
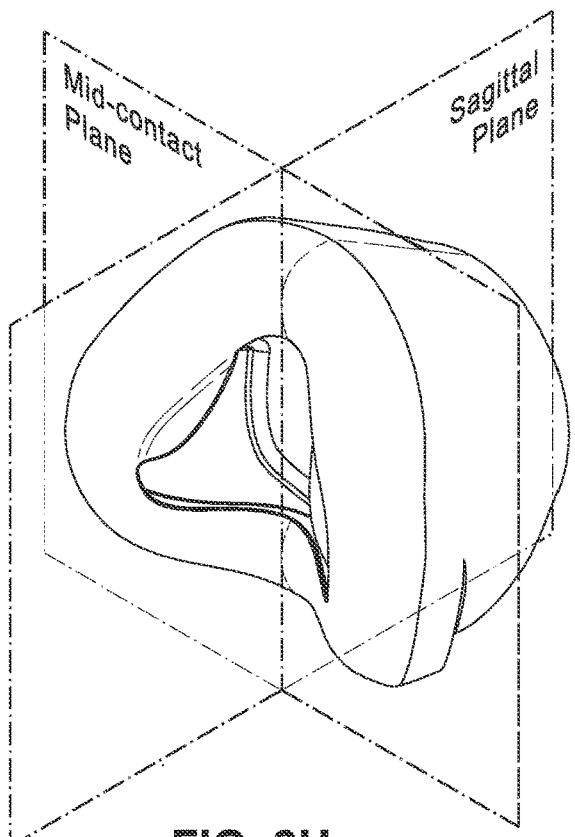

FIG. 3U shows a view of a plenum chamber 3200 showing a sagittal plane and a mid-contact plane.

Figure 3V:
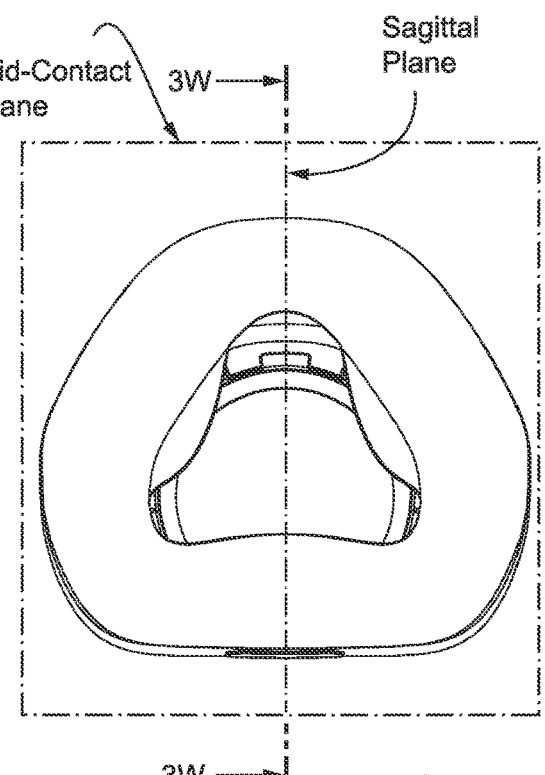

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
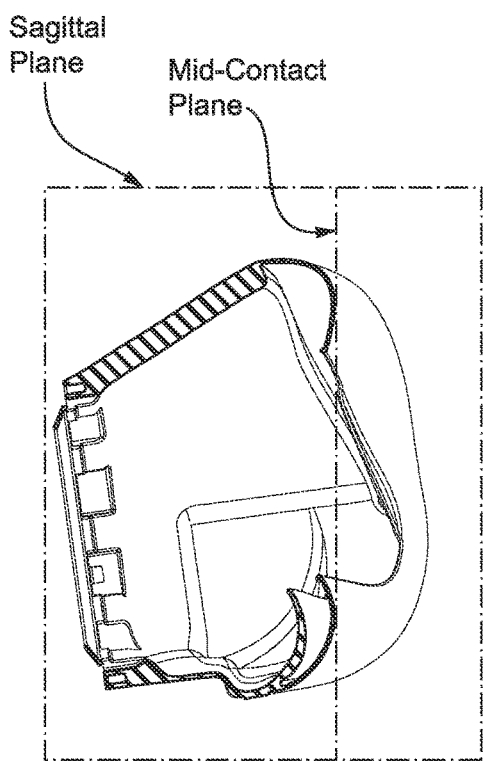

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
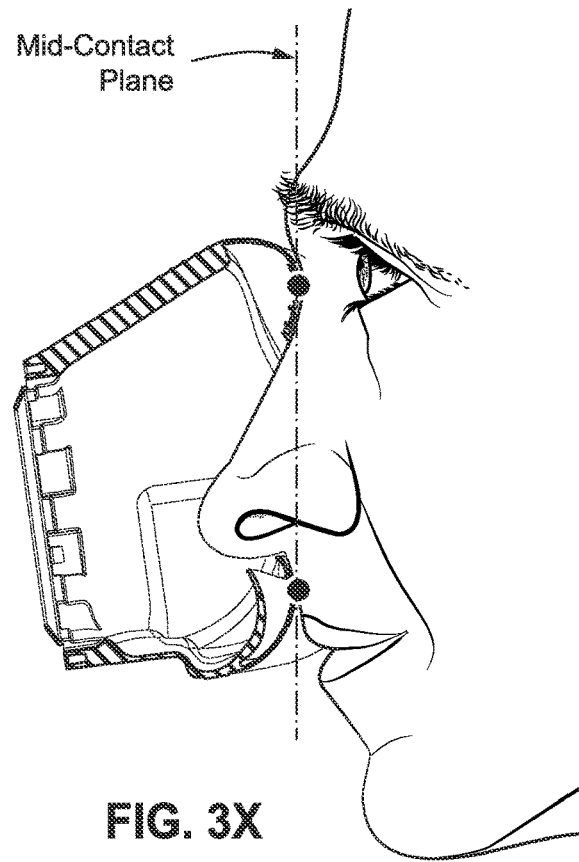

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 Vent Assembly

Figure 4A:
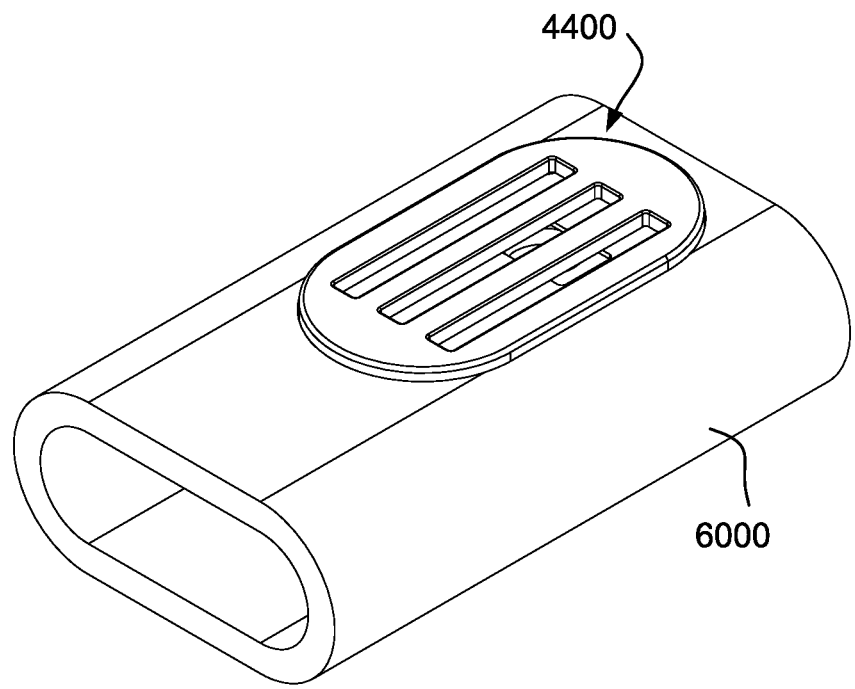

FIG. 4A is a perspective view of a vent assembly provided to an air delivery conduit according to an example of the present technology.

Figure 4B:
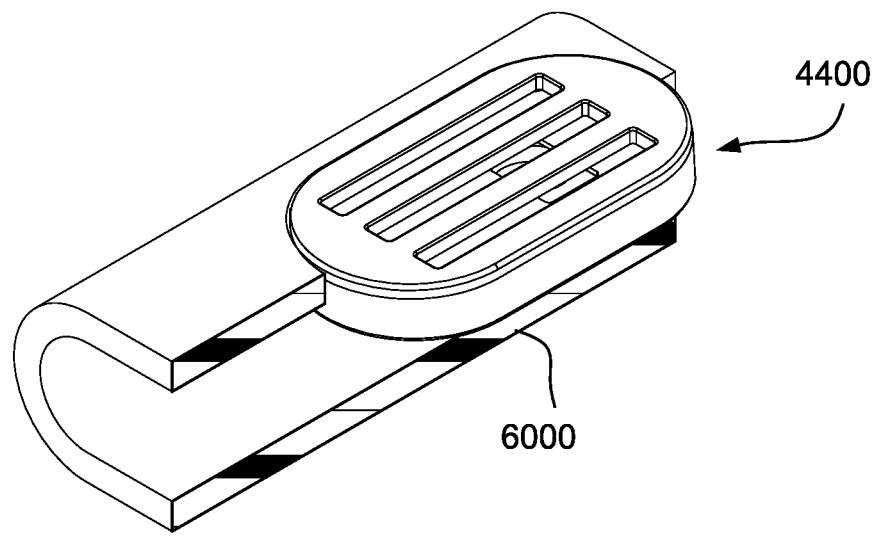

FIG. 4B is a cross-sectional view of a vent assembly provided to an air delivery conduit according to an example of the present technology.

Figure 4C:
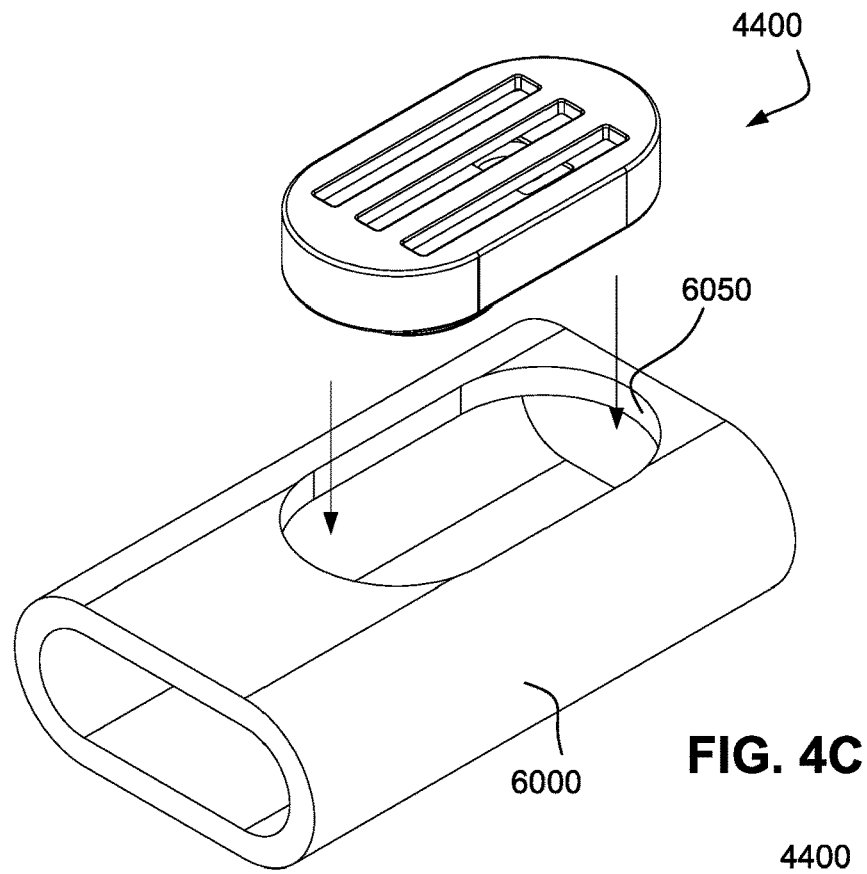

FIG. 4C is an exploded of a vent assembly and air delivery conduit according to an example of the present technology.

Figure 4D:
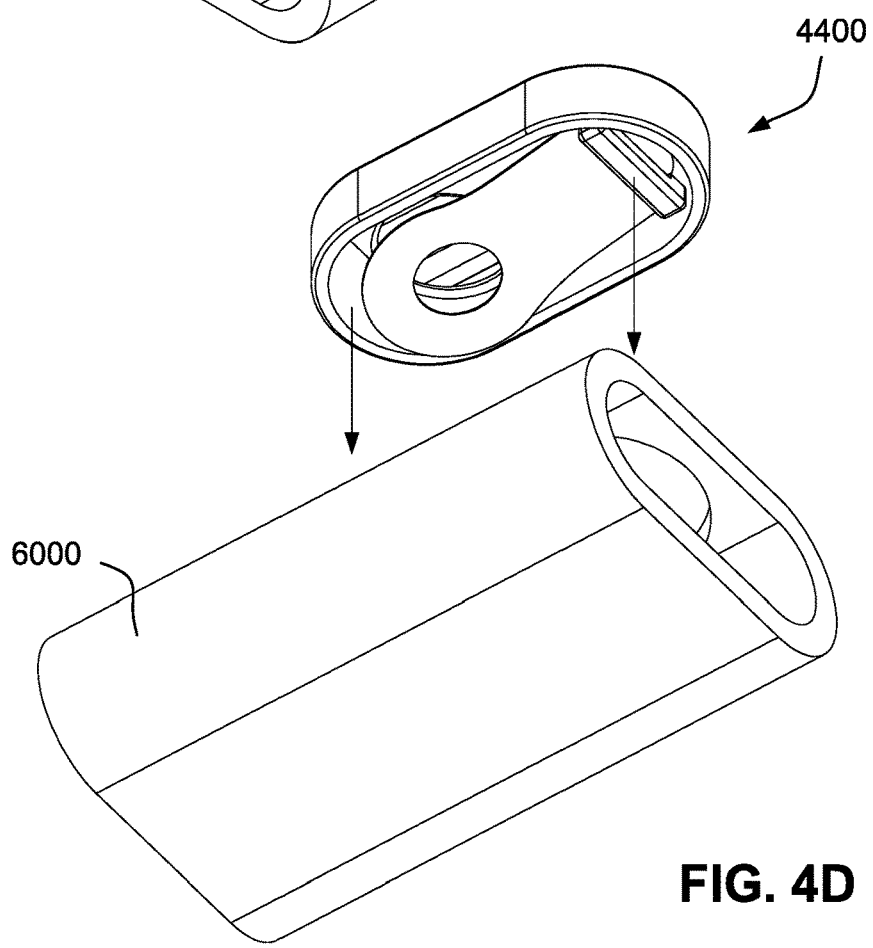

FIG. 4D is another exploded view of a vent assembly and air delivery conduit according to an example of the present technology.

Figure 4E:
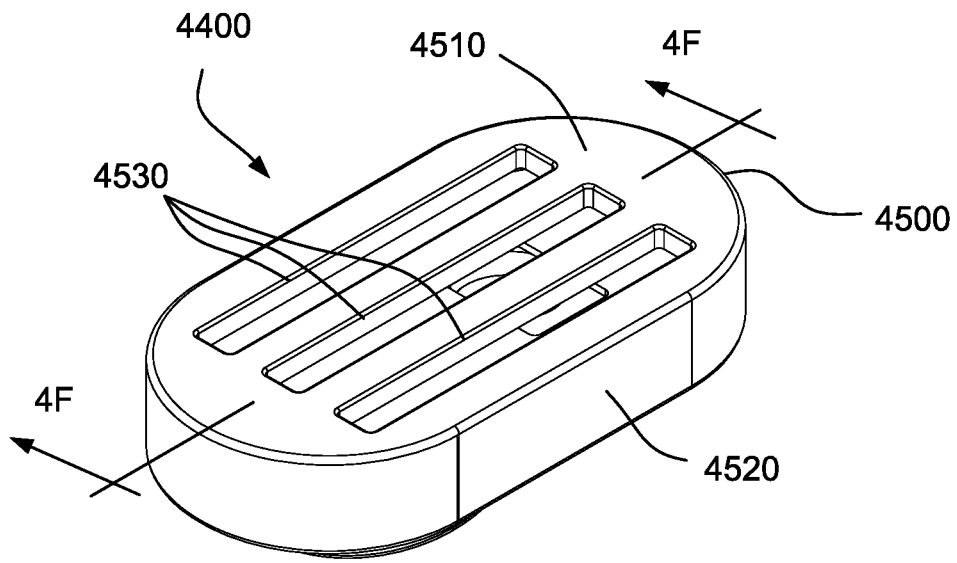

FIG. 4E is a perspective view of a vent assembly according to an example of the present technology.

Figure 4F:
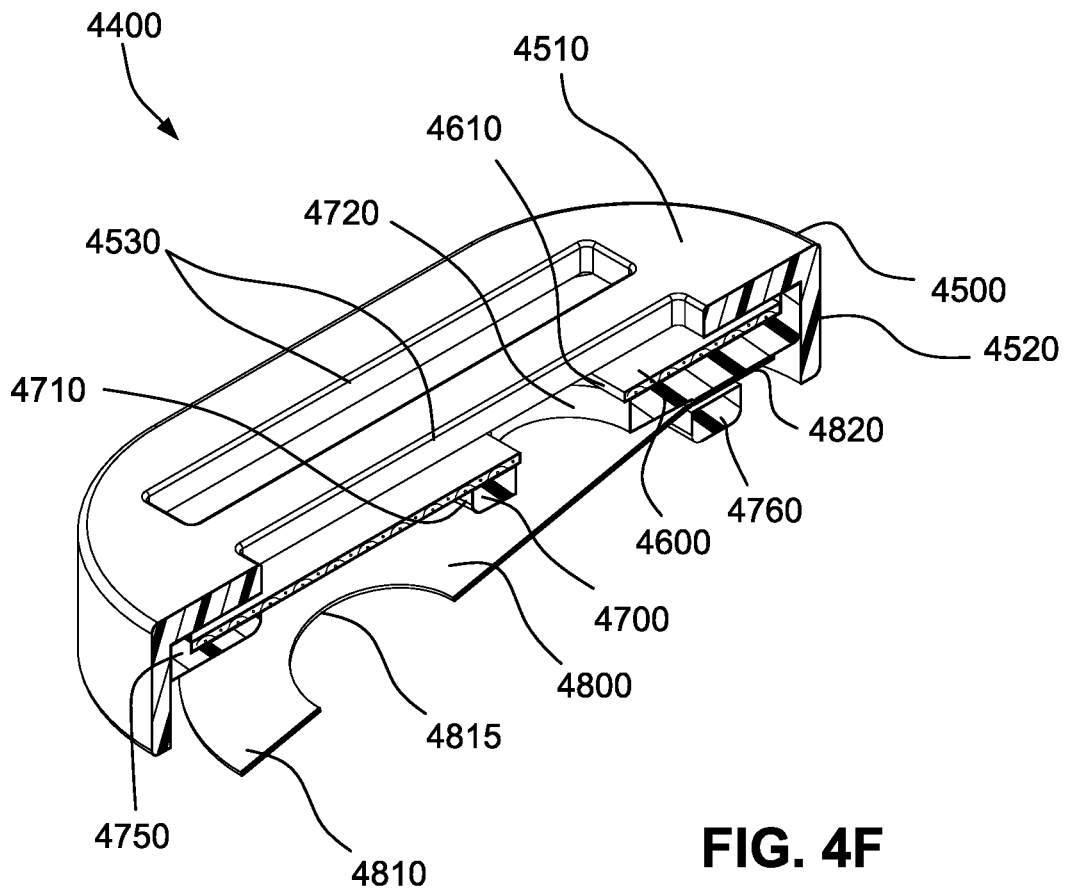

FIG. 4F is a cross-sectional view of the vent assembly of FIG. 4E.

Figure 4G:
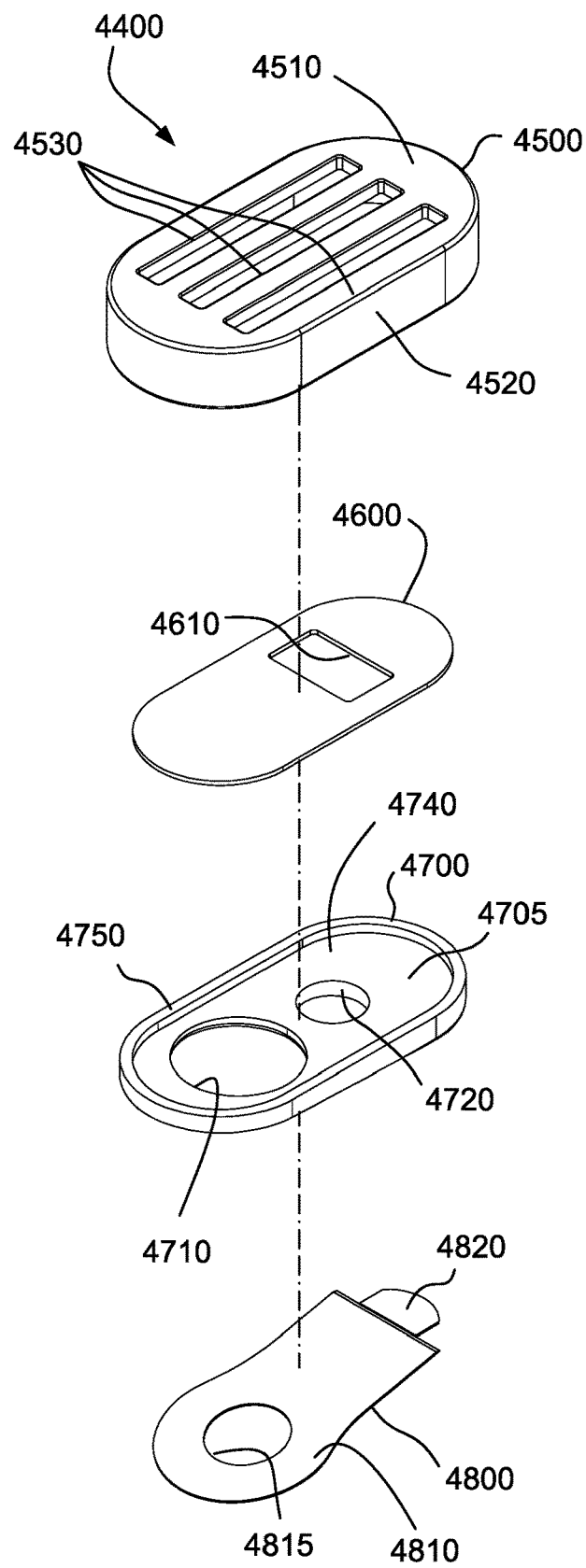

FIG. 4G is an exploded view of the vent assembly of FIG. 4E.

Figure 4H:
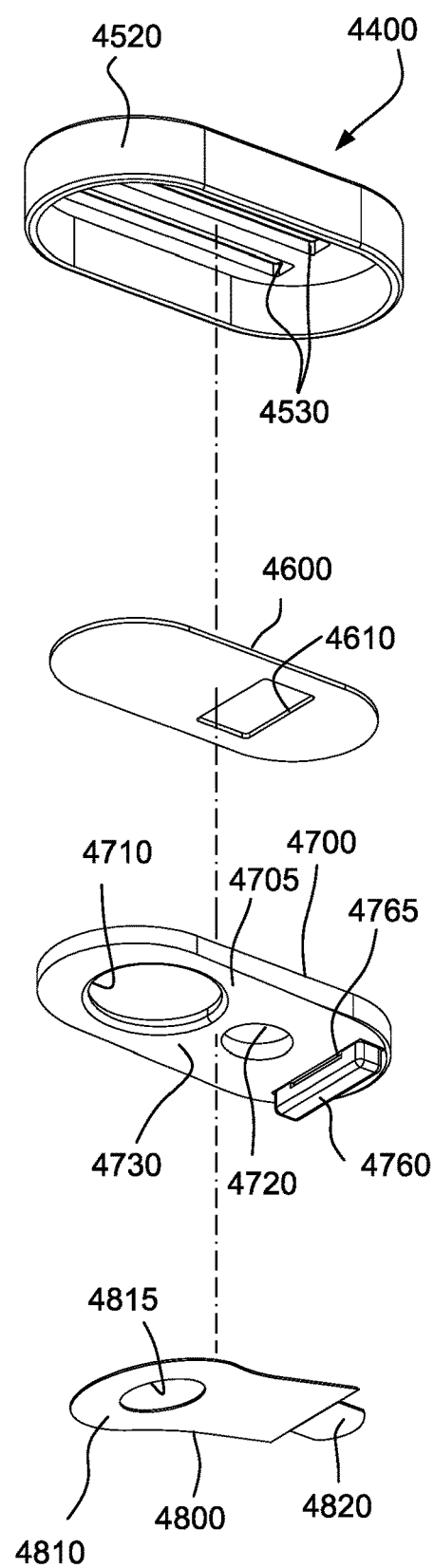

FIG. 4H is another exploded view of the vent assembly of FIG. 4E.

Figure 4I:
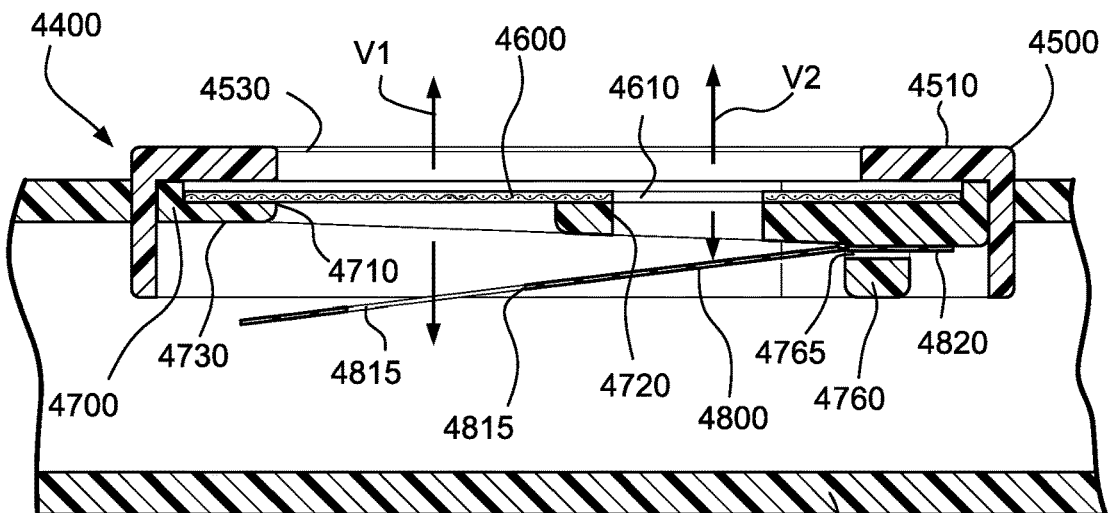

FIG. 4I is a cross-sectional view showing air passing through the vent assembly of FIG. 4E when there is no air pressure or low pressure in the air delivery conduit and the textile material is not blocked according to an example of the present technology.

Figure 4J:
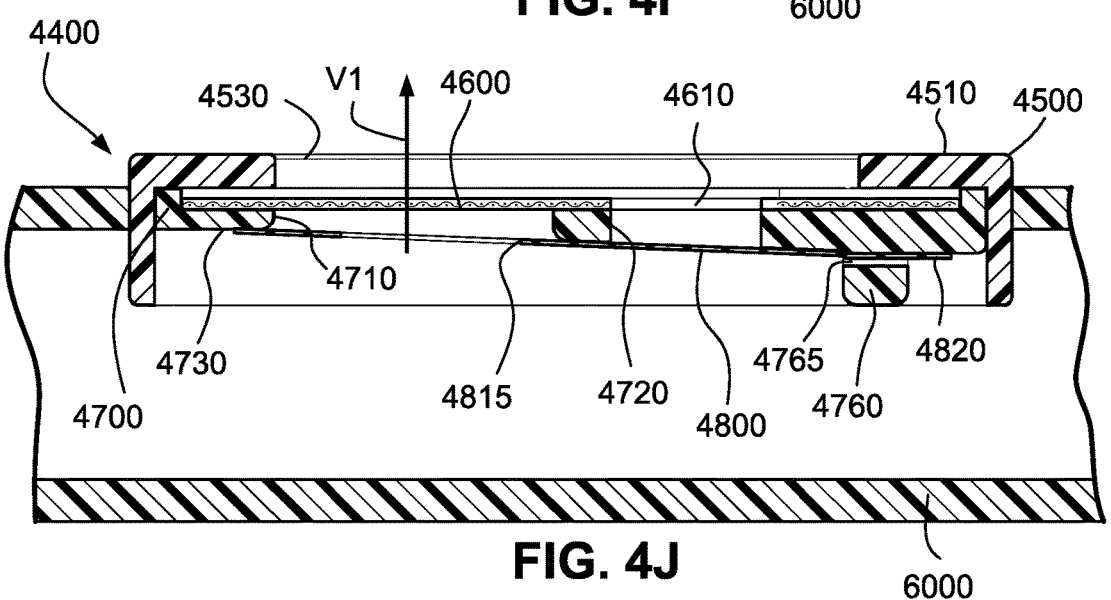

FIG. 4J is a cross-sectional view showing air passing through the vent assembly of FIG. 4E when there is air pressure in the air delivery conduit and the textile material is not blocked according to an example of the present technology.

Figure 4K:
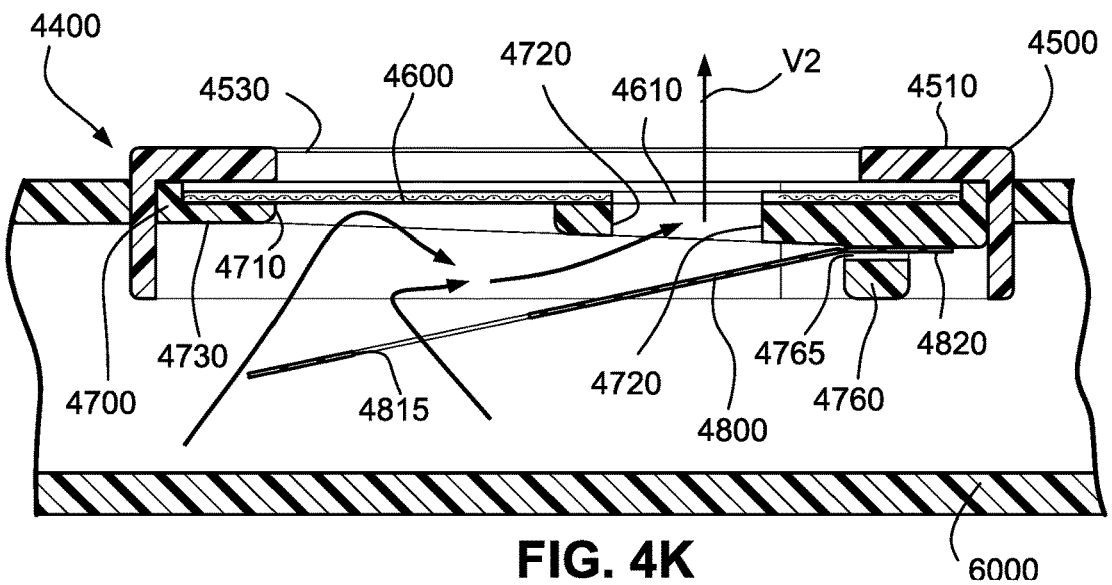

FIG. 4K is a cross-sectional view showing air passing through the vent assembly of FIG. 4E when there is air pressure in the air delivery conduit and the textile material is blocked according to an example of the present technology.

Figure 5A:
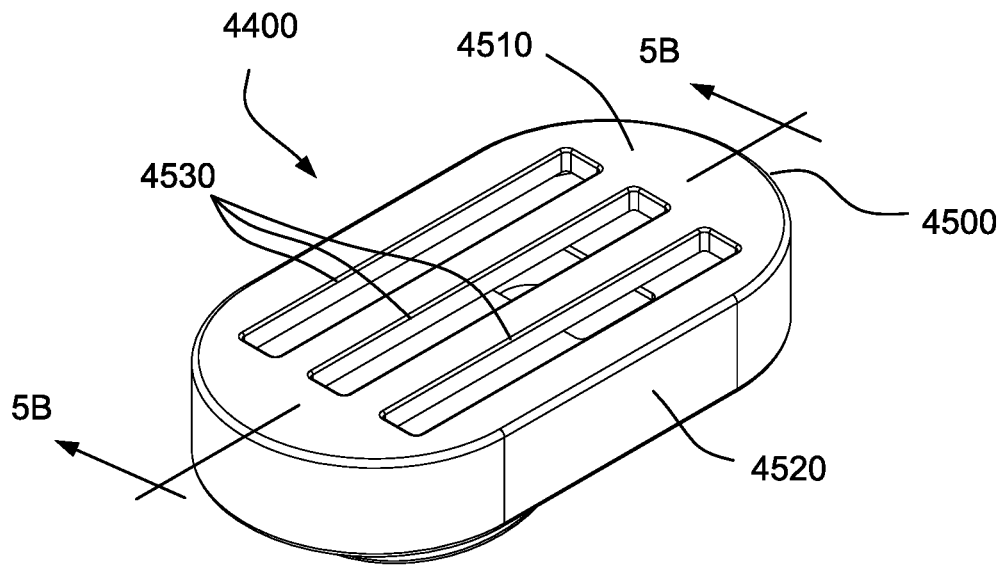

FIG. 5A is a perspective view of a vent assembly according to an example of the present technology.

Figure 5B:
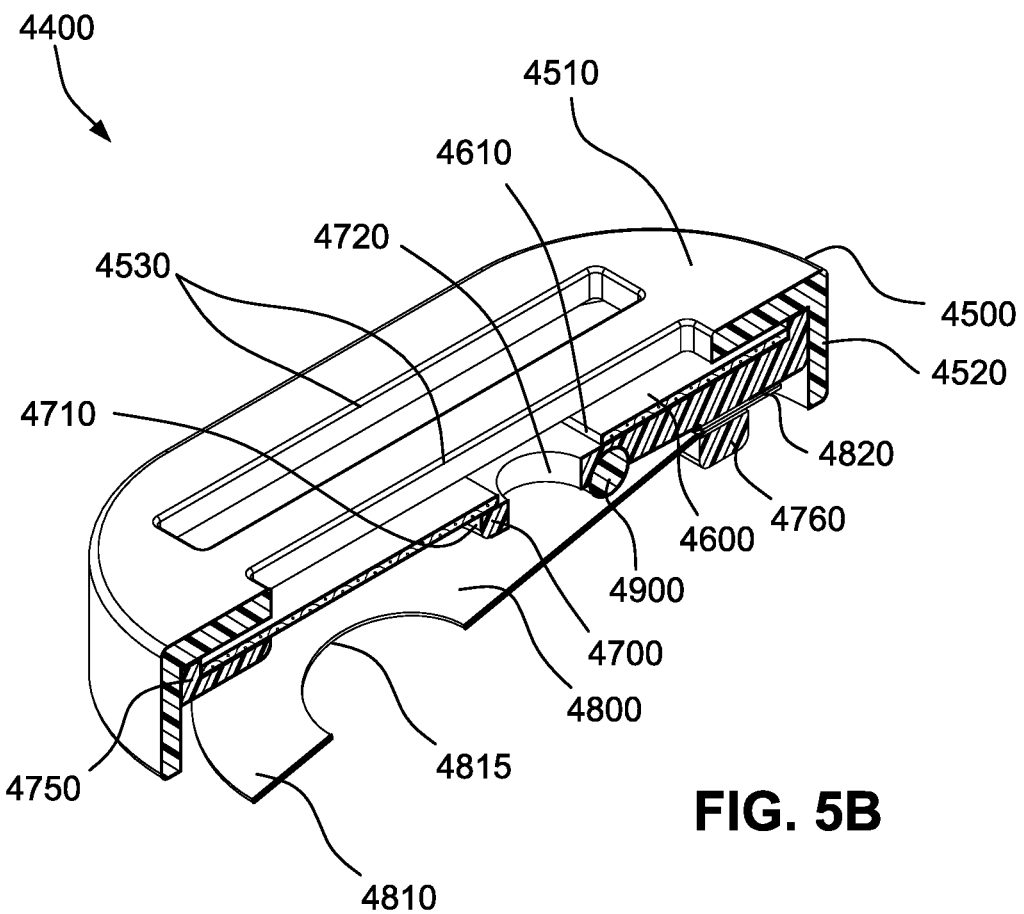

FIG. 5B is a cross-sectional view of the vent assembly of FIG. 5A.

Figure 5C:
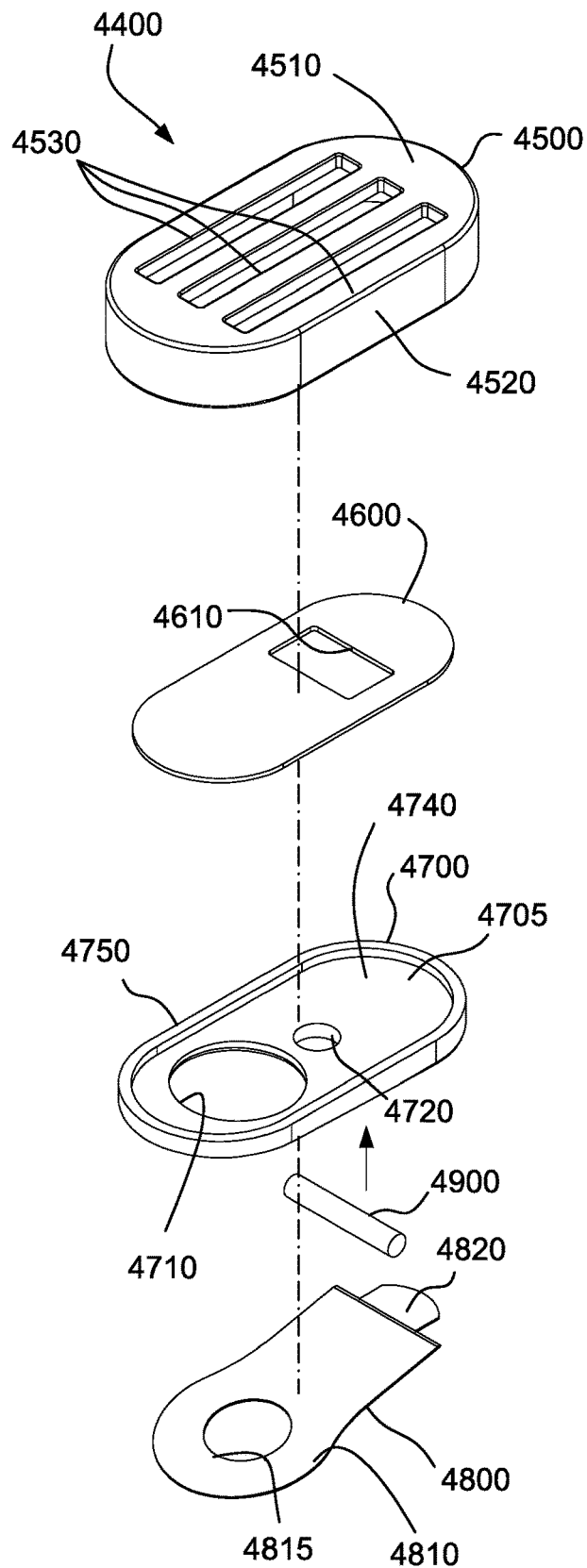

FIG. 5C is an exploded view of the vent assembly of FIG. 5A.

Figure 5D:
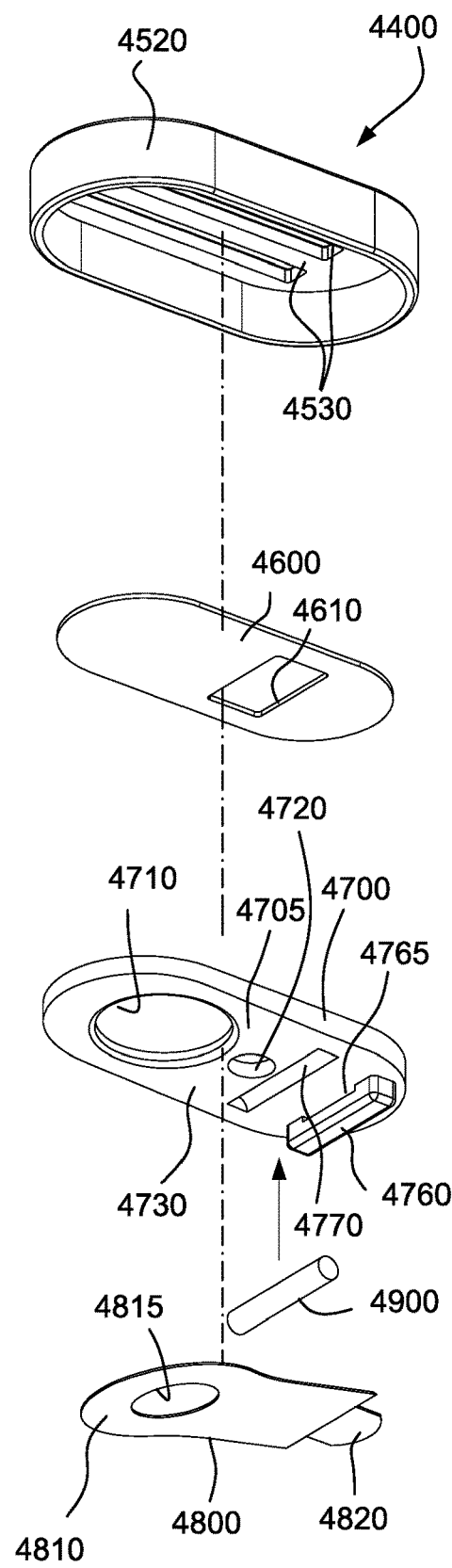

FIG. 5D is another exploded view of the vent assembly of FIG. 5A.

Figure 5E:
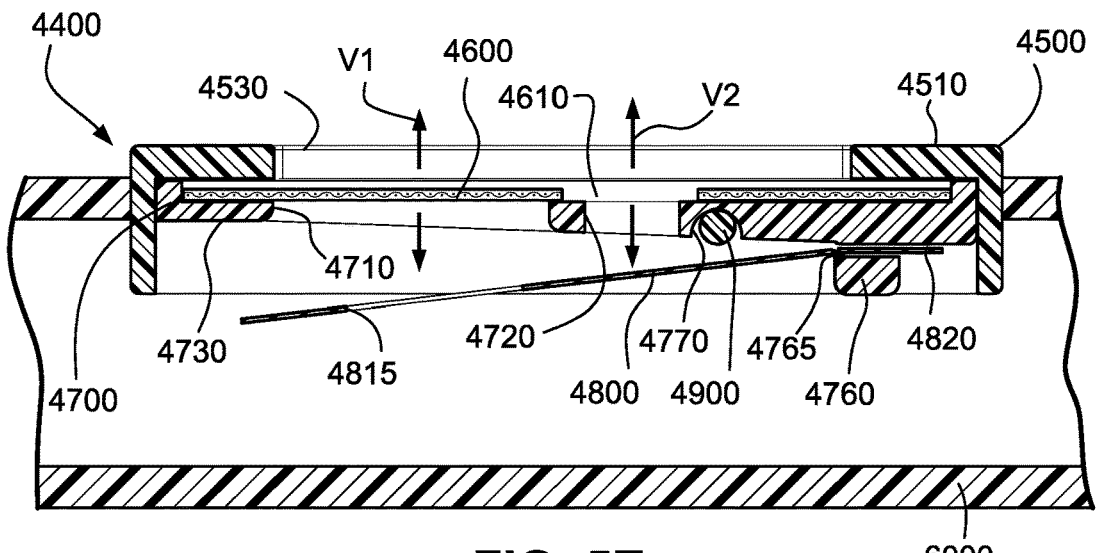

FIG. 5E is a cross-sectional view showing air passing through the vent assembly of FIG. 5A when there is no air pressure or low pressure in the air delivery conduit and the textile material is not blocked according to an example of the present technology.

Figure 5F:
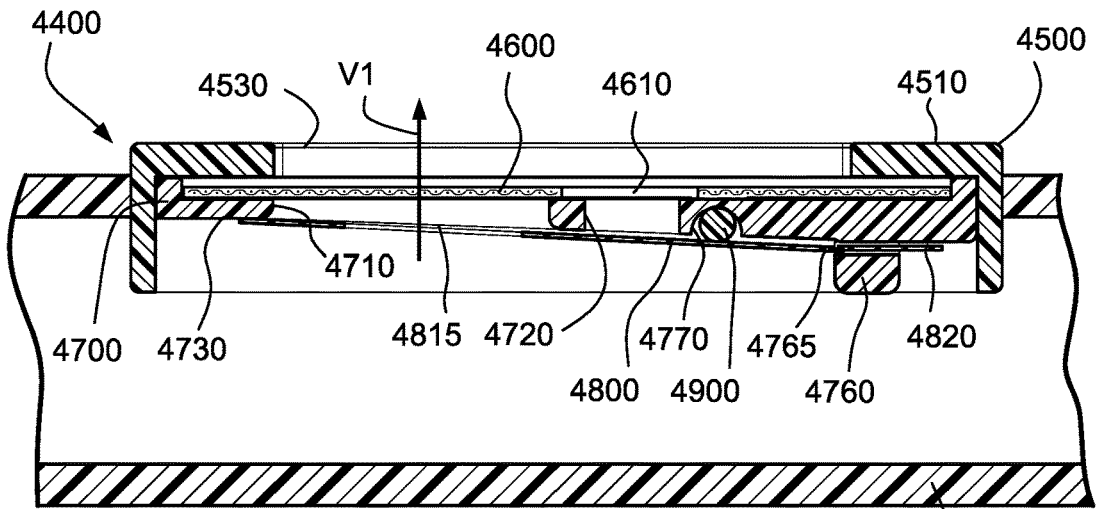

FIG. 5F is a cross-sectional view showing air passing through the vent assembly of FIG. 5A when there is air pressure in the air delivery conduit and the textile material is not blocked according to an example of the present technology.

Figure 5G:
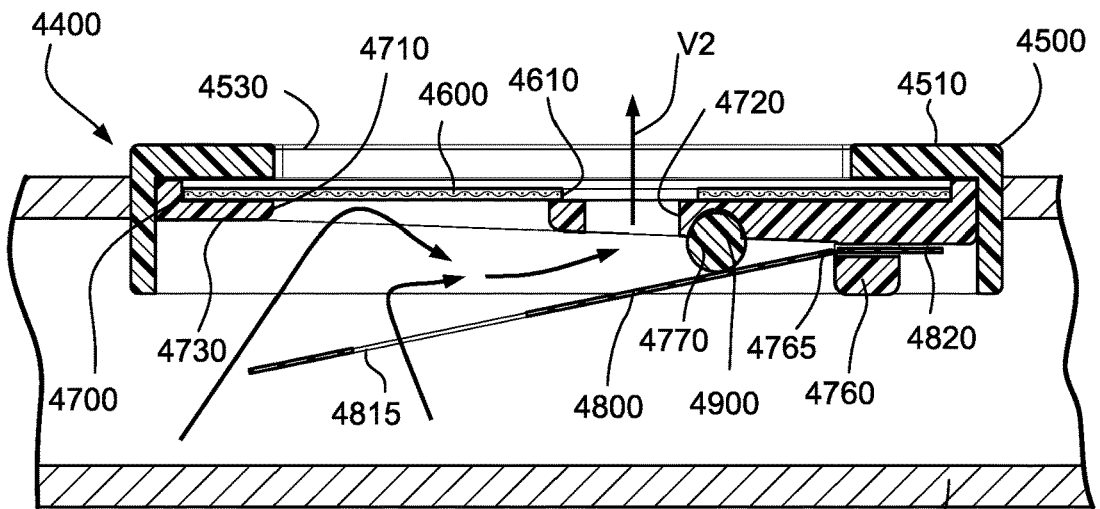

FIG. 5G is a cross-sectional view showing air passing through the vent assembly of FIG. 5A when there is air pressure in the air delivery conduit and the textile material is blocked according to an example of the present technology.

Figure 6A:
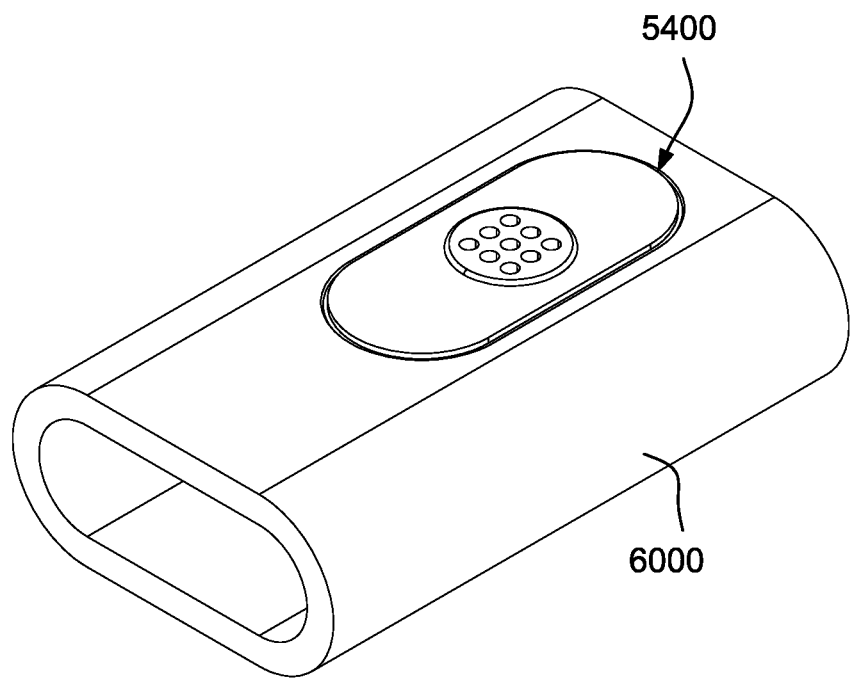

FIG. 6A is a perspective view of a vent assembly provided to an air delivery conduit according to an example of the present technology.

Figure 6B:
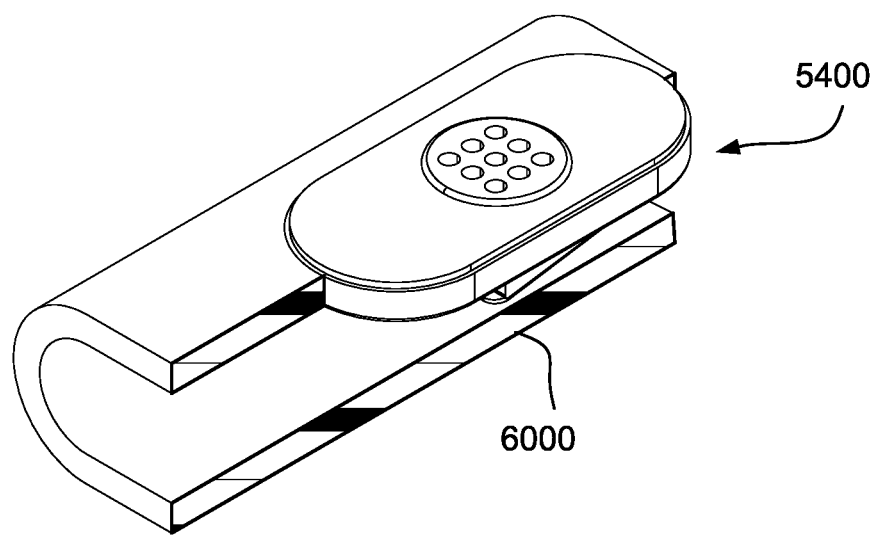

FIG. 6B is a cross-sectional view of a vent assembly provided to an air delivery conduit according to an example of the present technology.

Figure 6C:
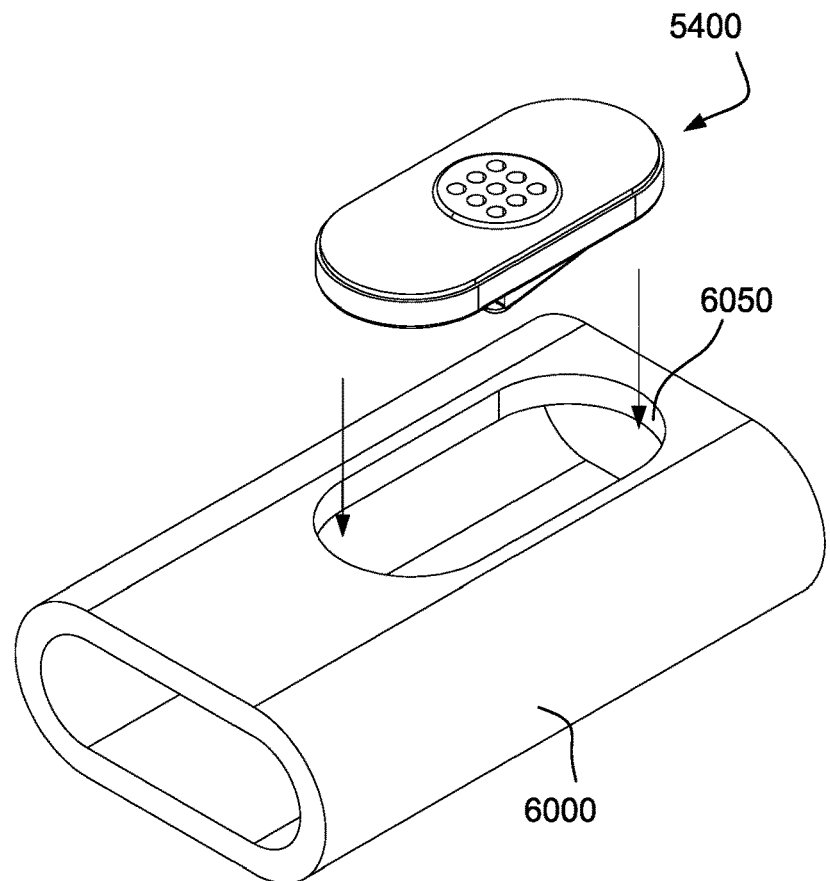

FIG. 6C is an exploded of a vent assembly and air delivery conduit according to an example of the present technology.

Figure 6D:
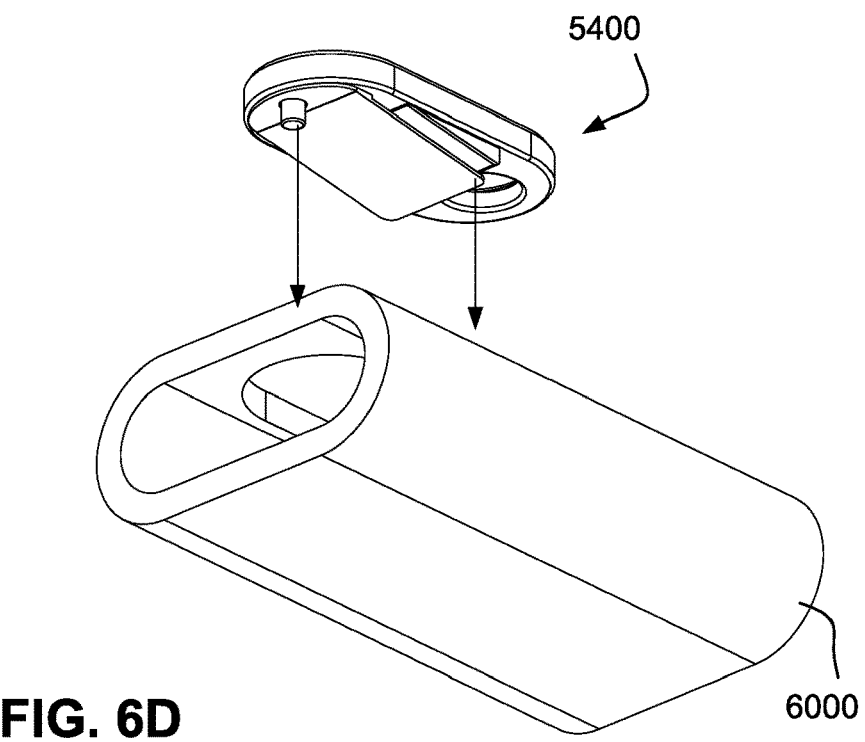

FIG. 6D is another exploded view of a vent assembly and air delivery conduit according to an example of the present technology.

Figure 6E:
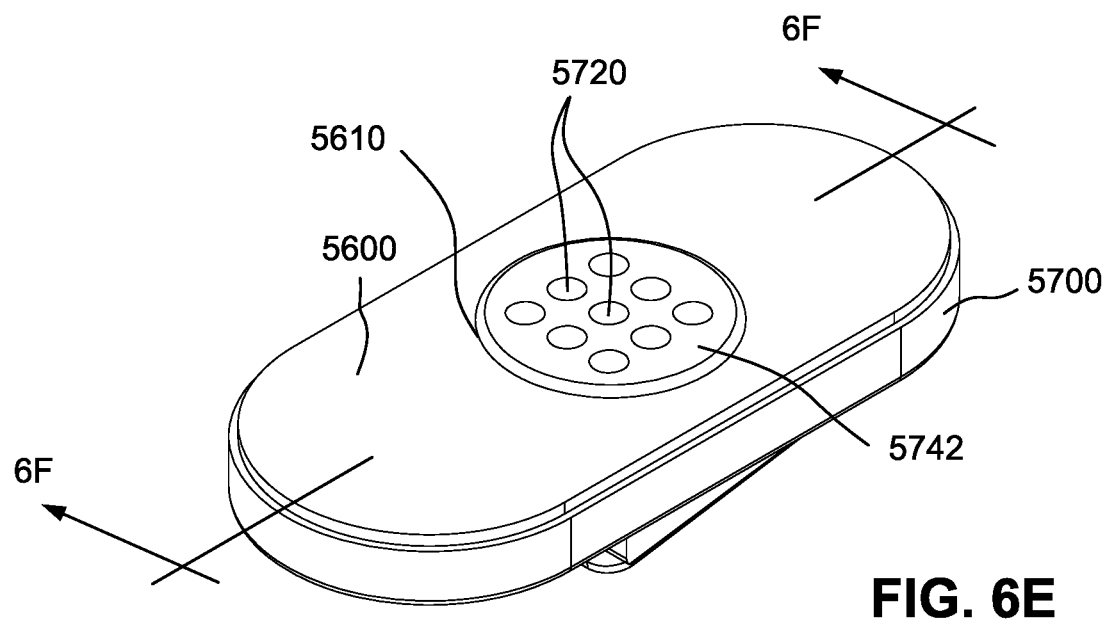

FIG. 6E is a perspective view of a vent assembly according to an example of the present technology.

Figure 6F:
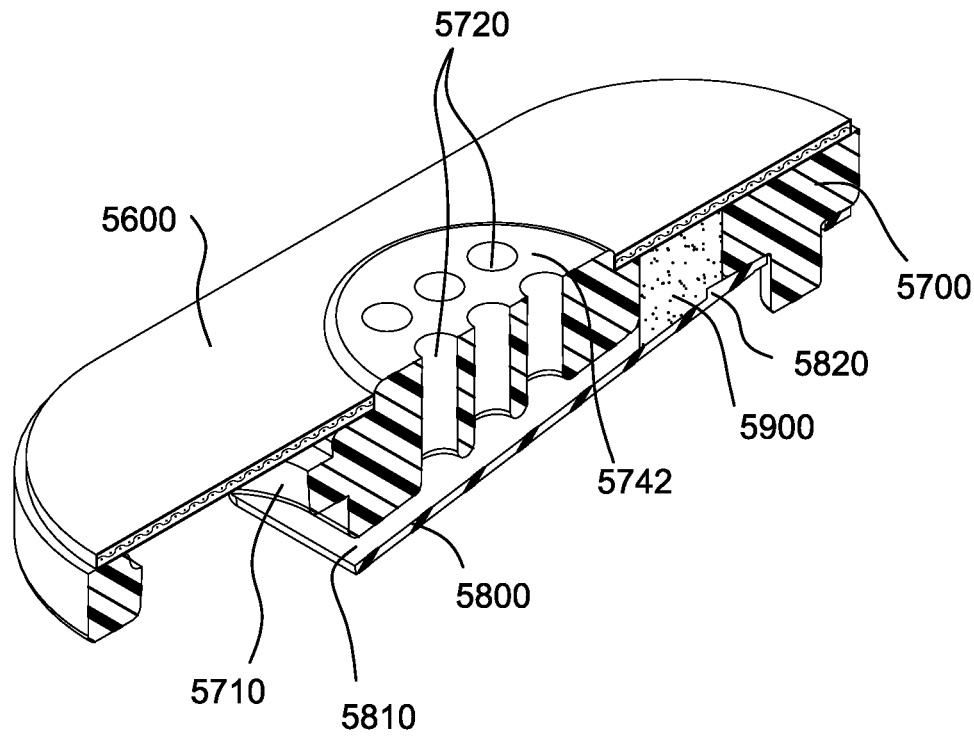

FIG. 6F is a cross-sectional view of the vent assembly of FIG. 6E.

Figure 6G:
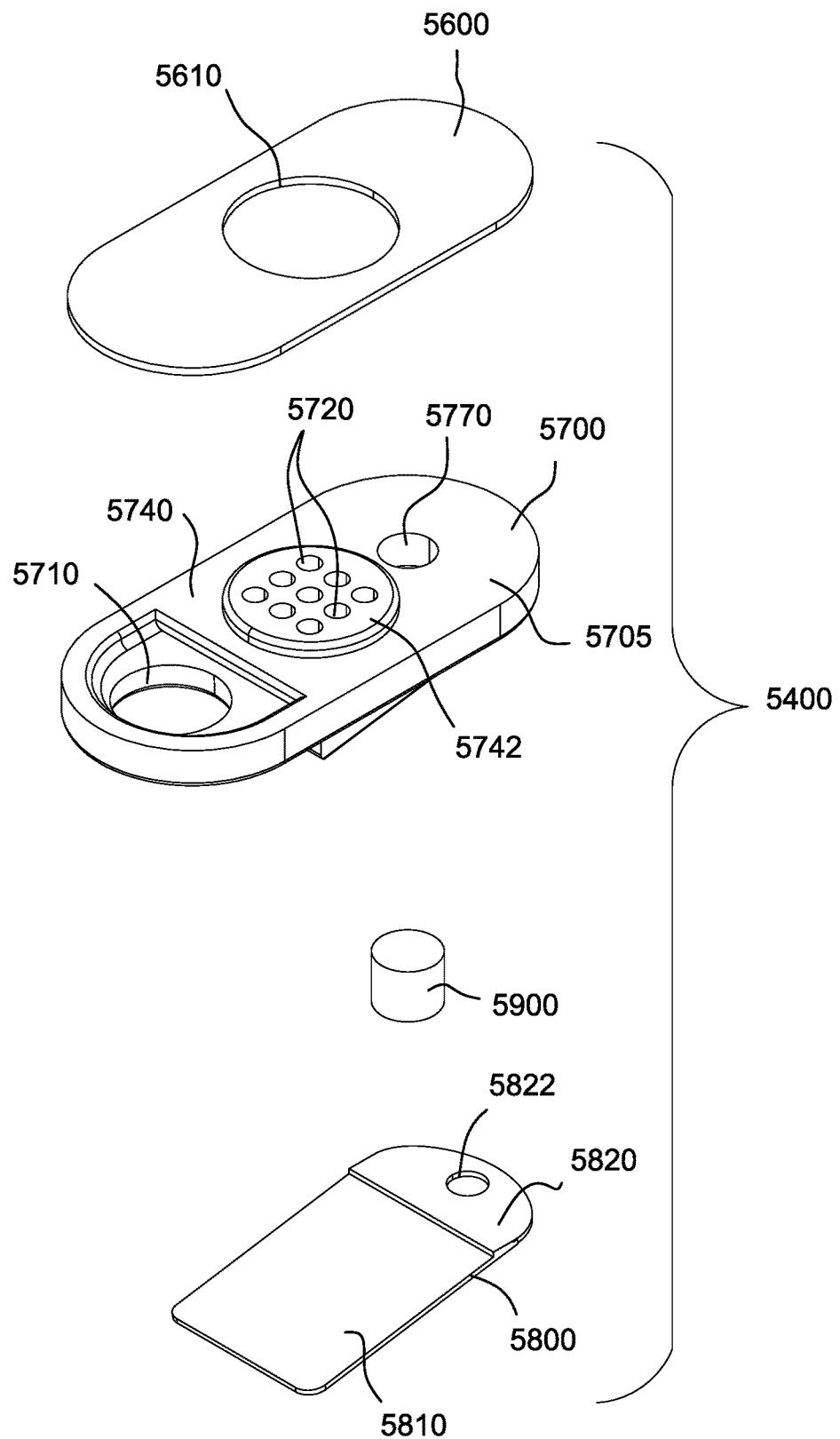

FIG. 6G is an exploded view of the vent assembly of FIG. 6E.

Figure 6H:
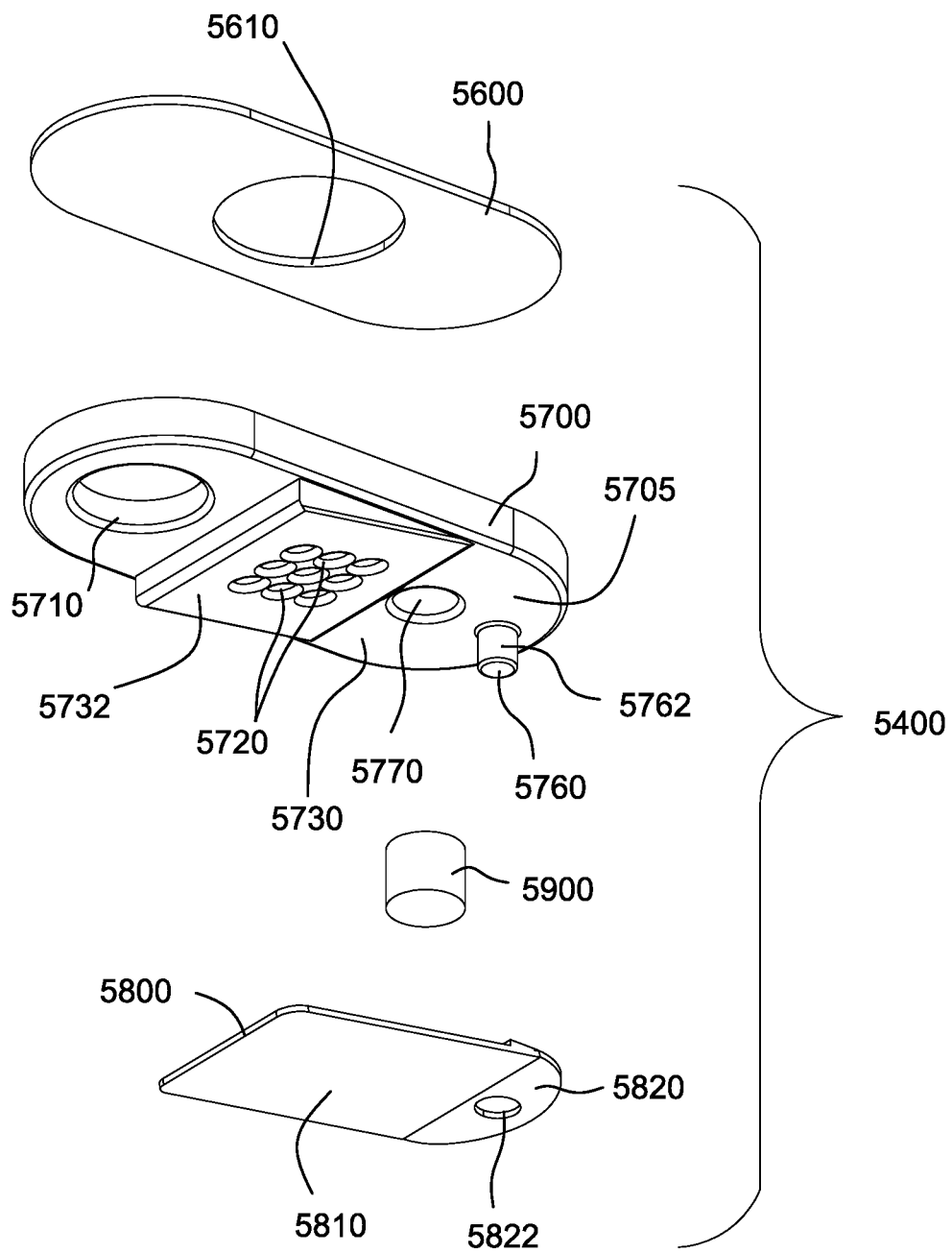

FIG. 6H is another exploded view of the vent assembly of FIG. 6E.

Figure 6I:
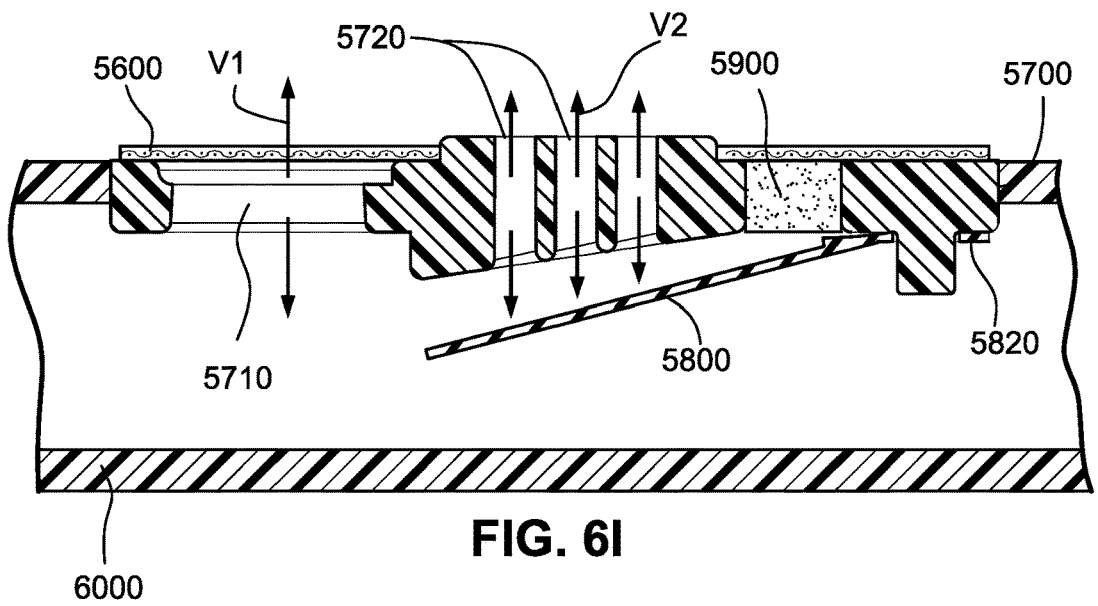

FIG. 6I is a cross-sectional view showing air passing through the vent assembly of FIG. 6E when there is no air pressure or low pressure in the air delivery conduit and the textile material is not blocked according to an example of the present technology.

Figure 6J:
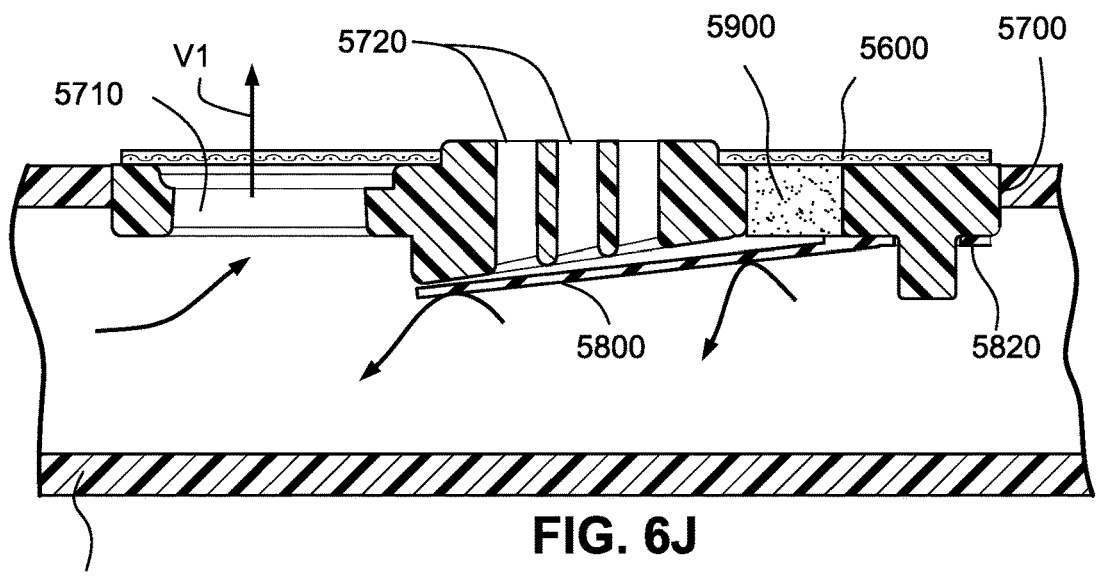

FIG. 6J is a cross-sectional view showing air passing through the vent assembly of FIG. 6E when there is air pressure in the air delivery conduit and the textile material is not blocked according to an example of the present technology.

Figure 6K:
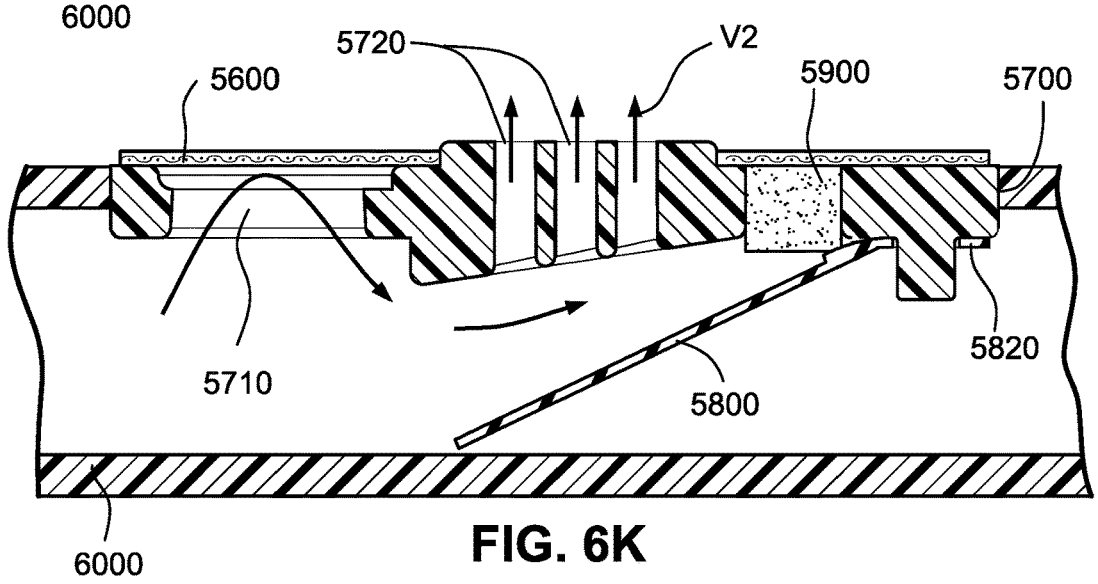

FIG. 6K is a cross-sectional view showing air passing through the vent assembly of FIG. 6E when there is air pressure in the air delivery conduit and the textile material is blocked according to an example of the present technology.

Figure 7A:
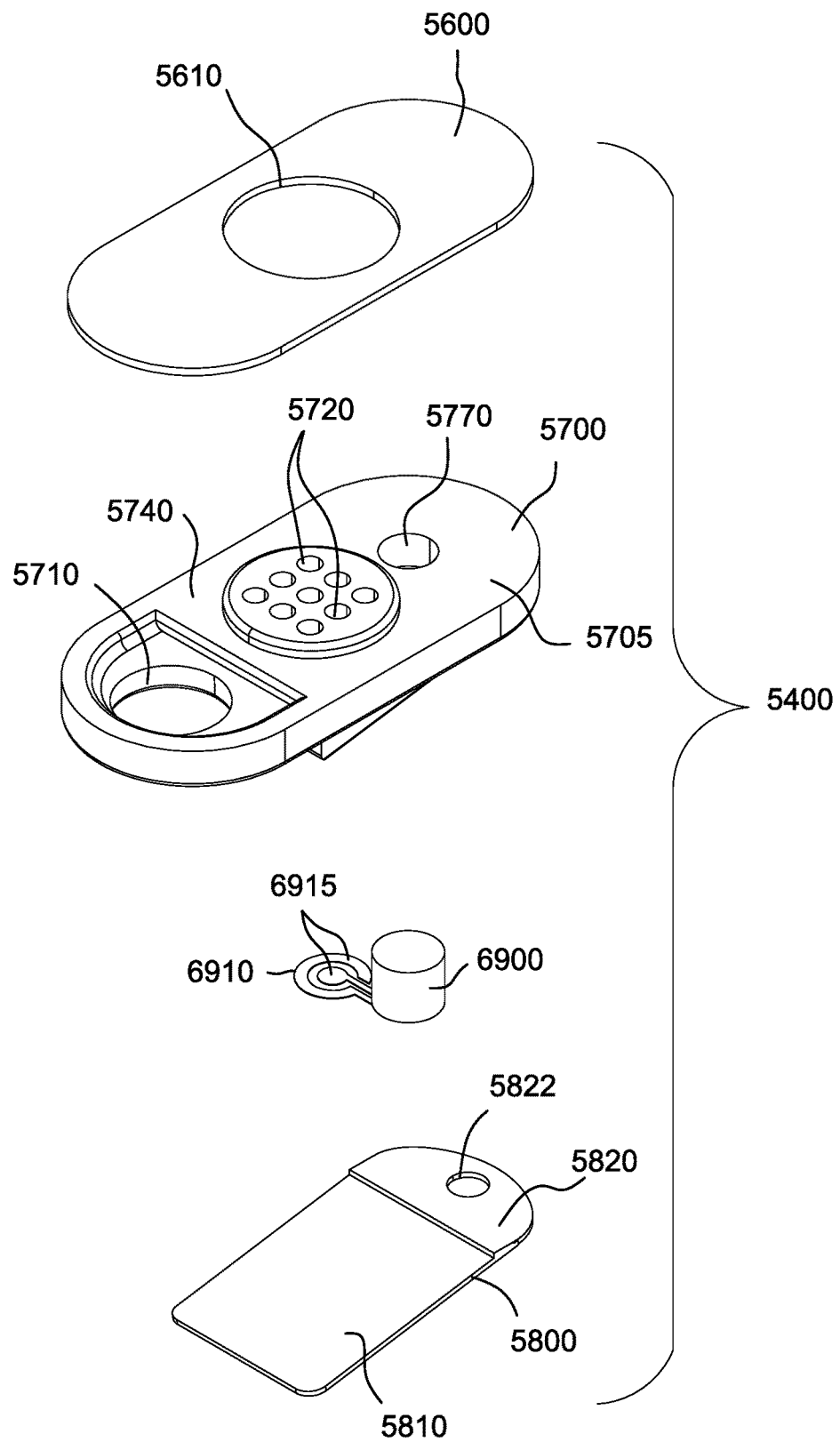

FIG. 7A is an exploded view of a vent assembly according to an example of the present technology.

Figure 7B:
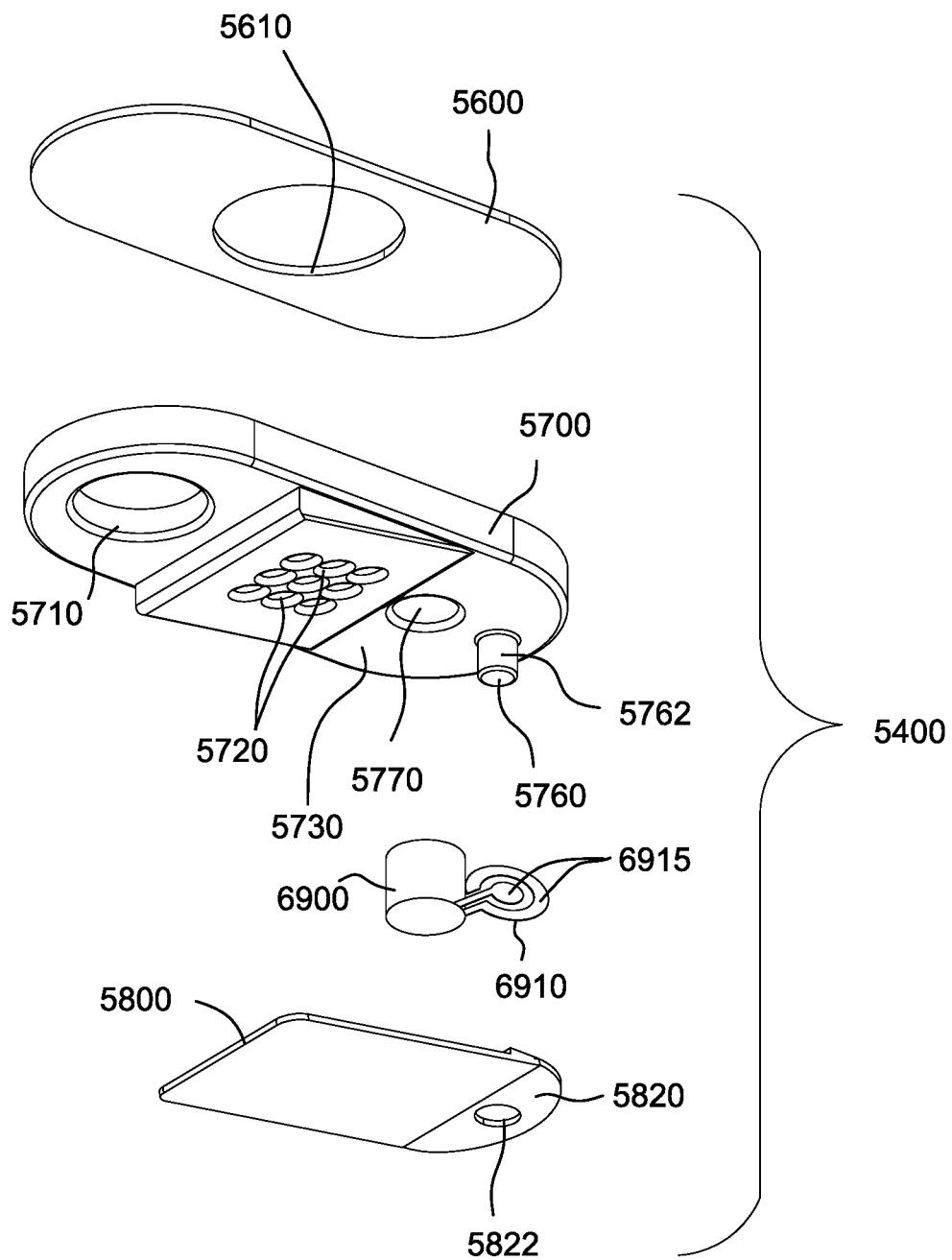

FIG. 7B is another exploded view of the vent assembly of FIG. 7A.

Figure 7C:
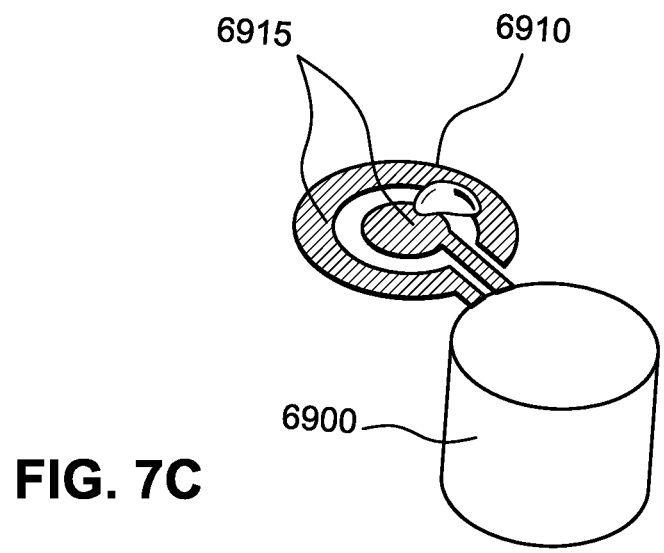

FIG. 7C is a perspective view of an activator and sensor of the vent assembly of FIG. 7A.

Figure 8A:
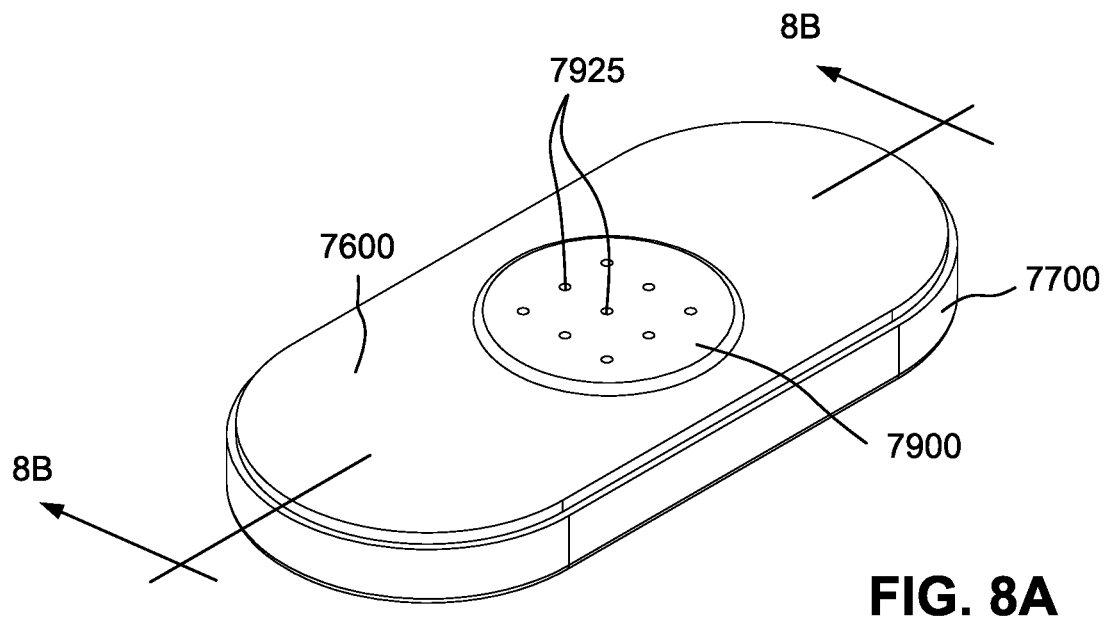

FIG. 8A is a perspective view of a vent assembly according to an example of the present technology.

Figure 8B:
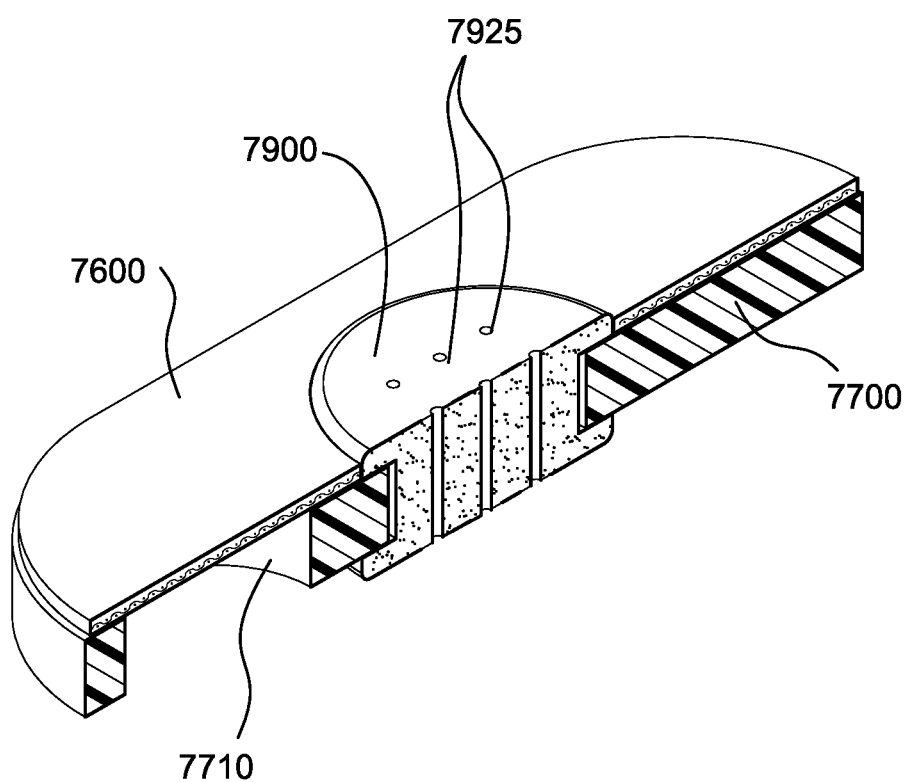

FIG. 8B is a cross-sectional view of the vent assembly of FIG. 8A.

Figure 8C:
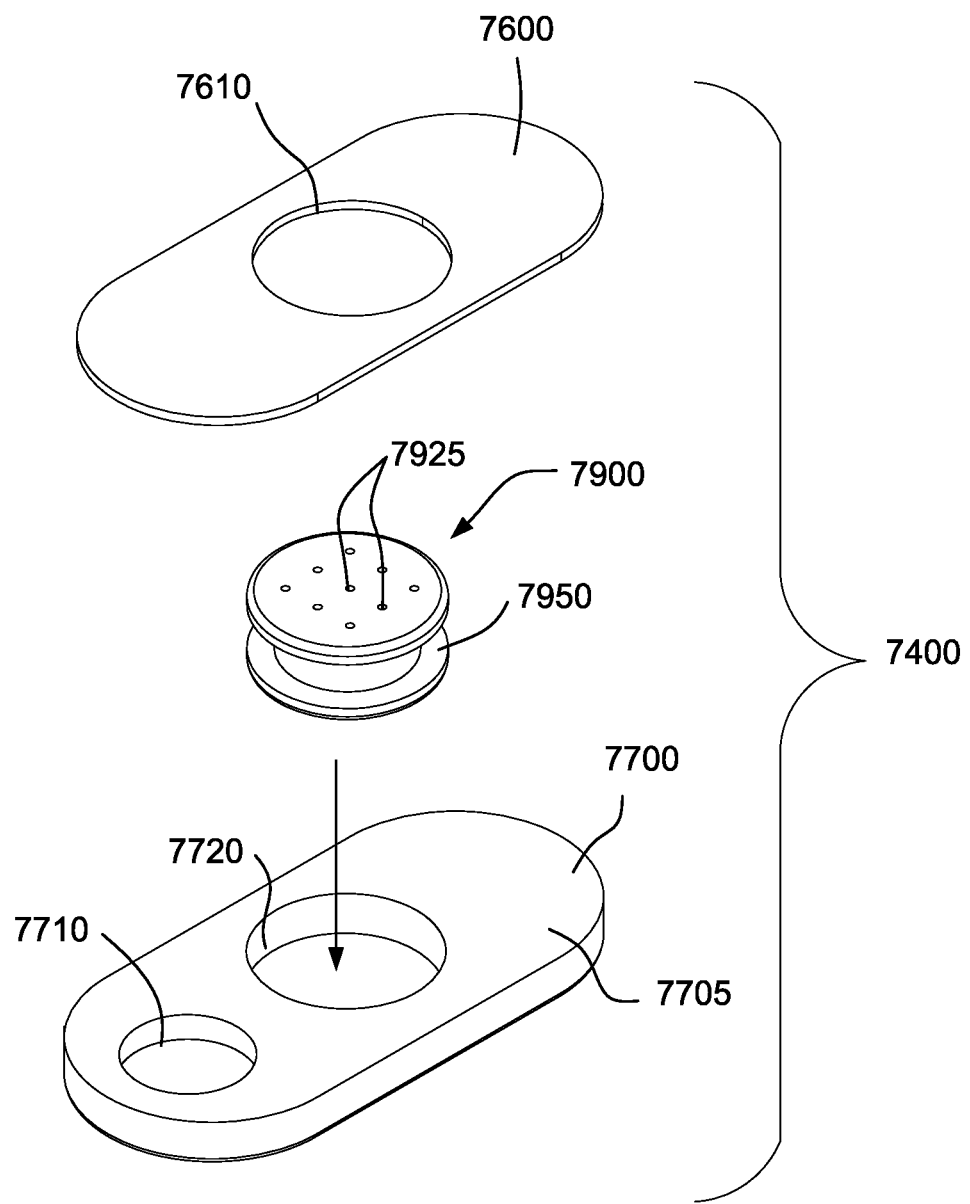

FIG. 8C is an exploded view of the vent assembly of FIG. 8A.

Figure 8D:
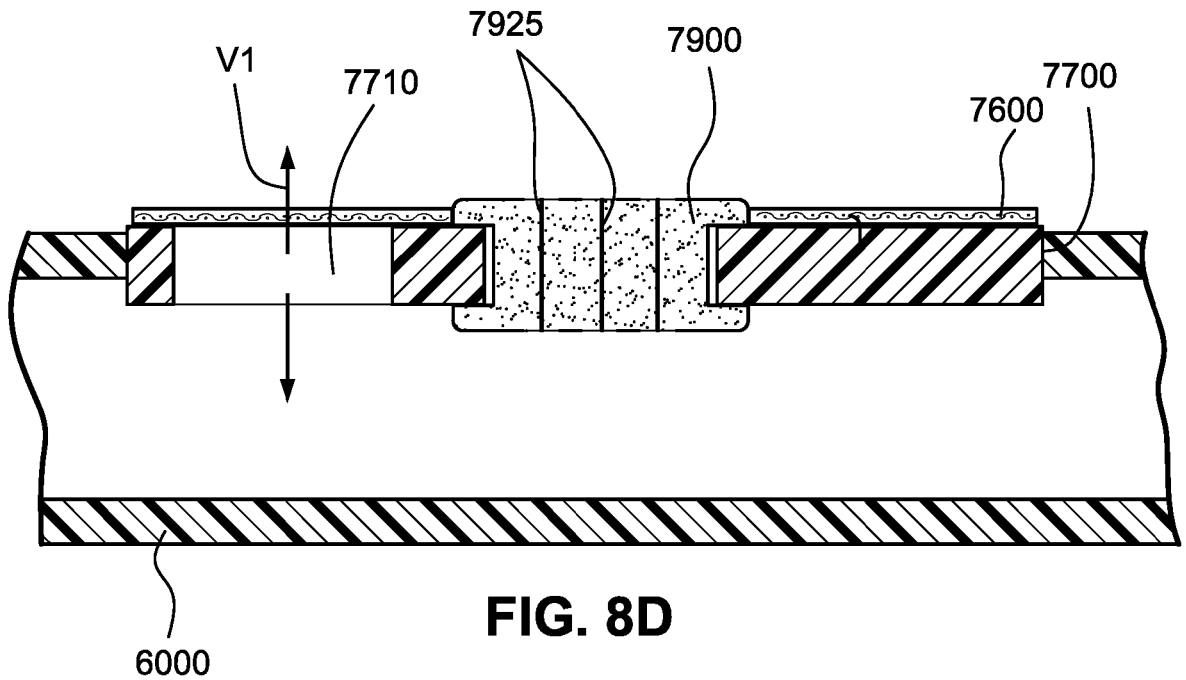

FIG. 8D is a cross-sectional view showing air passing through the vent assembly of FIG. 8A when there is air pressure in the air delivery conduit and the textile material is not blocked according to an example of the present technology.

Figure 8E:
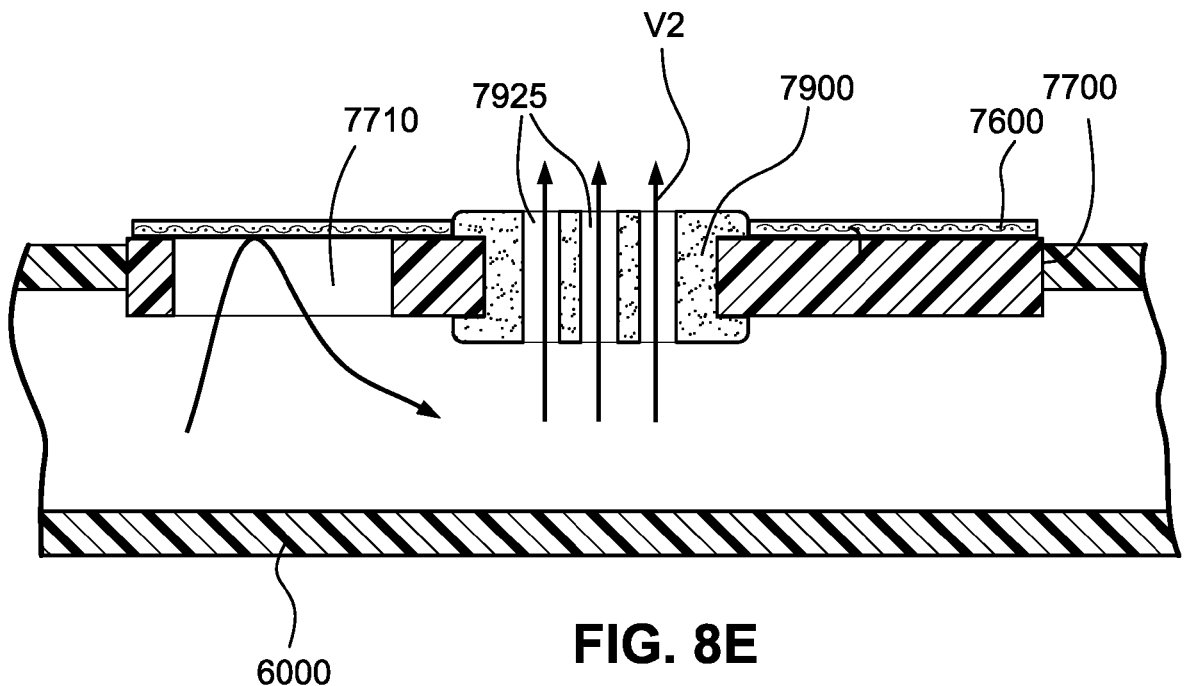

FIG. 8E is a cross-sectional view showing air passing through the vent assembly of FIG. 8A when there is air pressure in the air delivery conduit and the textile material is blocked according to an example of the present technology.

Figure 9A:
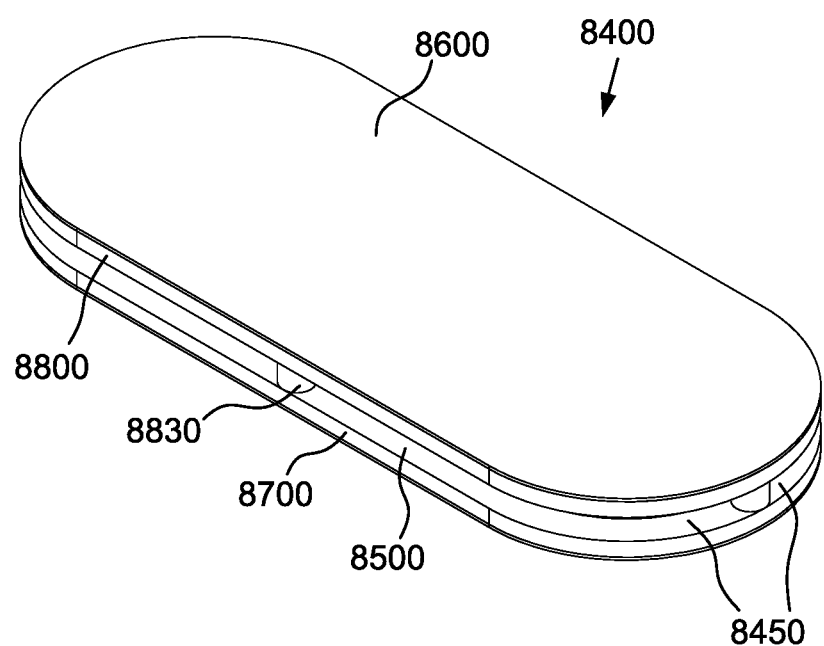

FIG. 9A is a top perspective view of a vent assembly according to an example of the present technology.

Figure 9B:
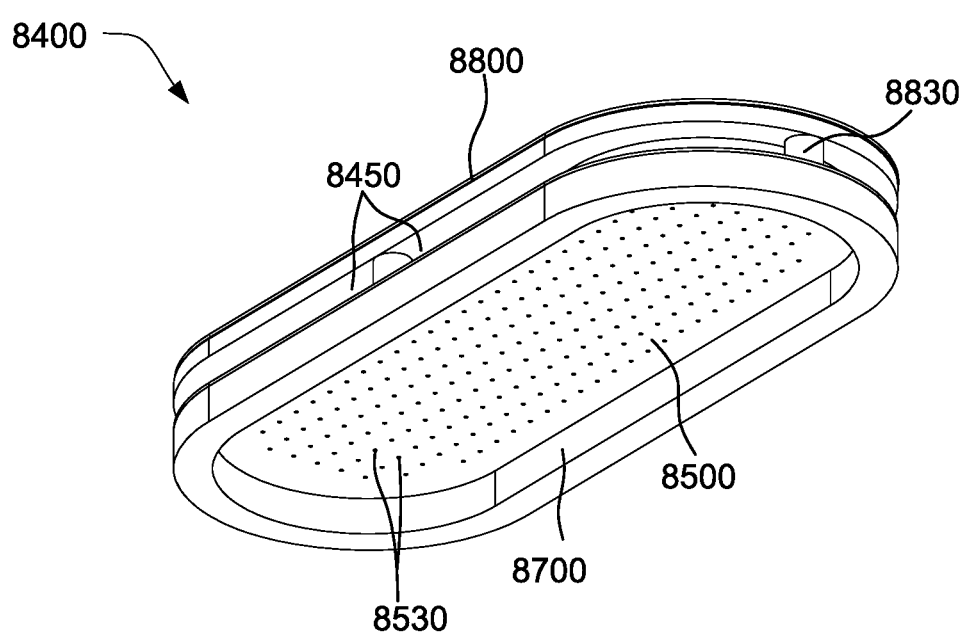

FIG. 9B is a bottom perspective view of the vent assembly of FIG. 9A.

Figure 9C:
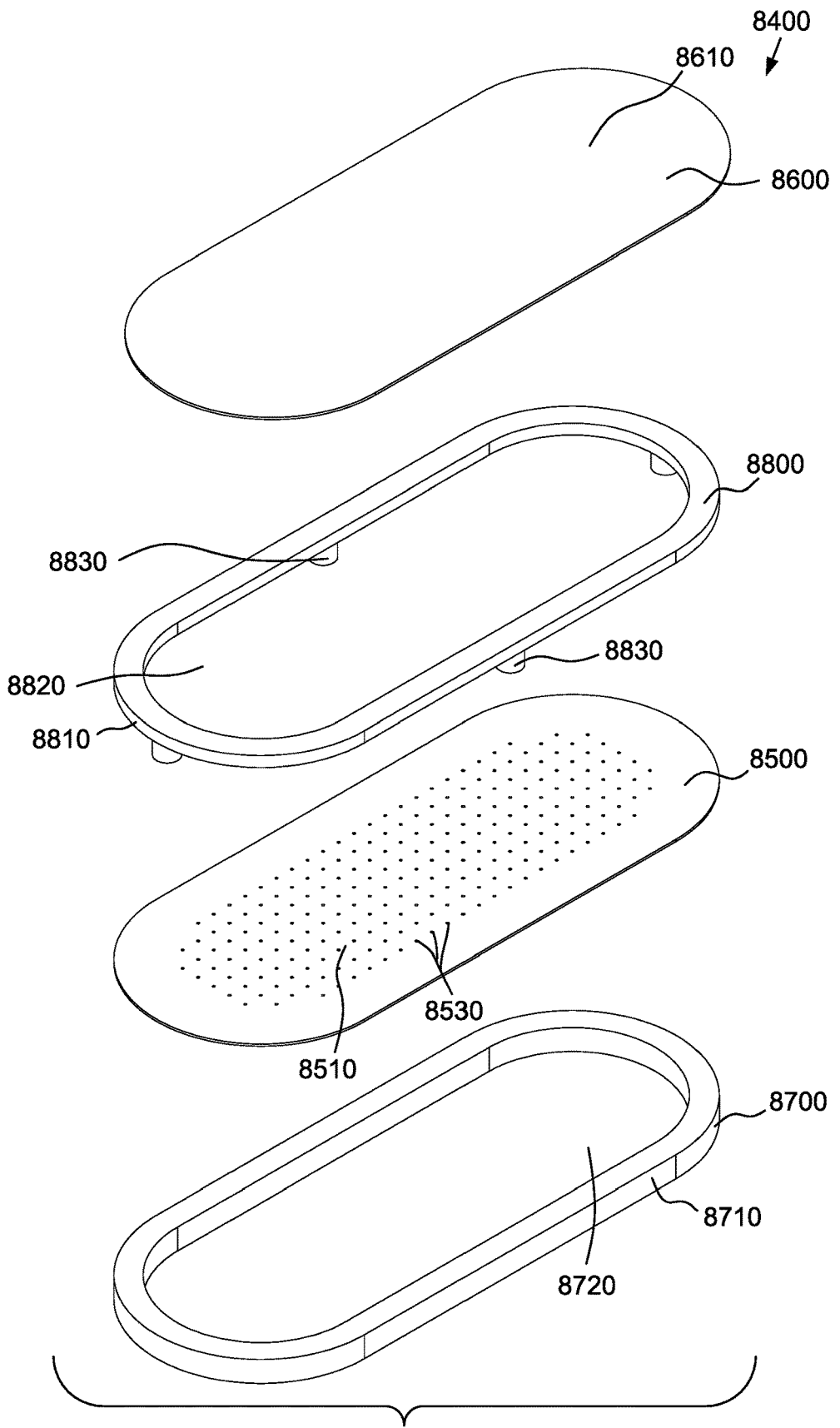

FIG. 9C is an exploded view of the vent assembly of FIG. 9A.

Figure 9D:
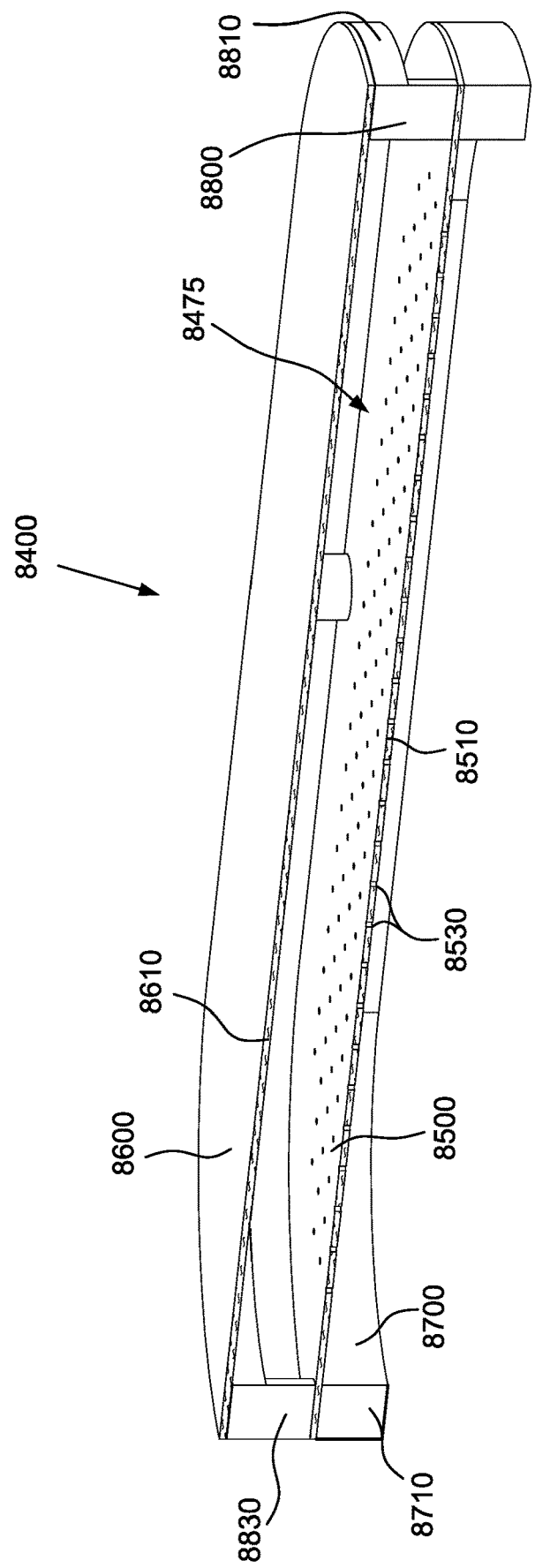

FIG. 9D is a cross-sectional view of the vent assembly of FIG. 9A.

Figure 9E:
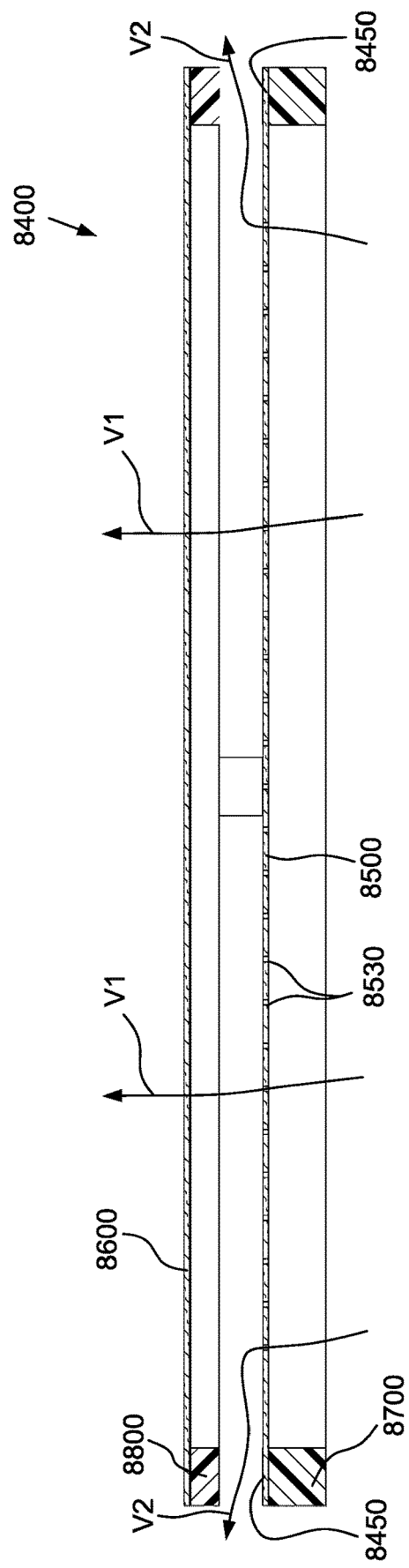

FIG. 9E is a cross-sectional view showing air passing through the vent assembly of FIG. 9A when there is air pressure and the diffusing member is not blocked according to an example of the present technology.

Figure 9F:
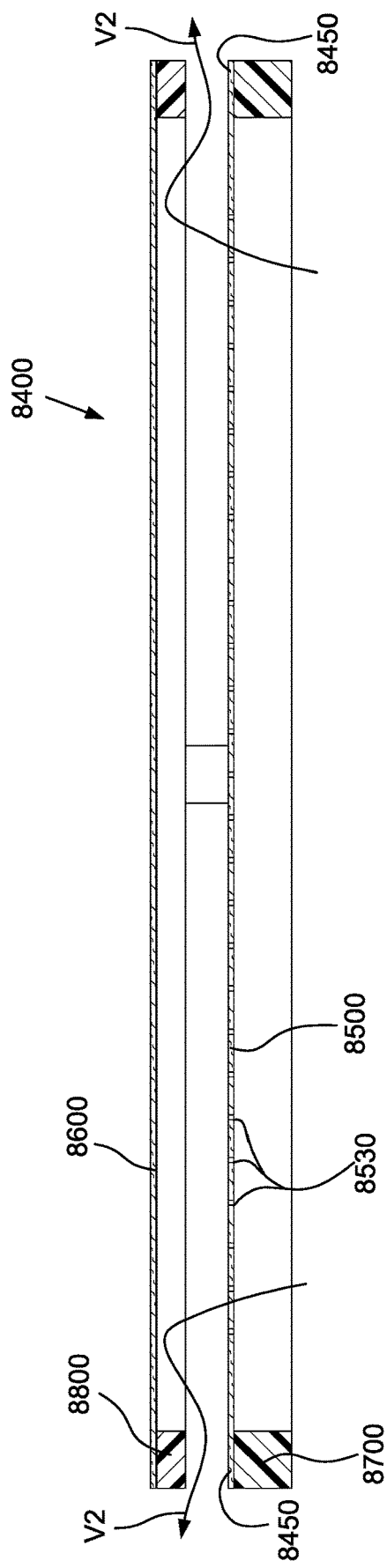

FIG. 9F is a cross-sectional view showing air passing through the vent assembly of FIG. 9A when there is air pressure and the diffusing member is blocked according to an example of the present technology.

Figure 10A:
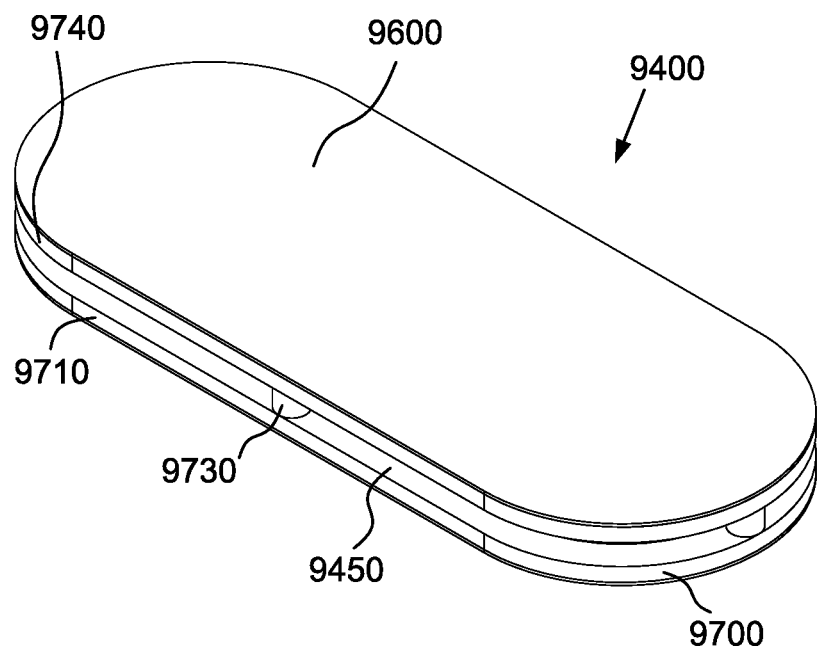

FIG. 10A is a top perspective view of a vent assembly according to an example of the present technology.

Figure 10B:
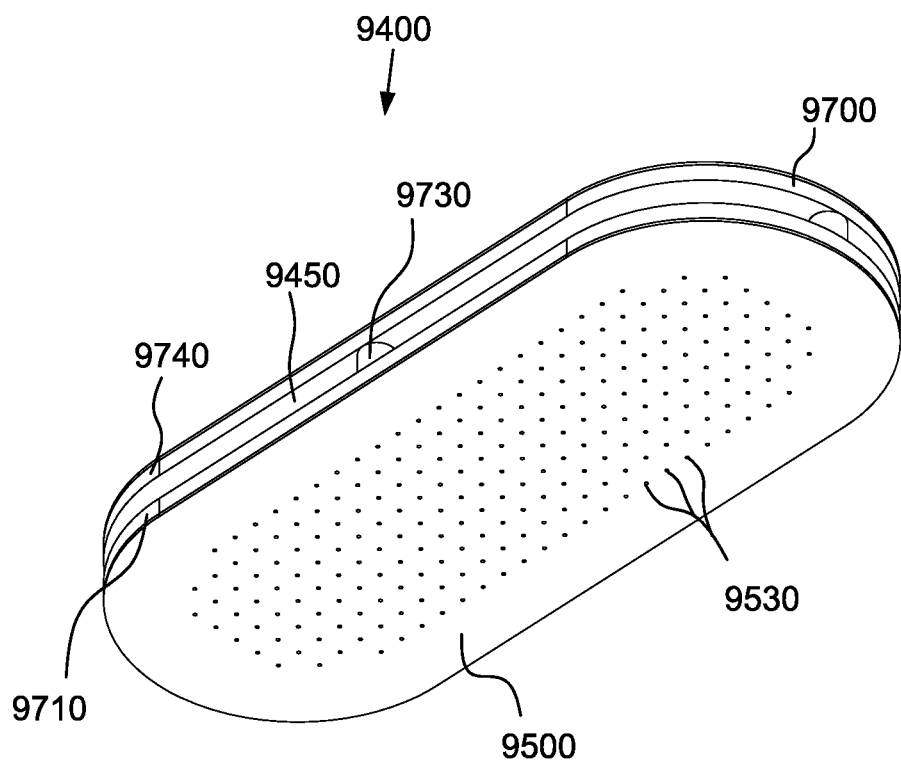

FIG. 10B is a bottom perspective view of the vent assembly of FIG. 10A.

Figure 10C:
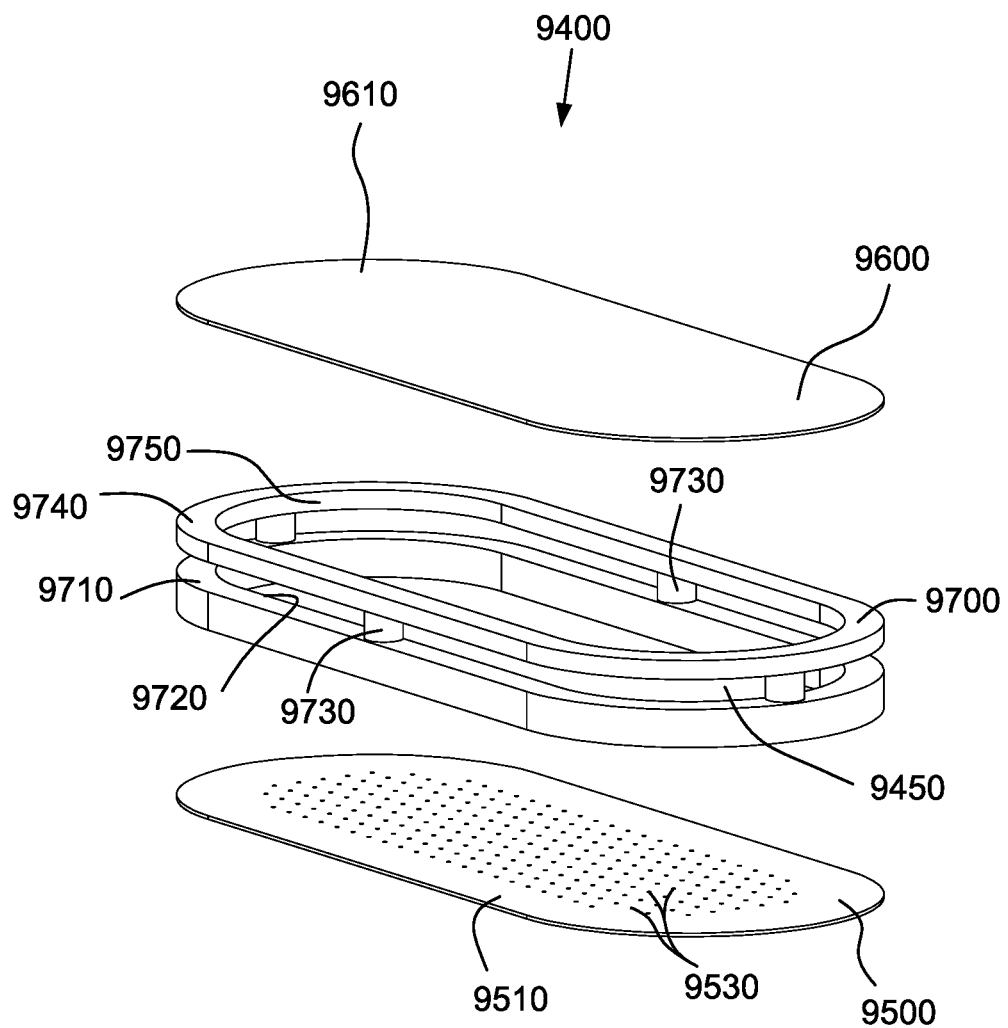

FIG. 10C is an exploded view of the vent assembly of FIG. 10A.

Figure 10D:
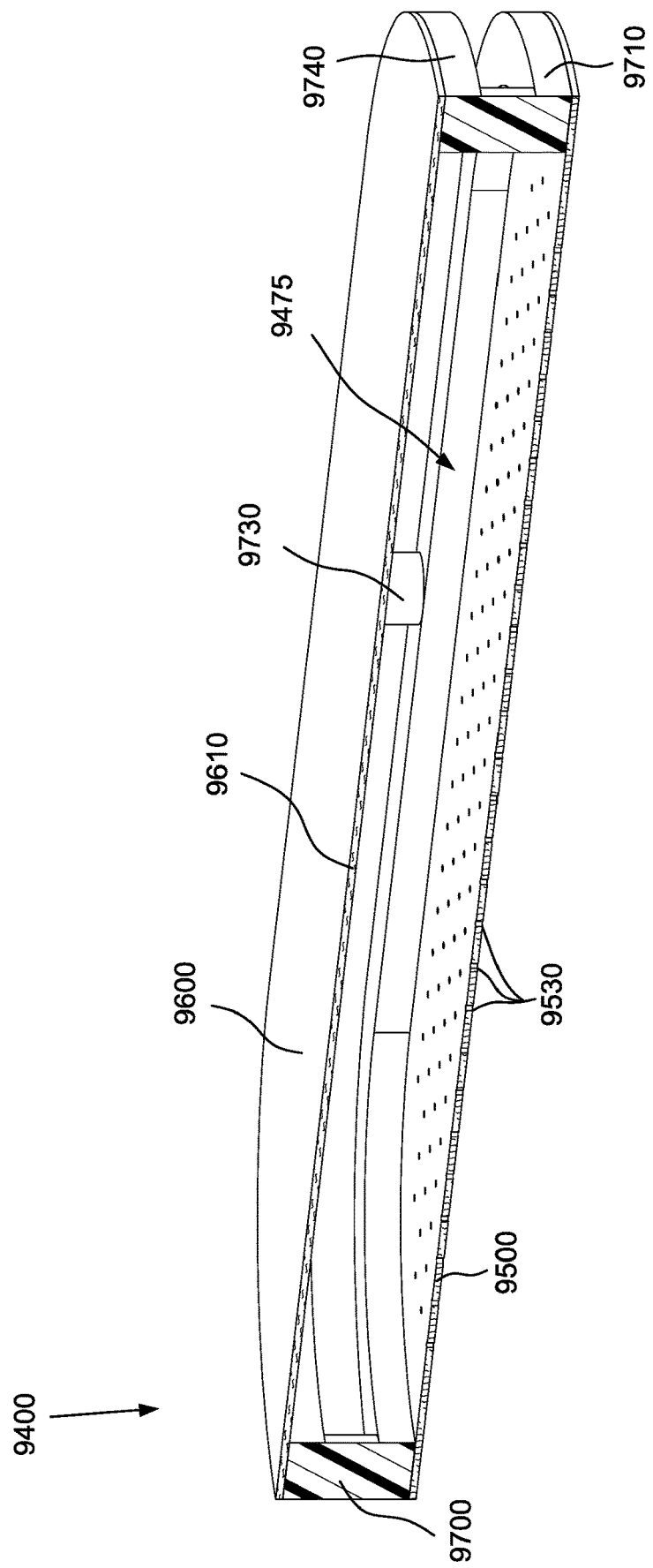

FIG. 10D is a cross-sectional view of the vent assembly of FIG. 10A.

Figure 10E:
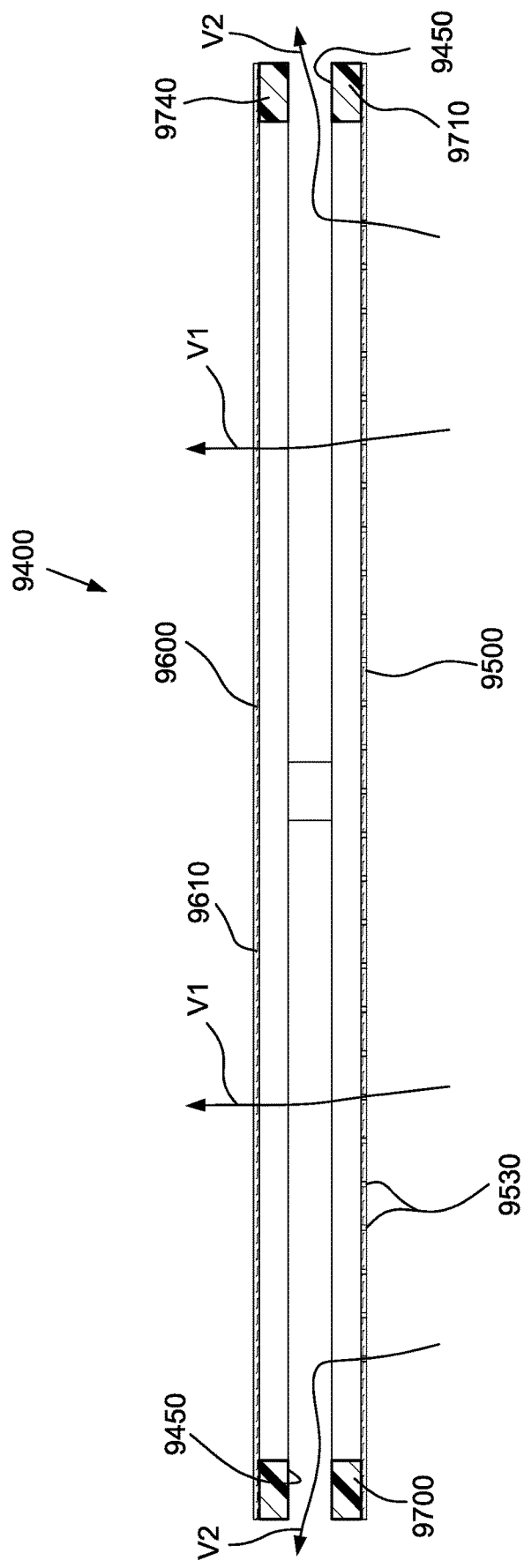

FIG. 10E is a cross-sectional view showing air passing through the vent assembly of FIG. 10A when there is air pressure and the diffusing member is not blocked according to an example of the present technology.

Figure 10F:
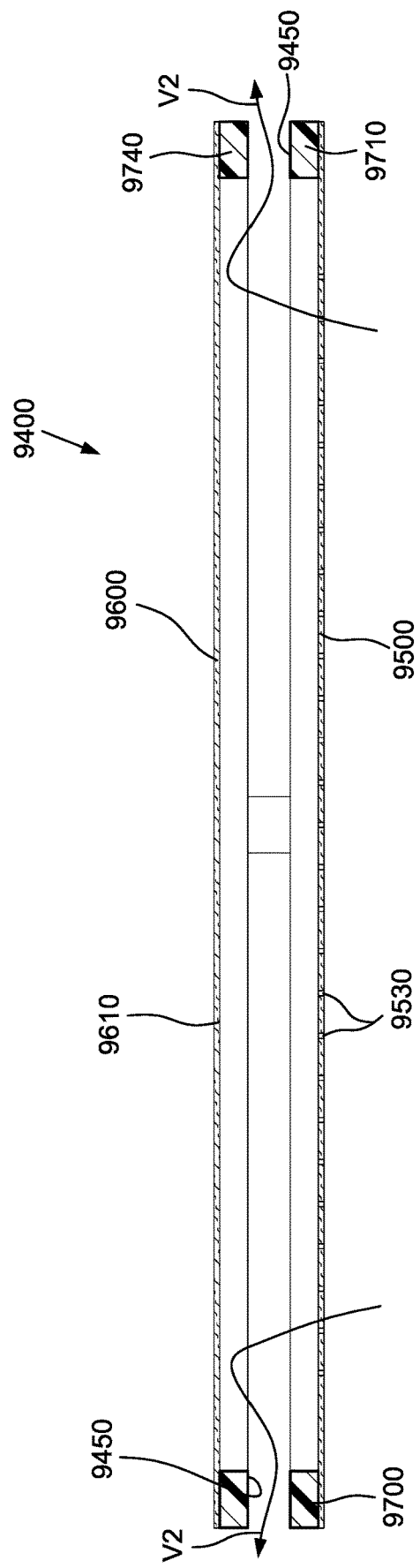

FIG. 10F is a cross-sectional view showing air passing through the vent assembly of FIG. 10A when there is air pressure and the diffusing member is blocked according to an example of the present technology.

Figure 11A:
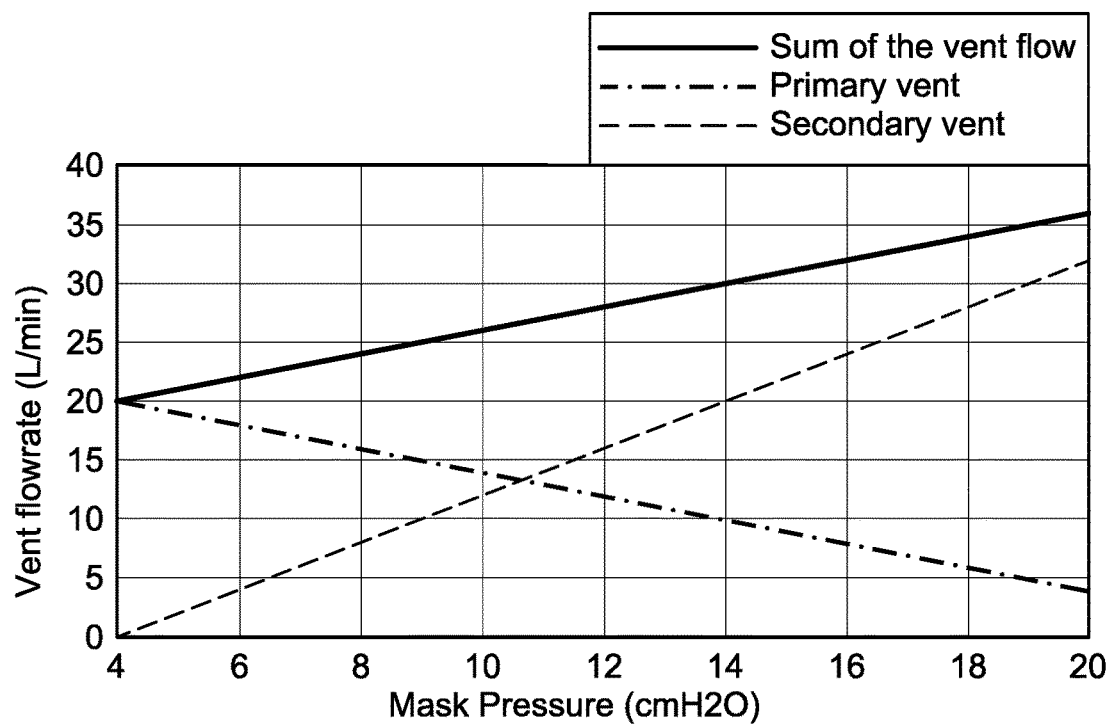

FIG. 11A is a graph showing exemplary vent flow through a vent assembly according to an example of the present technology.

Figure 11B:
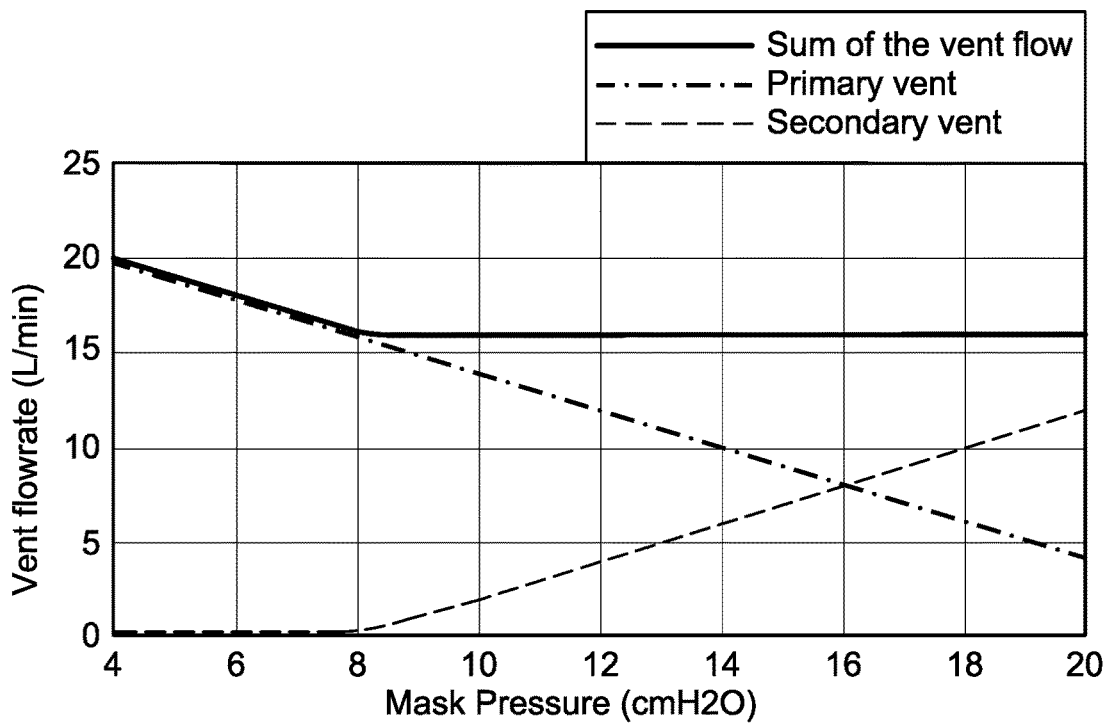

FIG. 11B is a graph showing exemplary vent flow through a vent assembly according to an example of the present technology.

Figure 11C:
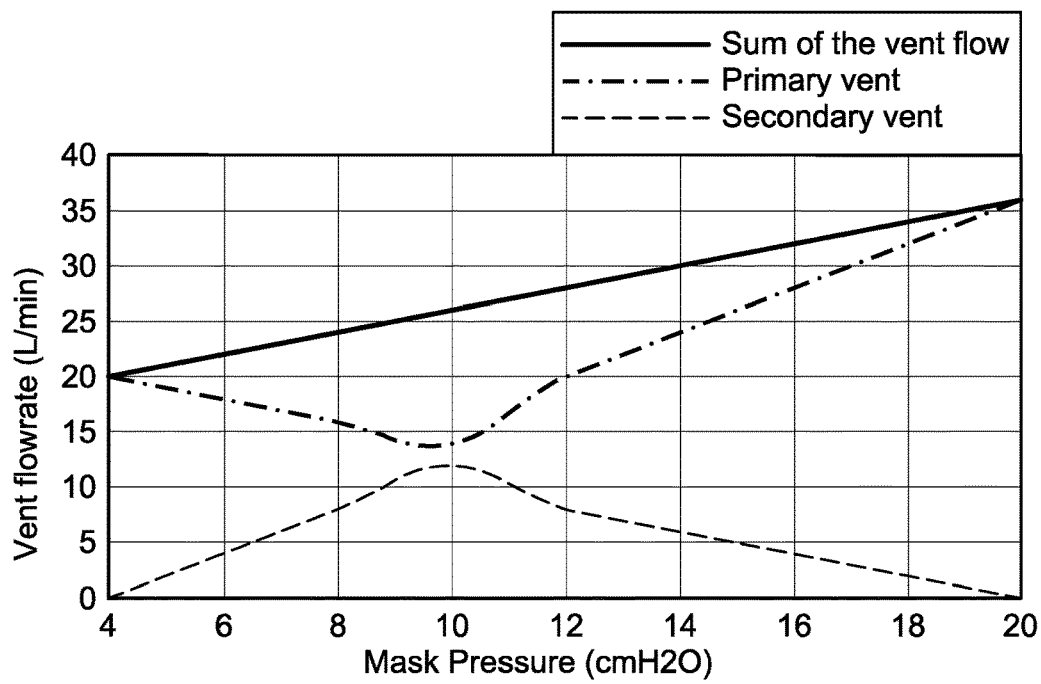

FIG. 11C is a graph showing exemplary vent flow through a vent assembly according to an example of the present technology.

Figure 11D:
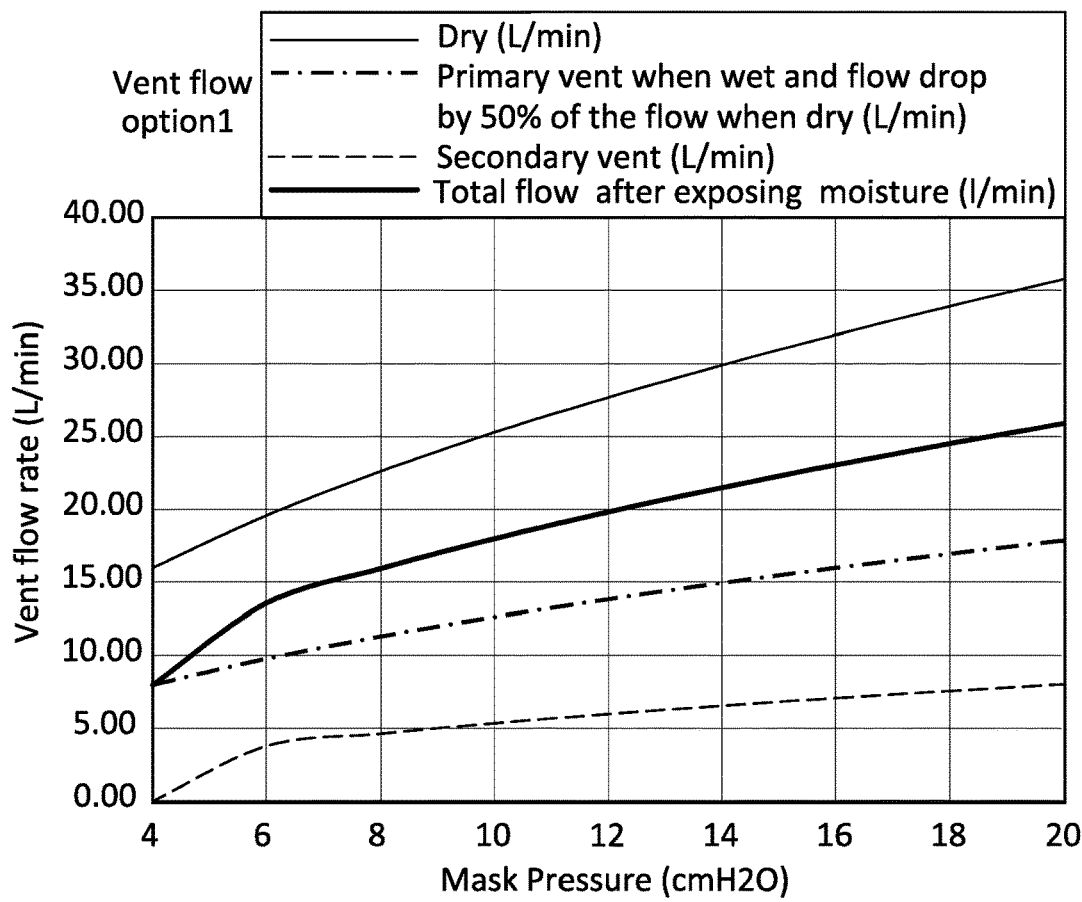

FIG. 11D is a graph showing exemplary vent flow through a vent assembly according to an example of the present technology.

Figure 11E:
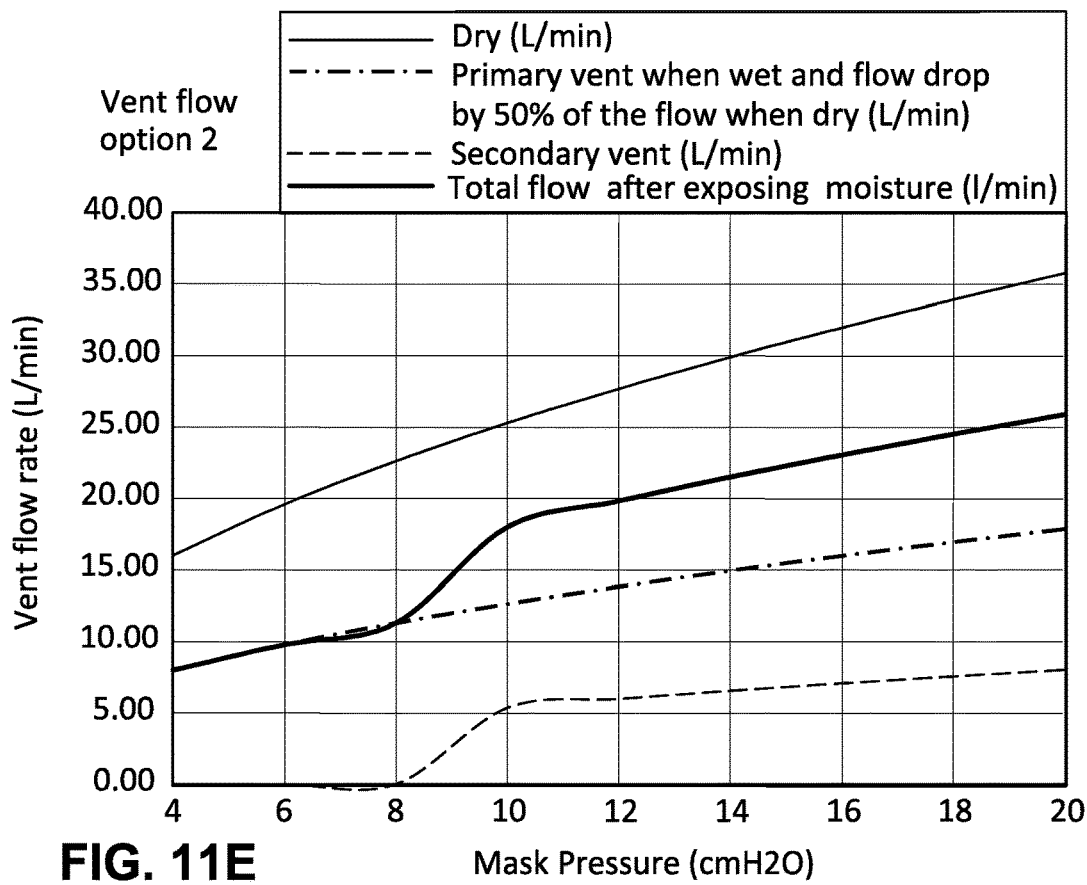

FIG. 11E is a graph showing exemplary vent flow through a vent assembly according to an example of the present technology.

Figure 11F:
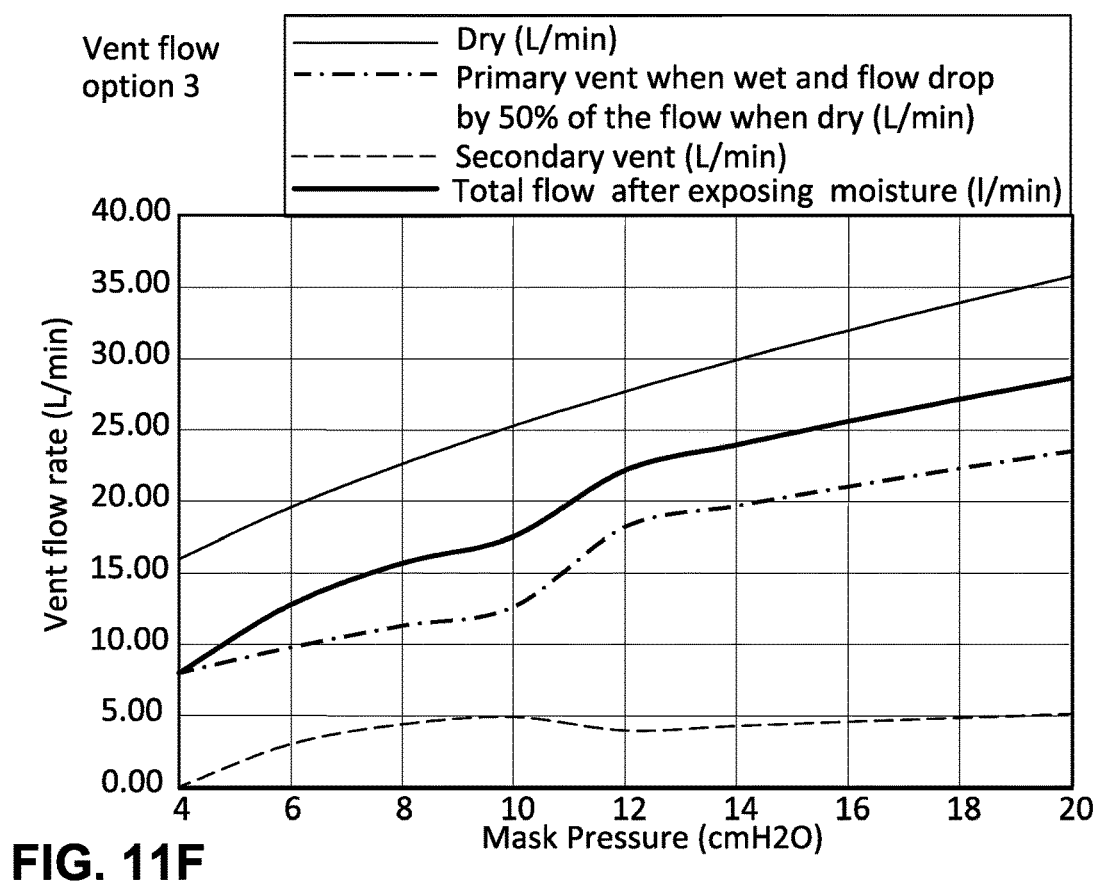

FIG. 11F is a graph showing exemplary vent flow through a vent assembly according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares. In certain examples of the present technology, mouth breathing is limited, restricted or prevented.

5.2 Treatment Systems

Figure 1A:
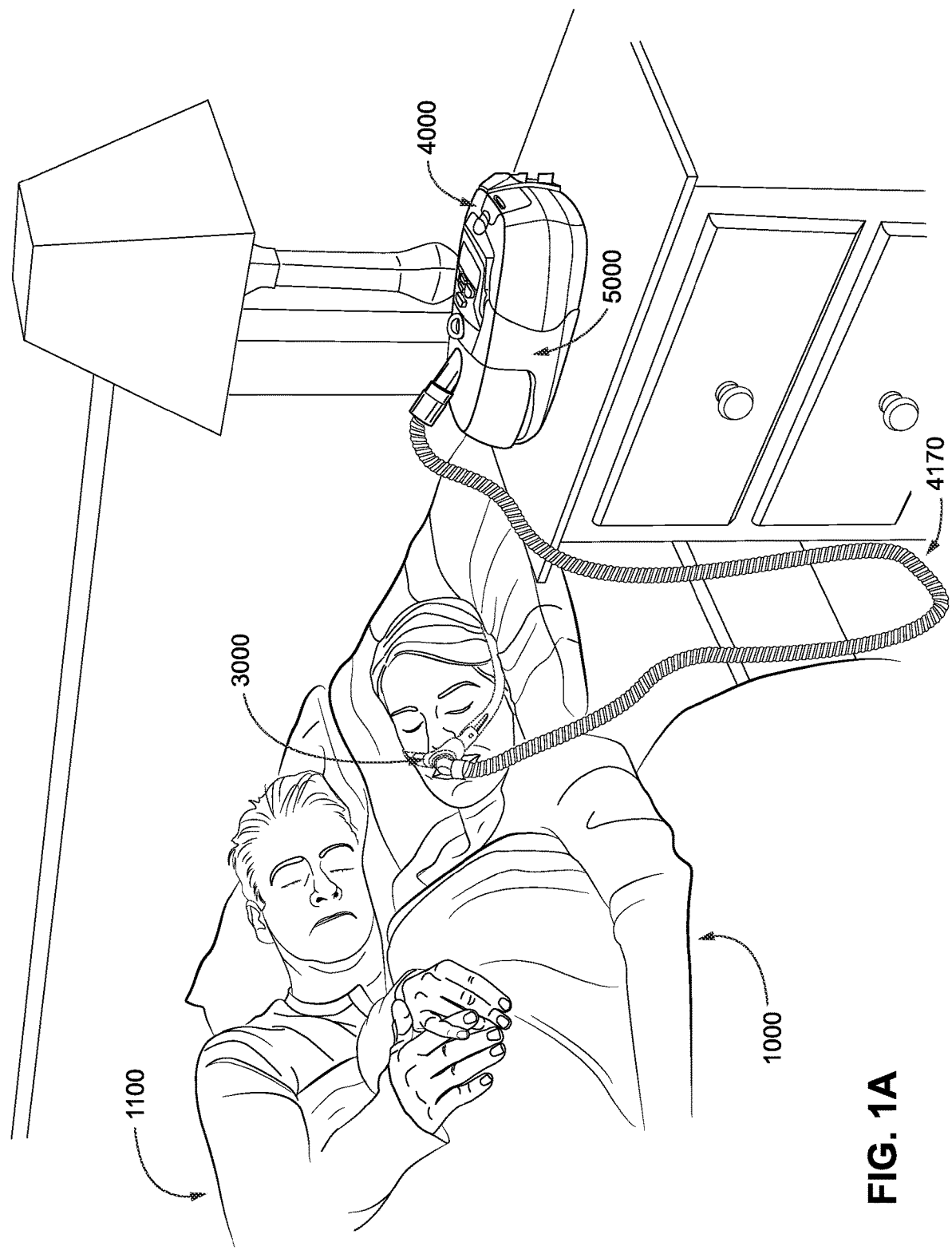
Figure 1B:
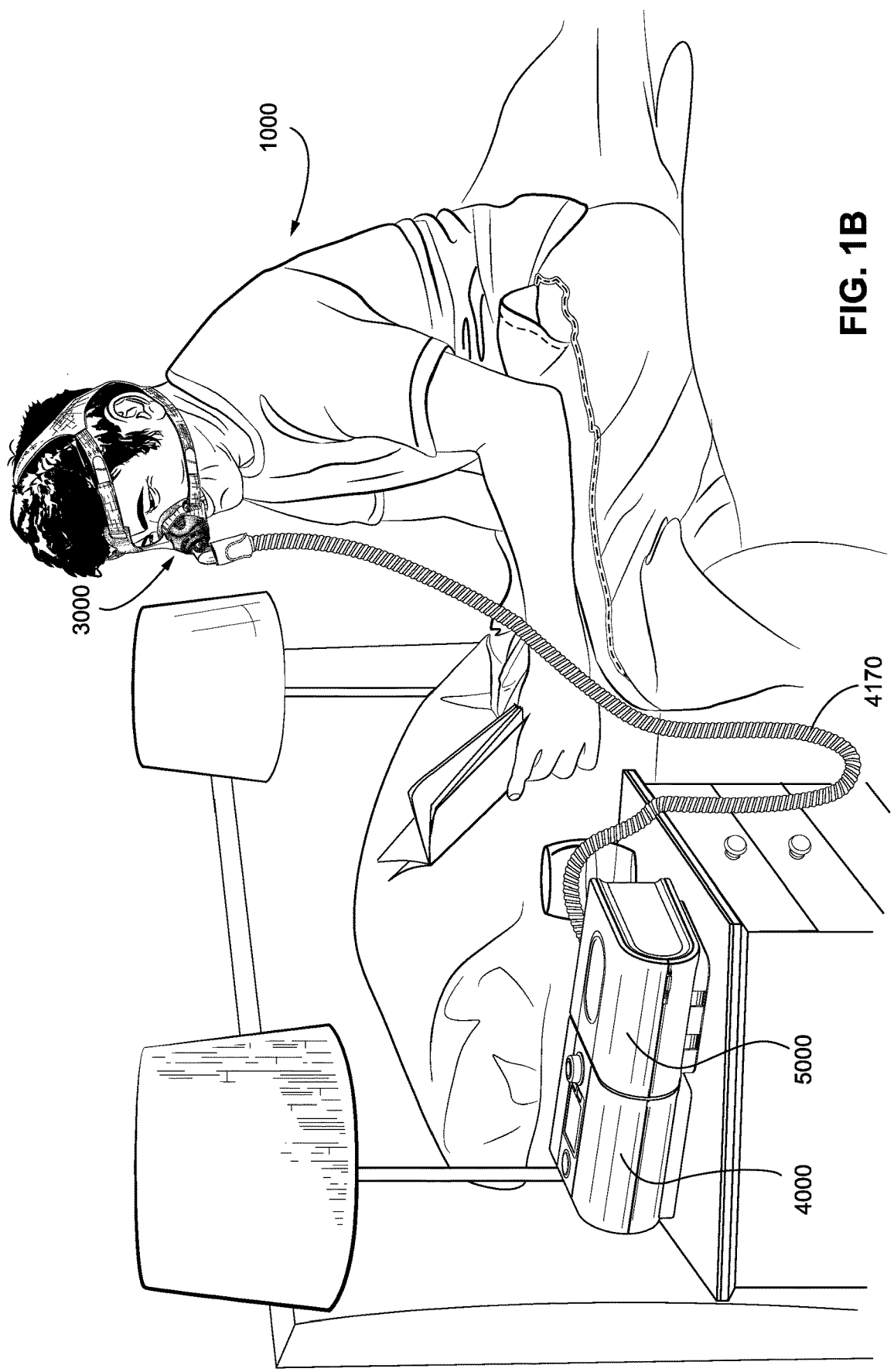
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

As shown in FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3600, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

Textile Vent Assembly

FIGS. 4A to 4K show a vent assembly 4400 configured to provide a vent flow of gas to discharge gas exhaled by the patient according to an example of the present technology. In the illustrated example, the vent assembly 4400 comprises a diffusing member, e.g., a layer of textile material 4600, along the vent flow path structured and arranged to diffuse the exhaust vent flow to produce less noise.

Vents including textile are extremely quiet and much diffused. However, textile vents can have a significant reduction in vent flow when exposed to high humidity or water. For example, the vent flow can be partially or completely blocked due to water retention or due to condensation in the textile fiber. The blockage can occur if the textile vent is not dried well after washing and/or if the textile vent is subjected to high humidity in cold weather. Once blockage occurs, it may take an unacceptably long duration for the textile vent to recover and return to the initial vent flow. If the textile vent is used under these conditions, it could lead to high $CO_2$ build up in the patient interface as $CO_2$ is not sufficiently vented. Due to the above reasons, textile vents are not widely used in CPAP therapy.

An aspect of the present technology relates to a textile vent assembly structured and arranged to address the water retention issue and allow sufficient vent flow when the textile is blocked due to the textile being wet from water or humidity. Thus, the textile vent assembly according to an aspect of the present technology allows the use of textile as a safe and reliable vent component for CPAP therapy.

In the illustrated example, the vent assembly 4400 is in the form of a vent insert or cartridge structured to be inserted into an opening in a patient interface 3000 or an air delivery conduit, e.g., air circuit 4170.

For example, FIGS. 4A to 4D illustrate the vent assembly 4400 structured to be inserted into an opening 6050 of an air delivery conduit 6000. In use, the vent assembly 4400 is structured and arranged to allow a flow of gas from an interior or pressurized volume of the air delivery conduit 6000 to an exterior of the air delivery conduit 6000, e.g., to atmosphere. The vent assembly 4400 may be removably or permanently secured within the opening 6050 in any suitable manner, e.g., press fit assembly, snap or interference fit assembly (e.g., vent assembly may include a groove around its periphery, the groove adapted to locate the vent assembly against a correspondingly sized rim of the opening of the air delivery conduit), adhesive. In an alternative example, one or more portions of the vent assembly 4400 may be formed in one piece with the air delivery conduit 6000, e.g., by over-molding or insert-molding.

In an alternative example, the vent assembly 4400 may be provided to a patient interface 3000, e.g., to the plenum chamber 3200 or connection port 3600, to allow a flow of gas from an interior of the patient interface, e.g., the plenum chamber, to an exterior of the patient interface, e.g., to atmosphere.

As shown in FIGS. 4E to 4H, the vent assembly 4400 comprises a base 4700, a layer of textile material 4600 supported by the base 4700, a cover 4500 to maintain the textile material 4600 within the base 4700, and a membrane 4800 structured and arranged to regulate vent flow through the vent assembly 4400 to provide sufficient washout of gas in use.

The base 4700 includes a base wall 4705 having at least one first orifice 4710 extending through the base wall 4705 to allow gas to be discharged to ambient or atmosphere and at least one second orifice 4720 to allow gas to be discharged to atmosphere. The base wall 4705 includes an interior surface 4730 adapted to be oriented towards the interior of the air delivery conduit 6000 in use, i.e., the pressurizable volume, in use and an exterior surface 4740 adapted to be oriented towards atmosphere in use. A flange or shoulder 4750 is provided along the perimeter of the base wall 4705 to align and support the textile material 4600 on the exterior surface 4740 of the base 4700. A retaining structure 4760 is provided to the interior surface 4730 of the base 4700 to retain the membrane 4800 adjacent the interior surface 4730.

In an example, the base 4700 may be constructed (e.g., molded) of a relatively rigid material, e.g., thermoplastic polymer (e.g., polycarbonate). In an example, the base 4700 may comprise a thickness of about 1-3 mm, e.g., about 2 mm, however other suitable thicknesses are possible.

In the illustrated example, the textile material 4600 includes at least one orifice 4610 extending through the textile material 4600. The textile material 4600 is configured to be supported on the exterior surface 4740 of the base 4700, retained within the flange or shoulder 4750 provided along the perimeter of the base 4700. As illustrated, the textile material 4600 is arranged to cover the first orifice 4710 of the base 4700 so that flow exiting the first orifice 4710 flows into the textile material 4600. Moreover, the orifice 4610 of the textile material 4600 is arranged to align with the second orifice 4720 of the base 4700 so that the second orifice 4720 is not covered by the textile material 4600 and flow exiting the second orifice 4720 will not flow into the textile material 4600.

In an example, the textile material 4600 may be constructed of a porous material that allows gas to flow through the material but diffuses any jet or other flow formation exiting the first orifice 4710, e.g., non-woven fibrous material, woven fibrous material. In an example, the textile material 4600 may comprise a diffusing material which may be similar to or the same as a filter media. In an example, the textile material 4600 may comprise a thickness of about 0.1-0.5 mm, e.g., about 0.25 mm, however other suitable thicknesses are possible. In the illustrated example, the textile material 4600 comprises a single layer, however it should be appreciated that the textile material 4600 may comprise two or more layers, e.g., stacked layers, of similar or dissimilar diffusing materials.

The cover 4500 includes a main wall 4510 and a side wall 4520 that forms the outer periphery of the vent assembly 4400. The main wall 4510 includes a grill-like configuration (e.g., one or more cross-bars) forming slots or outlet orifices 4530 through the cover 4500. The grill-like configuration allows flow therethrough while retaining the textile material 4600 within the base 4700 and minimizing contact, e.g., to prevent contamination.

The cover 4500 is engaged with the base 4700 until the main wall 4510 abuts the flange or shoulder 4750 along the perimeter of the base 4700. The flange or shoulder 4750 supports the cover 4500 and main wall 4510 thereof in spaced relation from the exterior surface 4740 of the base 4700 to accommodate and retain the textile material 4600 between the cover 4500 and the base 4700, i.e., cover 4500 and base 4700 form a casing or cartridge for the textile material 4600. The side wall 4520 of the cover 4500 extends down along the outer periphery of base 4700. The cover 4500 may be removably or permanently secured to the base 4700 in any suitable manner, e.g., press fit assembly, snap or interference fit assembly, adhesive, etc. In the illustrated example, the side wall 4520 also forms the interface with the opening 6050 in the air delivery conduit 6000, e.g., press fit assembly, snap or interference fit assembly, adhesive.

In an example, the cover 4500 may be removably secured to the base, e.g., to allow cleaning and/or replacement of the textile material 4600. Alternatively, the entire vent assembly 4400 may be replaced, rather than replace the individual textile material 4600.

In an alternative example, the vent assembly 4400 may be provided without a cover 4500, and the textile material 4600 may be secured to the base 4700 in other suitable manners, e.g., textile material adhered or overmolded to the base. In this example, the textile material 4600 may be more exposed to facilitate drying. Also, such arrangement eliminates a component to reduce the overall size, e.g., height, of the vent assembly, e.g., lower profile.

In an example, the cover 4500 may be constructed (e.g., molded) of a relatively rigid material, e.g., thermoplastic polymer (e.g., polycarbonate). In an example, the cover 4500 may comprise a height of about 2-5 mm, e.g., about 3.5 mm, however other suitable heights are possible.

The membrane 4800 includes a flap portion 4810 that is movably connected, e.g., hingedly connected by a hinge portion, to a retaining portion 4820 which allows the flap portion 4810 to pivot relative to the retaining portion 4820. The retaining portion 4820 is structured and arranged to engage within a slot 4765 provided to the retaining structure 4760 of the base 4700 to secure the membrane 4800 to the base 4700. The retaining portion 4820 may be removably or permanently secured to the retaining structure 4760 of the base in any suitable manner, e.g., press fit assembly, snap or interference fit assembly, adhesive, etc.

The flap portion 4810 of the membrane 4800 includes an orifice 4815 extending through the flap portion 4810. The membrane 4800 is supported by the retaining structure 4760 adjacent the interior surface 4730 of the base 4700. The flap portion 4810 is freely movable towards and away from the interior surface 4730 of the base, e.g., depending on the presence of pressurized gas and/or blockage of the textile material 4600. The orifice 4815 of the flap portion 4810 is arranged to align with the first orifice 4710 of the base 4710 so that the first orifice 4710 cannot be completely covered or closed by the membrane 4800 to allow flow through the first orifice 4710. Also, the flap portion 4810 is arranged to overlap the second orifice 4720 of the base 4710 so that the second orifice 4720 may be selectively covered or closed by the membrane 4800 to restrict flow through the second orifice 4720.

In an example, the membrane 4800 may be constructed of a relatively flexible, elastic material, e.g., silicone or other thermoplastic elastomer. In an example, the membrane 4800 may comprise a thickness of about 0.25-0.75 mm, e.g., about 0.45 mm, however other suitable thicknesses are possible.

The assembled vent assembly 4400 provides low profile configuration that does not significantly protrude into the interior of the air delivery conduit 6000. In an example, the vent assembly 4400 may comprise a height of about 2-5 mm, e.g., about 3.5 mm, a width of about 5-15 mm, e.g., 10 mm, and a length of about 10-30 mm, e.g., 20 mm, however other suitable dimensions are possible.

In the illustrated example, the vent assembly 4400 and corresponding opening 6050 in the air delivery conduit 6000 includes a stadium-shape, i.e., a rectangle with semicircles at opposite sides. However, it should be appreciated the vent assembly and corresponding opening in the air delivery conduit may have other suitable shapes, e.g., circular and non-circular shapes.

The vent assembly 4400 is structured and arranged to provide (1) a primary vent flow path V1 that passes through the textile material 4600 to diffuse the exhaust vent flow to produce less noise, and (2) a secondary vent flow path V2 that bypasses the textile material 4600 to allow sufficient gas washout when the textile material 4600 is blocked due to water or humidity. The membrane 4800 is structured and arranged to regulate vent flow along the primary and secondary vent flow paths V1, V2.

As described below, the vent assembly 4400 is structured and arranged to allow sufficient vent flow under various scenarios during respiratory therapy, e.g., when there is no air pressure or low pressure in the air delivery conduit 6000, when there is air pressure the air delivery conduit 6000, and when there is air pressure the air delivery conduit 6000 but the textile material 4600 is blocked. The vent assembly 4400 is structured and arranged to operate in adverse conditions, and allow the use of textile material or similar porous material as a safe and reliable vent component for respiratory therapy. In an example, the vent flow may be continuous during respiratory therapy.

As shown in FIG. 4I, when there is no air pressure or low pressure in the air delivery conduit 6000 (e.g., when the RPT device is not operating or the air delivery conduit is occluded in use) and the textile material 4600 is not blocked, the membrane 4800 assumes a rest or not activated position so that air may pass through both the primary and secondary vent flow paths V1, V2. That is, pressurized gas is not delivered to the air delivery conduit 6000 or is not of sufficient magnitude which allows the membrane 4800 to fall or deflect downwardly away from the interior surface 4730 of the base 4700 and the first and second orifices 4710, 4720. As a result, air may pass through the primary vent flow path V1 that extends through the first orifice 4710, through the textile material 4600, and through the cover 4500. In addition, air may pass through the secondary vent flow path V2 extending through the second orifice 4720, through the orifice 4610 in the textile material 4600, and through the cover 4500. When the membrane 4800 is in the rest or not activated position, a large section of the textile material 4600 is exposed through the first orifice 4710, which provides a low impedance air path for patient to breathe in ambient air and exhale through the primary vent flow path V1. The secondary vent flow path V2 also provides a low impedance air path for patient to breathe in ambient air and exhale.

As shown in FIG. 4J, when there is air pressure in the air delivery conduit 6000 (e.g., when the RPT device is operating) and the textile material 4600 is not blocked, the increase in pressure within the pressurized volume of the air delivery conduit 6000 urges or moves the membrane 4800 into an activated position so that air may only pass through the primary vent flow path V1. That is, air pressure in the air delivery conduit 6000 is of sufficient magnitude to force and maintain the membrane 4800 in engagement with the interior surface 4730 of the base 4700. As a result, the orifice 4815 of the flap portion 4810 is arranged to align with the first orifice 4710 of the base 4700 so that air may pass through the primary vent flow path V1 that will extend through the orifice 4815 of the flap portion 4810, through the first orifice 4710 of the base 4700, through the textile material 4600, and through the cover 4500. In addition, the flap portion 4810 is arranged to cover or close the second orifice 4720 of the base 4710 so that air flow through the secondary vent flow path V2 is restricted or blocked by the membrane 4800. When the membrane 4800 is in the activated position, air flow is restricted to the primary vent flow path V1, which directs all flow through the layer of textile material 4600 to atmosphere to diffuse the exhaust vent flow to produce less noise.

Moreover, the orifice 4815 of the flap portion 4810 is suitably sized to regulate flow along the primary vent flow path V1. That is, the orifice 4815 of the flap portion 4810 forms an inlet for exhaust flow along the primary vent flow path V1, and the size of the orifice 4815 (e.g., cross-sectional area of the orifice 4815) may be tuned to provide the desired flow curve within a therapeutic pressure range, e.g., a substantially constant flow rate over a therapeutic pressure range between 4-20 $cmH_2O$.

As shown in FIG. 4K, when there is air pressure in the air delivery conduit 6000 (e.g., when the RPT device is operating) and the textile material 4600 is blocked due to water or humidity, the membrane 4800 will not fully activate so that air may pass through the secondary vent flow path V2 while the primary vent flow path V1 is blocked. That is, the membrane 4800 and the base 4700 are configured and arranged such that blockage of the textile material 4600 alters the flow and force exerted on the membrane 4800, which allows the membrane 4800 to move away from the interior surface 4730 of the base 4700 and the first and second orifices 4710, 4720. As a result, air may pass through the secondary vent flow path V2 that extends through the second orifice 4720, through the orifice 4610 in the textile material 4600, and through the cover 4500. This allows air flow to be restricted to the secondary vent flow path V2, which bypasses the textile material 4600 to provide sufficient vent flow while the textile material 4600 is blocked.

The second orifice 4720 of the base 4700 is suitably sized to regulate flow along the secondary vent flow path V2. That is, the second orifice 4720 of the base 4700 forms an inlet for exhaust flow along the secondary vent flow path V2, and the size of the second orifice 4720 (e.g., cross-sectional area of the orifice 4720) may be tuned to provide the desired flow curve within a therapeutic pressure range, e.g., a substantially constant flow rate over a therapeutic pressure range between 4-20 $cmH_2O$. For example, the second orifice 4720 is tuned to provide sufficient air flow, i.e., low impedance air path, to prevent $CO_2$ build-up in the patient interface.

Moreover, the secondary vent flow path V2 will stay open until the textile material 4600 along the primary vent flow path V1 is sufficiently dry or unblocked to allow sufficient exhaust vent flow.

In an example, the membrane 4800 may be structured and arranged to react to impedance of air flow through the textile material 4600, i.e., react to the extent of wetness or dryness of the textile material 4600. For example, as the textile material 4600 dries, the membrane may progressively move towards the activated position so that air flow through the secondary vent flow path V2 progressively reduces as drying of the textile material 4600 allows air flow through the primary vent flow path V1 to progressively increase. In another example, as the textile material 4600 becomes wetter (e.g., due to humidity), the membrane may progressively move away from the activated position so that air flow through the secondary vent flow path V2 progressively increases as wetness of the textile material 4600 causes air flow through the primary vent flow path V1 to progressively decrease. Thus, the membrane may be structured and arranged to progressively deflect towards and away from the activated position due to dryness of the textile material to divide or apportion the vent flow between the primary and secondary vent flow paths V1, V2 throughout the therapeutic pressure.

As noted above, aspects of the vent assembly 4400 may be tuned to provide a desired flow curve within a therapeutic pressure range. In an example, venting characteristics of each of vent components may be tuned, e.g., based on venting requirement, sound requirement, treatment requirement, etc. This arrangement allows a more customized vent assembly for the patient.

For example, with respect to the membrane 4800, the thickness, length, material, and shape of the membrane may be tuned to deform in a desired manner, and the shape, size, and number of orifices 4815 through the membrane 4800 may be tuned to regulate flow. With respect to the base 4700, the shape, size, and number of the at least one first orifice 4710 and the shape, size, and number of the at least one second orifice 4720 may be tuned to regulate flow. With respect to the textile 4600, the thickness and material of the textile 4600 may be tuned to regulate flow. With respect to the cover 4500, the shape, size, and number of orifices 4530 through the cover 4500 may be tuned to regulate flow.

FIGS. 5A to 5G illustrate a textile vent assembly 4400 according to another example of the present technology. In this example, the vent assembly 4400 further comprises an activator 4900 structured and arranged to deflect the membrane 4800 away from the activated position when the textile material 4600 is exposed to water, i.e., when the textile material is wet such that vent flow drops significantly therethrough.

Similar to the example described above, the vent assembly 4400 in FIGS. 5A to 5G comprises a base 4700, a layer of textile material 4600 supported by the base 4700, a cover 4500 to maintain the textile material 4600 within the base 4700, and a membrane 4800 structured and arranged to regulate vent flow through the vent assembly 4400 to provide sufficient washout of gas in use. In addition, the vent assembly 4400 in FIGS. 5A to 5G comprises an activator 4900 arranged within a recess 4770 provided to the interior surface 4730 of the base 4700 to retain the activator 4900 adjacent the membrane 4800.

In an example, the activator 4900 comprises an expanding polymer material (e-polymer) structured to rapidly expand when exposed to water, such expansion used to engage and deflect the membrane 4800. The higher the percentage of expansion of the material, the lower the thickness of the material required to deflect the membrane 4800. It should be appreciated that any material that can be subjected to a process called osmosis and rapidly expand when exposed to water could be used as the activator. In an alternative example, natural fiber could be used as the activator.

Similar to the above example, as shown in FIG. 5E, when there is no air pressure or low pressure in the air delivery conduit 6000 (e.g., when the RPT device is not operating or the air delivery conduit is occluded in use) and the textile material 4600 is not blocked, the membrane 4800 assumes a rest or not activated position so that air may pass through both the primary and secondary vent flow paths V1, V2.

As shown in FIG. 5F, when there is air pressure in the air delivery conduit 6000 (e.g., when the RPT device is operating) and the textile material 4600 is not blocked, the increase in pressure within the pressurized volume of the air delivery conduit 6000 urges or moves the membrane 4800 into an activated position so that air may only pass through the primary vent flow path V1. When the textile material 4600 and the activator 4900 are dry, the activator 4900 is contracted or in a non-expanded configuration so that the activator 4900 remains submerged or recessed within the recess 4770 and does not affect any deflection of the membrane 4800 from the activated position. Thus, the flap portion 4810 is arranged to cover or close the second orifice 4720 so that air flow is restricted to the primary vent flow path V1, which directs all flow through the layer of textile material 4600 to diffuse the exhaust vent flow to produce less noise.

As shown in FIG. 5G, when there is air pressure in the air delivery conduit 6000 (e.g., when the RPT device is operating) but the textile material 4600 is blocked due to water or humidity, such water or humidity causes the activator to enlarge into an expanded configuration so that the activator 4900 extends out of the recess 4770 to engage and force the membrane 4800 away from the interior surface 4730 of the base 4700 and the first and second orifices 4710, 4720. That is, the activator 4900 becomes active when exposed to water to deflect the membrane 4800 so that air may pass through the secondary vent flow path V2 while the primary vent flow path V1 is blocked. This allows air flow to be restricted to the secondary vent flow path V2, which bypasses the textile material 4600 to provide sufficient vent flow while the textile material 4600 is blocked.

Moreover, the secondary vent flow path V2 will stay open until the textile material 4600 along the primary vent flow path V1 is sufficiently dry or unblocked to allow sufficient exhaust vent flow. For example, the activator 4900 will dry along with the textile material 4600 so that the activator 4900 will remain activated until the textile material 4600 is sufficiently dry or unblocked.

In an example, the membrane 4800 may be structured and arranged to progressively deflect towards and away from the activated position due to dryness of the activator 4900 and hence dryness of the textile material 4600 to divide or apportion the vent flow between the primary and secondary vent flow paths V1, V2 throughout the therapeutic pressure. For example, as the activator 4900 becomes wetter (e.g., due to water or humidity), the activator 4900 may progressively expand to progressively move the membrane 4800 away from the activated position so that air flow through the secondary vent flow path V2 progressively increases as wetness of the textile material 4600 causes air flow through the primary vent flow path V1 to progressively decrease. Likewise, as the activator 4900 dries, the activator 4900 may progressively contract to allow the membrane 4800 to progressively move towards the activated position so that air flow through the secondary vent flow path V2 progressively reduces as drying of the textile material 4600 allows air flow through the primary vent flow path V1 to progressively increase.

FIGS. 6A to 6K illustrate a textile vent assembly 5400 including an activator 5900 according to another example of the present technology. In this example, the vent assembly 5400 is provided without a cover, which enhances exposure of the textile material 5600, e.g., to facilitate drying. Also, such arrangement eliminates a component to reduce the overall size, e.g., height, of the vent assembly, e.g., lower profile.

Similar to the above examples, the vent assembly 5400 is in the form of a vent insert or cartridge structured to be inserted into an opening in a patient interface or an air delivery conduit, e.g., removably or permanently secured within an opening 6050 of an air delivery conduit 6000 as shown in FIGS. 6A to 6D. In an alternative example, one or more portions of the vent assembly 5400 may be formed in one piece with the air delivery conduit 6000, e.g., by over-molding or insert-molding As shown in FIGS. 6E to 6H, the vent assembly 5400 comprises a base 5700, a layer of textile material 5600 supported by the base 5700, a membrane 5800 structured and arranged to regulate vent flow through the vent assembly 5400 to provide sufficient washout of gas in use, and an activator 5900 to deflect the membrane 5800.

The base 5700 includes a base wall 5705 having at least one first orifice 5710 extending through the base wall 5705 to allow gas to be discharged to atmosphere. The base wall 5705 also includes a plurality of second orifices 5720 to allow gas to be discharged to atmosphere. The base wall 5705 includes an interior surface 5730 adapted to be oriented towards the interior of the air delivery conduit 6000 in use, i.e., the pressurizable volume, in use and an exterior surface 5740 adapted to be oriented towards atmosphere in use. In the illustrated example, the plurality of second orifices 5720 extend from a circular protrusion 5742 along the exterior surfaces 5740 to a ramped or sloped protrusion 5732 along the interior surface 5730. A retaining structure 5760 is provided to the interior surface 5730 of the base 5700 to retain the membrane 5800 adjacent the interior surface 5730. Also, an opening 5770 is provided to the base 5700 to retain the activator 5900 adjacent the membrane 5800. In the illustrated example, the periphery of the base 5700 forms the interface with the opening 6050 in the air delivery conduit 6000, e.g., press fit assembly, snap or interference fit assembly, adhesive.

Similar to the above example, it should be appreciated that, the shape, size, and number of second orifices 5720 may be tuned to regulate flow.

In the illustrated example, the textile material 5600 includes at least one orifice 5610 extending through the textile material 5600. The textile material 5600 is configured to be supported and retained on the exterior surface 5740 of the base 5700. The textile material 5600 may be secured to the base 5700 in any suitable manner, e.g., textile material adhered or overmolded to the base. As illustrated, the textile material 5600 is arranged to cover the first orifice 5710 of the base 5700, and the orifice 5610 of the textile material 5600 is arranged to align with the circular protrusion 5742 along the exterior surfaces 5740 so that the plurality of second orifices 5720 are not covered by the textile material 5600.

The membrane 5800 includes a flap portion 5810 that is movably connected, e.g., hingedly connected by a hinge portion, to a retaining portion 5820 which allows the flap portion 5810 to pivot relative to the retaining portion 5820. In the illustrated example, the retaining portion 5820 includes a hole 5822 and the retaining structure 5760 includes a post 5762, the post 5762 structured and arranged to engage with the hole 5822 to secure the membrane 5800 to the base 5700. However, the retaining portion 5820 may be removably or permanently secured to the retaining structure 5760 of the base in any suitable manner, e.g., press fit assembly, snap or interference fit assembly, adhesive, etc.

The membrane 5800 is supported by the retaining structure 5760 adjacent the interior surface 5730 of the base 5700. In the illustrated example, the flap portion 5810 includes sufficient length to overlap the plurality of second orifices 5720 so that the second orifices 5720 may be selectively covered or closed by the membrane 5800 in use.

The activator 5900 is arranged within the opening 5770 of the base 5700 to retain the activator 5900 adjacent the membrane 5800. Similar to the above example, the activator 5900 may comprise an expanding polymer material (e-polymer) or other suitable material that can rapidly expand when exposed to water.

In the illustrated example, the vent assembly 5400 and corresponding opening 6050 in the air delivery conduit 6000 includes a stadium-shape, however it should be appreciated the vent assembly and corresponding opening in the air delivery conduit may have other suitable shapes, e.g., circular and non-circular shapes.

Similar to the above examples, as shown in FIG. 6I, when there is no air pressure or low pressure in the air delivery conduit 6000 (e.g., when the RPT device is not operating or the air delivery conduit is occluded in use) and the textile material 5600 is not blocked, the membrane 5800 assumes a rest or not activated position so that air may pass through both the primary and secondary vent flow paths V1, V2.

As shown in FIG. 6J, when there is air pressure in the air delivery conduit 6000 (e.g., when the RPT device is operating) and the textile material 5600 is not blocked, the increase in pressure within the pressurized volume of the air delivery conduit 6000 urges or moves the membrane 5800 into an activated position so that air may only pass through the primary vent flow path V1. When the textile material 5600 and the activator 5900 are dry, the activator 5900 is contracted or in a non-expanded configuration so that the activator 5900 remains submerged or recessed within the opening 5770 and does not affect any deflection of the membrane 5800 from the activated position. Thus, the flap portion 5810 is arranged to cover or close the plurality of second orifices 5720 so that air flow is restricted to the primary vent flow path V1, which directs all flow through the layer of textile material 5600 to diffuse the exhaust vent flow to produce less noise.

As shown in FIG. 6K, when there is air pressure in the air delivery conduit 6000 (e.g., when the RPT device is operating) but the textile material 5600 is blocked due to water or humidity, such water or humidity causes the activator to enlarge into an expanded configuration so that the activator 5900 extends out of the opening 5770 to engage and force the membrane 5800 away from the interior surface 5730 of the base 5700 and the first orifice 5710 and the plurality of second orifices 5720. That is, the activator 5900 becomes active when exposed to water to deflect the membrane 4500 so that air may pass through the secondary vent flow path V2 while the primary vent flow path V1 is blocked. This allows air flow to be restricted to the secondary vent flow path V2, which bypasses the textile material 5600 to provide sufficient vent flow while the textile material 5600 is blocked.

Similar to the above examples, the secondary vent flow path V2 will stay open until the textile material 5600 along the primary vent flow path V1 is sufficiently dry or unblocked to allow sufficient exhaust vent flow. In addition, the membrane 5800 may be structured and arranged to progressively deflect towards and away from the activated position due to dryness of the activator 5900 and hence dryness of the textile material 5600 to divide or apportion the vent flow between the primary and secondary vent flow paths V1, V2 throughout the therapeutic pressure.

It should be appreciated that the secondary vent flow path V2 may be activated in other manners. For example, FIGS. 7A to 7C show an alternative example of vent assembly 5400 which comprises an electro-magnetic activator 6900 structured and arranged to deflect the membrane 5800.

In this example, the activator 6900 includes a sensor 6910 arranged along the interior surface 5730 of the base 5700. As illustrated, the sensor 6910 includes circuit tracks 6915 configured and arranged to detect water, e.g., detect water between circuit tracks as shown in FIG. 7C. When water is detected, the sensor 6910 activates an electronic switch or control signal which actuates the activator 6900, e.g., activator 6900 includes moving member (e.g., plunger arrangement) structured and arranged to engage and force the membrane 5800 away from the interior surface 5730 of the base 5700 and the first orifice 5710 and the plurality of second orifices 5720. The switch can be set to activate at a certain level of water/moisture presence on the vent assembly. Also, the switch can be set to remain active for a predetermined period of time, e.g., to ensure drying of the textile material 5600 before deactivation. In an example, this vent configuration with electro-magnetic activator 6900 may be used as an active vent, e.g., control vent flow characteristics by controlling flow through primary and secondary vent flow paths V1, V2.

In an alternative example, the vent assembly may simply comprise a sensor configured and arranged to detect water/moisture on the vent assembly, and then provide a signal to the RPT device so the RPT device can warn that patient that the vent is wet and/or update operation accordingly, e.g., update the delivery pressure to ensure safe use of the patient interface during the period when the vent is wet.

FIGS. 8A to 8E show a vent assembly 7400 according to an alternative example of the present technology. In this example, the vent assembly 7400 includes a vent component 7900 comprising an expanding polymer material (e-polymer) structured to rapidly expand when exposed to water, such expansion used to open vent orifices 7925 through the vent component 7900 to activate the secondary vent flow path V2.

As shown in FIGS. 8A to 8C, the vent assembly 7400 comprises a base 7700, a layer of textile material 7600 supported by the base 7700, and vent component 7900 structured and arranged to regulate vent flow through the secondary vent flow path V2 to provide sufficient washout of gas in use.

The base 7700 includes a base wall 7705 having at least one first orifice 7710 extending through the base wall 7705 to allow gas to be discharged to atmosphere and a second orifice 7720 structured to support the vent component 7900.

In the illustrated example, the textile material 7600 is arranged to cover the first orifice 7710 of the base 7700, and the textile material 7600 includes orifice 7610 to align with the second orifice 7720 so that the second orifice 7720 is not covered by the textile material 7600. In this example, the vent assembly 7400 is provided without a cover, and the textile material 7600 may be secured to the base 7700 in any suitable manner, e.g., textile material adhered or overmolded to the base.

In an example, the e-polymer vent component 7900 is in the form of a grommet structured to be inserted into the second orifice 7720 of the base 7700. For example, the vent component 7900 may include a groove 7950 around its periphery, the groove 7950 adapted to locate the vent component 7900 against the edge or rim of the second orifice 7720 of the base 7700. The vent component 7900 and base 7700 are arranged to provide sufficient clearance to allow expansion of the vent component 7900 relative to the base 7700. However, the vent assembly 7400 may be removably or permanently secured within to the base in other suitable manners.

Further, the e-polymer vent component 7900 includes a plurality of vent orifices 7925 structured and arranged to regulate a flow of gas from an interior of the air delivery conduit 6000 to an exterior of the air delivery conduit 6000, e.g., to atmosphere. Specifically, the e-polymer vent component 7900 is structured to expand and contract due to the presence of water/humidity, such expansion/contraction effecting expansion and contraction of the vent orifices 7925 to regulate flow along the secondary vent flow path V2.

It should be appreciated that, the shape, size, and number of second orifices 7925 may be tuned to further regulate flow.

As shown in FIG. 8D, when the textile material 7600 and the e-polymer vent component 7900 are dry, the orifices 7925 of the e-polymer vent component 7900 substantially closed or contract so that little to no flow can flow through the orifices 7925. Thus, air flow is restricted to the primary vent flow path V1, which directs all flow through the layer of textile material 7600 to diffuse the exhaust vent flow to produce less noise.

As shown in FIG. 8E, when the textile material 7600 is blocked due to water or humidity, such water or humidity causes the e-polymer vent component 7900 to enlarge into an expanded configuration which opens or expands the orifices 7925 so that flow can flow through the orifices 7925. This allows air to flow along the secondary vent flow path V2, which bypasses the textile material 7600 to provide sufficient vent flow while the textile material 7600 is blocked. The the e-polymer vent component 7900 will remain activated until the textile material 7600 is sufficiently dry or unblocked.

In an example, the e-polymer vent component 7900 may be structured and arranged to progressively expand and contract due to wetness of the e-polymer vent component 7900 and hence wetness of the textile material 7600 to divide or apportion the vent flow between the primary and secondary vent flow paths V1, V2 throughout the therapeutic pressure. For example, as the e-polymer vent component 7900 becomes wetter (e.g., due to water or humidity), the e-polymer vent component 7900 may progressively expand to progressively open the orifices 7925 so that air flow through the secondary vent flow path V2 progressively increases as wetness of the textile material 7600 causes air flow through the primary vent flow path V1 to progressively decrease. Likewise, as the e-polymer vent component 7900 dries, the e-polymer vent component 7900 may progressively contract to allow the orifices 7925 to progressively close so that air flow through the secondary vent flow path V2 progressively reduces as drying of the textile material 7600 allows air flow through the primary vent flow path V1 to progressively increase.

FIGS. 9A to 9F illustrate a textile vent assembly 8400 according to another example of the present technology. In this example, the vent assembly 8400 comprises a vent member 8500 (e.g., comprising a layer of textile material 8510 with a plurality of vent holes 8530 extending therethrough) and a diffusing member 8600 (e.g., comprising a layer of textile material 8610) along the vent flow path structured and arranged to diffuse the exhaust vent flow to produce less noise. As both the vent member 8500 and the diffusing member 8600 comprise textile material, the vent assembly 8400 may comprises a thinner, more compact, and miniaturized configuration.

In an example, the vent assembly 8400 may be in the form of a vent insert or vent module structured to be inserted into an opening in a patient interface or air delivery conduit, e.g., in a frame or shell of the patient interface forming at least a portion of the plenum chamber.

The vent assembly 8400 may be removably or permanently secured within the opening in any suitable manner, e.g., press fit assembly, snap or interference fit assembly (e.g., vent assembly 8400 may include a groove around its periphery, the groove adapted to locate the vent assembly 8400 against a correspondingly sized rim of the opening of the frame), adhesive.

In an alternative example, one or more portions of the vent assembly 8400 may comprise a portion of the patient interface or air delivery conduit, e.g., frame of the patient interface, or may be formed in one piece (e.g., by overmolding or insert-molding) with the patient interface or air delivery conduit, e.g., frame of the patient interface.

In the illustrated example, the vent assembly 8400 (and the corresponding opening in the frame) includes a stadium-shape, i.e., a rectangle with semicircles at opposite sides. However, it should be appreciated the vent assembly (and the corresponding opening in the frame) may have other suitable shapes, e.g., circular and non-circular shapes.

In use, the vent assembly 8400 is structured and arranged to allow gas flow between a pressurized interior of the patient interface or air delivery conduit, e.g., the plenum chamber, and an exterior of the patient interface or air delivery conduit, e.g., atmosphere.

As shown in the example of FIGS. 9A to 9F, the vent assembly 8400 includes a base or frame 8700, a vent member 8500 (e.g., comprising a layer of textile material 8510 with a plurality of vent holes 8530 extending therethrough) supported by the base 8700, a diffusing member 8600 (e.g., comprising a layer of textile material 8610), and a support structure 8800 to support the diffusing member 8600 in offset or spaced relation from the vent member 8500.

The base 8700 comprises an outer wall 8710 that forms an opening 8720 therethrough. As noted above, the base 8700 may be removably or permanently secured within an opening in the patient interface or air delivery conduit in any suitable manner in order to secure the vent assembly 8400 to the patient interface or air delivery conduit. Alternatively, as noted above, the base 8700 and opening 8720 thereof may comprise a portion of the patient interface or air delivery conduit or be formed in one piece with the patient interface or air delivery conduit, e.g., by over-molding or insert-molding.

The vent member 8500 is supported along the anterior side of the base 8700 by the outer wall 8710 of the base 8700. As illustrated, the vent member 8500 is arranged to cover the opening 8720 of the base 8700 so that a vent flow of gas exhaled by the patient can pass through the opening 8720 and through the plurality of vent holes 8530 in the vent member 8500.

In an example, the textile material 8510 comprises a sheet of textile material having a thickness of about 0.10 mm to 0.30 mm, e.g., 0.19 mm. However, it should be appreciated that other suitable thicknesses are possible. In an example, each of the plurality of vent holes 8530 includes a diameter of about 0.18 mm to 0.20 mm. In an example, the diameter of each of the plurality of vent holes 8530 is no smaller than about 0.18 mm (i.e., greater than about 0.18 mm), e.g., to prevent potential blockage with water. In an example, the plurality of vent holes 8530 may be laser cut through the textile material 8510.

In an example, the textile material 8510 may be attached to the base 8700, and then the vent holes 8530 may be laser cut through the textile material 8510 while attached to the base 8700. In an alternative example, the vent holes 8530 may be laser cut through a textile material 8510, and then the textile material 8510 with the vent holes 8530 may be attached to the base 8700.

The support structure 8800 comprises an outer wall 8810 forming an opening 8820 therethrough and a plurality of support members 8830 protruding from a posterior side of the outer wall 8810. In the illustrated example, the support members 8830 are provided to the outer wall 8810 along major and minor axes of the support structure 8800, however it should be appreciated that the support members 8830 may be arranged along the perimeter of the outer wall 8810 in other suitable manners.

The diffusing member 8600 is supported along the anterior side of the support structure 8800 by the outer wall 8810 of the support structure 8800. In the illustrated example, the diffusing member 8600 comprises a layer of textile material 8610 that is arranged to cover the opening 8820 of the support structure 8600. Moreover, the diffusing member 8600 forms the cover or exterior of the vent assembly 8400. In an example, the textile material of the diffusing member 8600 at the exterior of the vent assembly 8400 facilitates cleaning of the vent assembly 8400. Further, such textile exterior may provide aesthetic appeal, especially when coupled with a textile patient orifice or a textile air delivery conduit.

The support structure 8800 and diffusing member 8600 supported thereon is provided to the anterior side of the base 8700 and vent member 8500 supported thereon. As illustrated, the support members 8830 are arranged to engage along the perimeter of the vent member 8500 so that that vent member 8500 is sandwiched between the support members 8830 and the outer wall 8710 of the base 8700. Moreover, the support members 8830 are arranged to support the outer wall 8810 and the diffusing member 8600 thereon in spaced relation from the anterior side of the base 8700 and vent member 8500. Such arrangement forms lateral openings 8450 along the perimeter of the vent assembly, so that at least a portion of the flow exiting the vent holes 8530 can bypass the diffusing member 8600 and flow through the lateral openings 8450. Such arrangement also offsets the diffusing member 8600 from the vent member 8500 by a gap 8475, which gap 8475 can contend with any moisture or dirt that could potentially clog the diffusing member 8600 while allowing air to continue to flow. In an example, the gap 8475 may have a height of about 1-2 mm, e.g., 1.5 mm. However, it should be appreciated that the gap 8475 may have other suitable sizes, which may vary with the amount of vent flow and the venting area.

In an example, the diffusing member 8600 may be constructed of a porous material that allows gas to flow through the material but diffuses any jet or other flow formation exiting the plurality of vent holes 8530, e.g., textile material 8610 such as a non-woven fibrous material or a woven fibrous material. In an example, the diffusing member 8600 may comprise a textile un-broken loop (UBL) material having a thickness of about 0.10 mm to 0.30 mm, e.g., 0.20 mm. However, it should be appreciated that other suitable textile materials and thicknesses are possible.

In an example, the base 8700 and the support structure 8800 may comprise a relative rigid or a relatively soft construction. As both the vent member 8500 and the diffusing member 8600 comprise a flexible, textile material, the base 8700 and the support structure 8800 (along with the vent member 8500 and the diffusing member 8600) could be curved to follow a profile of the patient interface or air delivery conduit, e.g., soft, flexible construction of the base 8700 and the support structure 8800 may be flexed or bent to follow the profile, or the base 8700 and the support structure 8800 may have a rigid construction that is molded or otherwise formed to follow the profile.

As shown in FIG. 9E, when there is pressure in the patient interface or air delivery conduit (e.g., when the RPT device is operating) and the diffusing member 8600 is not blocked, air may pass through a primary vent flow path V1 that will extend through the plurality of vent holes 8530 and through the diffusing member 8600 to atmosphere to diffuse the exhaust vent flow to produce less noise. In addition, air may pass through secondary vent flow paths V2 that extend through the plurality of vent holes 8530 and through the lateral openings 8450 to atmosphere. Such primary and secondary vent flow paths V1, V2 provide vent paths to allow sufficient gas washout to prevent $CO_2$ build-up in the patient interface or air delivery conduit.

As shown in FIG. 9F, when there is pressure in the patient interface or air delivery conduit (e.g., when the RPT device is operating) and the diffusing member 8600 is blocked due to water or humidity, air may pass through the secondary vent flow paths V2 that extend through the plurality of vent holes 8530 and through the lateral openings 8450 to atmosphere. The secondary vent flow path V2 bypasses the diffusing member 8600 to provide sufficient vent flow while the diffusing member 8600 is blocked. Moreover, the secondary vent flow path V2 is always open which ensures sufficient exhaust vent flow until the diffusing member 8600 along the primary vent flow path V1 is sufficiently dry or unblocked.

FIGS. 10A to 10F illustrate a textile vent assembly 9400 according to another example of the present technology. The vent assembly 9400 is similar to the vent assembly 8400 described above, but includes a different arrangement for supporting the vent member 9500 and the diffusing member 9600.

As shown in the example of FIGS. 10A to 10F, the vent assembly 9400 includes a frame 9700, a vent member 9500 (e.g., comprising a layer of textile material 9510 with a plurality of vent holes 9530 extending therethrough) supported along a posterior side of the frame 9700, and a diffusing member 9600 (e.g., comprising a layer of textile material 9610) supported along an anterior side of the frame 9700. In this example, the frame 9700 supports the diffusing member 9600 in offset or spaced relation from the vent member 9500.

The frame 9700 comprises a posterior wall 9710 forming an opening 9720 therethrough, an anterior wall 9740 forming an opening 9750 therethrough, and a plurality of support members 9730 that spaces and supports the anterior wall 9740 apart from the posterior wall 9710. In the illustrated example, the support members 9730 are provided along major and minor axes of the frame 9700, however it should be appreciated that the support members 9730 may be arranged along the perimeter of frame 9700 in other suitable manners. Also, the posterior wall 9710, anterior wall 9740, and the support members 9730 form lateral openings 9450 along the perimeter of the vent assembly, so that at least a portion of the flow exiting the vent holes 9530 can bypass the diffusing member 9600 and flow through the lateral openings 9450.

The vent member 9500 is supported along the posterior side of the frame 9700 by the posterior wall 9710 of the frame 9700, and the diffusing member 9600 is supported along the anterior side of the frame 9700 by the anterior wall 9740 of the frame 9700. As such, the frame 9700 provides a support structure in which the diffusing member 9600 is supported in spaced relation from the vent member 9500, which forms a gap 9475 to contend with any moisture or dirt that could potentially clog the diffusing member 9600 as described above.

Similar to the vent assembly 8400 described above, the frame 9700 may comprise a relative rigid or a relatively soft construction. As both the vent member 9500 and the diffusing member 9600 comprise a flexible, textile material, the frame 9700 (along with the vent member 9500 and the diffusing member 9600) could be curved to follow a profile of the patient interface or air delivery conduit, e.g., soft, flexible construction of the frame 9700 may be flexed or bent to follow the profile, or the frame 9700 may have a rigid construction that is molded or otherwise formed to follow the profile.

As shown in FIG. 10E, when there is pressure in the patient interface or air delivery conduit (e.g., when the RPT device is operating) and the diffusing member 9600 is not blocked, air may pass through a primary vent flow path V1 that will extend through the plurality of vent holes 9530 and through the diffusing member 9600 to atmosphere to diffuse the exhaust vent flow to produce less noise. In addition, air may pass through secondary vent flow paths V2 that extend through the plurality of vent holes 9530 and through the lateral openings 9450 to atmosphere. Such primary and secondary vent flow paths V1, V2 provide vent paths to allow sufficient gas washout to prevent $CO_2$ build-up in the patient interface or air delivery conduit.

As shown in FIG. 10F, when there is pressure in the patient interface or air delivery conduit (e.g., when the RPT device is operating) and the diffusing member 9600 is blocked due to water or humidity, air may pass through the secondary vent flow paths V2 that extend through the plurality of vent holes 9530 and through the lateral openings 9450 to atmosphere. The secondary vent flow path V2 bypasses the diffusing member 9600 to provide sufficient vent flow while the diffusing member 9600 is blocked. Moreover, the secondary vent flow path V2 is always open which ensures sufficient exhaust vent flow until the diffusing member 9600 along the primary vent flow path V1 is sufficiently dry or unblocked.

In each of the above examples, the total vent flow through the vent assembly may ideally comprise the sum of the primary vent flow through the primary vent flow path V1, the secondary vent flow through the secondary vent flow path V2, and any leaks (e.g., about 0.1-0.2 L/min) in the vent assembly. So for a given pressure, a reduction in the primary vent flow should be made up by an increase in the secondary vent flow. In an example, the change in the rate of vent flow in the primary and secondary vent flow paths may depend on the how quickly moisture builds up and how quickly moisture dries up in the vent assembly. The cross-over of vent flow between the primary and secondary vent flow paths may depend on the design and may be tuned as described above.

FIGS. 11A to 11F are graphs showing some exemplary vent flow possibilities.

In the FIG. 11A example, the vent assembly may be configured such that the secondary vent flow progressively increases as the primary vent flow progressively decreases throughout a therapeutic pressure range.

In the FIG. 11B example, the vent assembly may be configured such that the secondary vent remains closed until a certain therapeutic pressure is reached (e.g., 8 cmH$_2$O), after which the secondary vent flow progressively increases as the primary vent flow continues to progressively decrease.

In the FIG. 11C example, the vent assembly may be configured such that the secondary vent flow progressively increases as the primary vent flow progressively decreases until a certain therapeutic pressure is reached (e.g., 10 cmH$_2$O), such pressure being sufficiently large to clear the blockage in the primary vent, thereafter the secondary vent flow progressively decreases as the primary vent flow progressively increases.

In the FIG. 11D example, the vent assembly may be configured such that the secondary vent is activated once the primary vent is wet (e.g., due to water or humidity). In this example, if the primary vent is wet, the primary vent flow drops by about 50% of its original or dry flow and the secondary vent activates to increase the total vent flow after the vent assembly is exposed to moisture. This increase provided by the secondary vent may be tuned to ensure sufficient gas washout in use.

In the FIG. 11E example, the vent assembly may be configured such that the secondary vent remains closed when the primary vent is wet (e.g., due to water or humidity) until a certain level of water saturation or a certain level of blockage in the primary vent is reached, after which the secondary vent activates to increase the total vent flow. Similar to the example of FIG. 11D, the primary vent flow drops by about 50% of its original or dry flow if the primary vent is wet. In this example, the secondary vent activates at about 8 cmH$_2$O, however it should be appreciated that activation may occur at lower or higher pressures, e.g., depending on the level of water saturation or blockage as noted above. Also, in an example, the secondary vent may be activated electronically via an electromechanical system, e.g., see electro-magnetic activator 6900 described above. The increase of total vent flow provided by the secondary vent may be tuned to ensure sufficient gas washout in use.

In the FIG. 11F example, the vent assembly may be configured such that the secondary vent is activated once the primary vent is wet (e.g., due to water or humidity). In this example, the primary vent flow drops by about 50% of its original or dry flow at low pressures (e.g., less than about 10 cmH$_2$O, e.g., 4-10 cmH$_2$O) because it is wet and the secondary vent activates to increase the total vent flow. At higher pressures (e.g., greater than about 10 cmH$_2$O, e.g., 10-20 cmH$_2$O), the pressure in the vent is sufficient to clear the water or blockage in the primary vent, thereafter the primary vent flow may increase and the secondary vent flow may gradually reduce or remain substantially constant as it becomes dry due to airflow over the components. Over time, the total vent flow may return to the original or dry flow rate. In an example, if the textile material includes small holes between fabric or a tighter weave, more pressure may be required to clear the water or blockage in the primary vent. Likewise, if the textile material includes bigger holes between fabric or a looser, more open weave, less pressure may be required to clear the water or blockage in the primary vent.

In each of the above examples, the diffusing member, e.g., textile material, may include one or more coatings, e.g., hydrophobic and/or hydrophilic coatings. In an example, a hydrophobic coating may be provided to one side of the textile (e.g., patient side) to keep moisture in and a hydrophilic coating may be provided to the other side of the textile (e.g., atmosphere side) to stop moisture from leaving. However, it should be appreciated that other suitable coating arrangements are possible.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200.

In one form this allows a clinician to supply supplemental oxygen. In one form, this allows for the direct measurement of a property of gases within the plenum chamber 3600, such as the pressure.

5.4 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block of the RPT device 4000 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.4.1 Oxygen Delivery

In one form of the present technology, supplemental oxygen may be delivered to one or more points in the pneumatic path, such as upstream of the pneumatic block, to the air circuit 4170 and/or to the patient interface 3000.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.5.4 Anatomy 5.5.4.1 Anatomy of the Face

Ala: the external outer wall or "wing" of each nostril (plural: alar).

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.5.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at pointp on a surface, and the resulting plane curves. FIGS. 3B to 3F also illustrate an outward normal vector atp. The outward normal vector atp points away from the surface. In some examples we describe the surface from the point of view of an imaginary small person standing upright on the surface.

5.5.6.1 Curvature in One Dimension

The curvature of a plane curve atp may be described as having a sign (e.g. positive, negative) and a magnitude (e.g. 1/radius of a circle that just touches the curve atp).

Positive curvature: If the curve atp turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve atp is a straight line, the curvature will be taken to be zero (if the imaginary small person leaves the pointp, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures atp are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S.

With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.5.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 REFERENCE SIGNS LIST

| Feature Item | Number |
| --- | --- |
| patient | 1000 |
| bed partner | 1100 |
| patient interface | 3000 |
| seal-forming structure | 3100 |
| plenum chamber | 3200 |
| positioning and stabilising structure | 3300 |
| vent | 3400 |
| connection port | 3600 |
| forehead support | 3700 |
| RPT device | 4000 |
| air circuit | 4170 |
| vent assembly | 4400 |
| cover | 4500 |
| main wall | 4510 |
| side wall | 4520 |
| orifices | 4530 |
| textile material | 4600 |
| orifice | 4610 |
| base | 4700 |
| base wall | 4705 |
| first orifice | 4710 |
| second orifice | 4720 |
| interior surface | 4730 |
| exterior surface | 4740 |
| shoulder | 4750 |
| retaining structure | 4760 |
| slot | 4765 |
| recess | 4770 |
| membrane | 4800 |
| flap portion | 4810 |
| orifice | 4815 |
| retaining portion | 4820 |
| activator | 4900 |

-continued

5.7 REFERENCE SIGNS LIST

| Feature Item | Number |
|---|---|
| humidifier | 5000 |
| vent assembly | 5400 |
| textile material | 5600 |
| orifice | 5610 |
| base | 5700 |
| base wall | 5705 |
| first orifice | 5710 |
| second orifices | 5720 |
| interior surface | 5730 |
| protrusion | 5732 |
| exterior surface | 5740 |
| protrusion | 5742 |
| retaining structure | 5760 |
| post | 5762 |
| opening | 5770 |
| membrane | 5800 |
| flap portion | 5810 |
| retaining portion | 5820 |
| hole | 5822 |
| activator | 5900 |
| air delivery conduit | 6000 |
| opening | 6050 |
| base | 6700 |
| interior surface | 6730 |
| activator | 6900 |
| sensor | 6910 |
| circuit tracks | 6915 |
| vent assembly | 7400 |
| textile material | 7600 |
| orifice | 7610 |
| base | 7700 |
| base wall | 7705 |
| first orifice | 7710 |
| second orifice | 7720 |
| vent component | 7900 |
| second orifices | 7925 |
| groove | 7950 |
| vent assembly | 8400 |
| lateral opening | 8450 |
| gap | 8475 |
| vent member | 8500 |
| textile material | 8510 |
| vent holes | 8530 |
| diffusing member | 8600 |
| textile material | 8610 |
| base | 8700 |
| outer wall | 8710 |
| opening | 8720 |
| support structure | 8800 |
| outer wall | 8810 |
| opening | 8820 |
| support members | 8830 |
| vent assembly | 9400 |
| lateral opening | 9450 |
| gap | 9475 |
| vent member | 9500 |
| textile material | 9510 |
| vent holes | 9530 |
| diffusing member | 9600 |
| textile material | 9610 |
| frame | 9700 |
| posterior wall | 9710 |
| opening | 9720 |
| support members | 9730 |
| anterior wall | 9740 |
| opening | 9750 |

The invention claimed is:

1. A patient interface configured to deliver a supply of gas at positive pressure to an entrance of a patient's airways for respiratory therapy, the patient interface comprising:
a plenum chamber pressurizable to a therapeutic pressure above ambient air pressure;
a seal-forming structure constructed and arranged to form a seal with a region of a patient's face surrounding an entrance to a patient's airways; and
a vent assembly configured to provide a vent flow of gas to discharge gas exhaled by the patient from the plenum chamber to ambient, the vent assembly comprising:
a base including at least one first orifice extending through the base to allow gas to be discharged from the plenum chamber to ambient along a primary vent flow path and at least one second orifice to allow gas to be discharged from the plenum chamber to ambient along a secondary vent flow path;
a diffusing member provided to the base, the diffusing member configured and arranged such that the at least one first orifice is covered by the diffusing member along the primary vent flow path and the at least one second orifice is not covered by the diffusing member or a diffusing member along the secondary vent flow path; and
a vent component provided to the at least one second orifice of the base, the vent component including a plurality of vent orifices,
wherein the vent component comprises an expanding polymer material structured and arranged to regulate the vent flow of gas along the secondary vent flow path throughout respiratory therapy.

2. The patient interface according to claim 1, wherein the vent component is configured to expand and contract due to a presence of water or humidity, and expansion and contraction of the vent component is configured to effect expansion and contraction of the plurality of vent orifices to regulate flow along the secondary vent flow path.

3. The patient interface according to claim 1, wherein the vent component is configured to expand when the diffusing member is blocked along the primary vent flow path so the vent flow of gas is restricted to the secondary vent flow path.

4. The patient interface according to claim 3, wherein the secondary vent flow path bypasses the diffusing member along the primary vent flow path to allow the vent flow of gas when the diffusing member is blocked due to water or humidity.

5. The patient interface according to claim 1, wherein the diffusing member along the primary vent flow path comprises a textile material.

6. The patient interface according to claim 1, wherein the vent component includes a groove around its periphery, the groove adapted to locate the vent component against an edge or rim of the at least one second orifice of the base.

7. The patient interface according to claim 1, wherein the vent component is configured to contract when dry so that the vent flow of gas is restricted to the primary vent flow path.

8. The patient interface according to claim 1, wherein the vent component is structured and arranged to progressively expand and contract due to wetness of the vent component and hence wetness of the diffusing member along the primary vent flow path to divide or apportion the vent flow of gas between the primary and secondary vent flow paths throughout the respiratory therapy.

9. The patient interface according to claim 1, wherein the diffusing member along the primary vent flow path comprises one or more coatings to retain moisture.

10. The patient interface according to claim 9, wherein the one or more coatings comprises a hydrophobic coating provided to a patient side of the diffusing member along the primary vent flow path to keep moisture in and/or the one or more coatings comprises a hydrophilic coating provided to an atmosphere side of the diffusing member to stop moisture from leaving.

11. A patient interface configured to deliver a supply of gas at positive pressure to an entrance of a patient's airways for respiratory therapy, the patient interface comprising:
   a plenum amber pressurizable to a therapeutic pressure above ambient air pressure;
   a seal-forming structure constructed and arranged to form a seal with a region of a patient's face surrounding an entrance to a patient's airways; and
   a vent assembly configured to provide a vent flow of gas to discharge gas exhaled by the patient from the plenum chamber to ambient, the vent assembly comprising:
      a base including at least one first orifice extending through the base to allow gas to be discharged from the plenum chamber to ambient along a primary vent flow path and at least one second orifice to allow gas to be discharged from the plenum chamber to ambient along a secondary vent flow path;
      a diffusing member provided to the base, the diffusing member configured and arranged such that the at least one first orifice is covered by the diffusing member along the primary vent flow path and the at least one second orifice is not covered by the diffusing member along the secondary vent flow path, wherein the diffusing member comprises a textile material; and
      a vent component provided to the at least one second orifice of the base, the vent component including a plurality of vent orifices,
      wherein the vent component comprises an expanding polymer material structured and arranged to regulate the vent flow of gas along the secondary vent flow path throughout respiratory therapy.

12. The patient interface according to claim 11, wherein the vent component is configured to expand and contract due to a presence of water or humidity, and expansion and contraction of the vent component is configured to effect expansion and contraction of the plurality of vent orifices to regulate flow along the secondary vent flow path.

13. The patient interface according to claim 11, wherein the vent component is configured to expand when the diffusing member is blocked along the primary vent flow path so the vent flow of gas is restricted to the secondary vent flow path.

14. The patient interface according to claim 13, wherein the secondary vent flow path bypasses the diffusing member to allow the vent flow of gas when the diffusing member is blocked due to water or humidity.

15. The patient interface according to claim 11, wherein the diffusing member along the primary vent flow path comprises one or more coatings to retain moisture.

16. The patient interface according to claim 15, wherein the one or more coatings comprises a hydrophobic coating provided to a patient side of the diffusing member along the primary vent flow path to keep moisture in and/or the one or more coatings comprises a hydrophilic coating provided to an atmosphere side of the diffusing member to stop moisture from leaving.

17. A patient interface configured to deliver a supply of gas at positive pressure to an entrance of a patient's airways for respiratory therapy, the patient interface comprising:
   a plenum chamber pressurizable to a therapeutic pressure above ambient air pressure;
   a seal-forming structure constructed and arranged to form a seal with a region of a patient's face surrounding an entrance to a patient's airways; and
   a vent assembly configured to provide a vent flow of gas to discharge gas exhaled by the patient from the plenum chamber to ambient, the vent assembly comprising:
      a base including at least one first orifice extending through the base to allow gas to be discharged from the plenum chamber to ambient along a primary vent flow path and at least one second orifice to allow gas to be discharged from the plenum chamber to ambient along a secondary vent flow path;
      a diffusing member provided to the base, the diffusing member configured and arranged such that the at least one first orifice is covered by the diffusing member along the primary vent flow path and the at least one second orifice is not covered by the diffusing member along the secondary vent flow path; and
      a vent component provided to the at least one second orifice of the base, the vent component including a plurality of vent orifices;
      wherein the vent component comprises an expanding polymer material structured and arranged to regulate the vent flow of gas along the secondary vent flow path throughout respiratory therapy, and
      wherein the vent component s configured to expand and contract due to presence of water or humidity.

18. The patient interface according to claim 17, wherein expansion and contraction of the vent component is configured to effect expansion and contraction of the plurality of vent orifices to regulate flow along the secondary vent flow path.

19. The patient interface according to claim 17, wherein the vent component is configured to expand when the diffusing member is blocked along the primary vent flow path so the vent flow of gas is restricted to the secondary vent flow path.

20. The patient interface according to claim 17, wherein the secondary vent flow path bypasses the diffusing member to allow the vent flow of gas when the diffusing member is blocked due to water or humidity.

21. The patient interface according to claim 17, wherein the diffusing member comprises a textile material.

22. The patient interface according to claim 17, wherein the diffusing member along the primary vent flow path comprises one or more coatings to retain moisture.

23. The patient interface according to claim 22, wherein the one or more coatings comprises a hydrophobic coating provided to a patient side of the diffusing member along the primary vent flow path to keep moisture in and/or the one or more coatings comprises a hydrophilic coating provided to an atmosphere side of the diffusing member to stop moisture from leaving.

24. A patient interface configured to deliver a supply of gas at positive pressure to an entrance of a patient's airways for respiratory, the patient interface comprising:
   a plenum chamber pressurizable to a therapeutic pressure above ambient air pressure;
   a seal-forming structure constructed and arranged to form a seal with a region of a patient's face surrounding an entrance to a patient's airways; and
   a vent assembly configured to provide a vent flow of gas to discharge gas exhaled by the patient from the plenum chamber to ambient, the vent assembly comprising:
      a base including at least one first orifice extending through the base to allow gas to be discharged from the plenum chamber to ambient along a primary vent flow path and at least one second orifice to allow gas to be discharged from the plenum chamber to ambient along a secondary vent flow path;

a diffusing member provided to the base, the diffusing member configured and arranged such that the at least one first orifice is covered by the diffusing member along the primary vent flow path and the at least one second orifice is not covered by the diffusing mem along the secondary vent flow path; and a vent component provided to the at least one second orifice of the base, the vent component including a plurality of vent orifices, wherein the vent component comprises an expanding polymer material structured and arranged to regulate the vent flow of gas along the secondary vent flow path throughout respiratory therapy, and wherein the vent component is configured to expand when the diffusing member is blocked along the primary vent flow path so the vent flow of gas is restricted to the secondary vent flow path.

25. The patient interface according to claim 24, wherein the vent component is configured to expand and contract due to a presence of water or humidity, and expansion and contraction of the vent component is configured to effect expansion and contraction of the plurality of vent orifices to regulate flow along the secondary vent flow path.

26. The patient interface according to claim 24, wherein the secondary vent flow path bypasses the diffusing member to allow the vent flow of gas when the diffusing member is blocked due to water or humidity.

27. The patient interface according to claim 24, wherein the diffusing member comprises a textile material.

28. The patient interface according to claim 24, wherein the diffusing member along the primary vent flow path comprises one or more coatings to retain moisture.

29. The patient interface according to claim 28, wherein the one or more coatings comprises a hydrophobic coating provided to a patient side of the diffusing member along the primary vent flow path to keep moisture in and/or the one or more coatings comprises a hydrophilic coating provided to an atmosphere side of the diffusing member to stop moisture from leaving.

30. A patient interface configured to deliver a supply of gas at positive pressure to an entrance of a patient's airways for respiratory therapy, the patient interface comprising:

a plenum chamber pressurizable to a therapeutic pressure above ambient air pressure;

a seal-forming structure constructed and arranged to form a seal with a region of a patient's face surrounding an entrance to a patient's airways; and a vent assembly configured to provide a vent flow of gas to discharge gas exhaled by the patient from the plenum chamber to ambient, the vent assembly comprising:

a base including at least one first orifice extending through the base to allow gas to be discharged from the plenum chamber to ambient along a primary vent flow path and at least one second orifice to allow gas to be discharged from the plenum chamber to ambient along a secondary vent flow path, wherein the primary vent flow path is configured to handle at least a majority of a total vent flow through the vent assembly;

a diffusing member provided to the base, the diffusing member configured and arranged such that the at least one first orifice is covered by the diffusing member along the primary vent flow path and the at least one second orifice is not covered by the diffusing member along the secondary vent flow path; and a vent component provided to the at least one second orifice of the base, the vent component including a plurality of vent orifices, wherein the vent component comprises an expanding polymer material structured and arranged to regulate the vent flow of gas along the secondary vent flow path throughout respiratory therapy.

31. The patient interface according to claim 30, wherein the vent component is configured to expand and contract due to a presence of water or humidity, and expansion and contraction of the vent component is configured to effect expansion and contraction of the plurality of vent orifices to regulate flow along the secondary vent flow path.

32. The patient interface according to claim 30, wherein the vent component is configured to expand when the diffusing member is blocked along the primary vent flow path so the vent flow of gas is restricted to the secondary vent flow path.

33. The patient interface according to claim 32, wherein the secondary vent flow path bypasses the diffusing member to allow the vent flow of gas when the diffusing member is blocked due to water or humidity.

34. The patient interface according to claim 30, wherein the diffusing member comprises a textile material.

35. The patient interface according to claim 30, wherein the diffusing member along the primary vent flow path comprises one or more coatings to retain moisture.

36. The patient interface according to claim 35, wherein the one or more coatings comprises a hydrophobic coating provided to a patient side of the diffusing member along the primary vent flow path to keep moisture in and/or the one or more coatings comprises a hydrophilic coating provided to an atmosphere side of the diffusing member to stop moisture from leaving.

\* \* \* \* \*

UNITED STATES PATENT AND TRADEMARK OFFICE
CERTIFICATE OF CORRECTION

PATENT NO. : 11,896,761 B2
APPLICATION NO. : 17/854105
DATED : February 13, 2024
INVENTOR(S) : Dantanarayana et al.

It is certified that error appears in the above-identified patent and that said Letters Patent is hereby corrected as shown below:

In the Claims

Column 55, Line 7, Claim 11, delete "a plenum amber" and insert --a plenum chamber--.

Column 56, Line 26, Claim 17, delete "component s" and insert --component is--.

Column 57, Line 9, Claim 24, delete "mem along" and insert --member along--.

Signed and Sealed this
Twenty-eighth Day of May, 2024

Katherine Kelly Vidal
*Director of the United States Patent and Trademark Office*